US012145966B2

(12) United States Patent
Matoba

(10) Patent No.: US 12,145,966 B2
(45) Date of Patent: Nov. 19, 2024

(54) ACTINOHIVIN VARIANT POLYPEPTIDES AND METHODS OF TREATMENT USING THEM

(71) Applicant: University of Louisville Research Foundation, Inc., Louisville, KY (US)

(72) Inventor: Nobuyuki Matoba, Owensboro, KY (US)

(73) Assignee: UNIVERSITY OF LOUISVILLE RESEARCH FOUNDATION, INC., Louisville, KY (US)

( * ) Notice: Subject to any disclaimer, the term of this patent is extended or adjusted under 35 U.S.C. 154(b) by 858 days.

(21) Appl. No.: 16/485,021

(22) PCT Filed: Feb. 9, 2018

(86) PCT No.: PCT/US2018/017617

§ 371 (c)(1),
(2) Date: Aug. 9, 2019

(87) PCT Pub. No.: WO2018/148541

PCT Pub. Date: Aug. 16, 2018

(65) Prior Publication Data

US 2023/0174595 A1 Jun. 8, 2023

Related U.S. Application Data

(60) Provisional application No. 62/457,308, filed on Feb. 10, 2017.

(51) Int. Cl.

| | |
|---|---|
| ***C07K 14/36*** | (2006.01) |
| ***A61K 38/00*** | (2006.01) |
| ***A61P 1/00*** | (2006.01) |
| ***A61P 11/00*** | (2006.01) |
| ***A61P 31/18*** | (2006.01) |
| ***A61P 35/00*** | (2006.01) |
| ***A61P 35/04*** | (2006.01) |
| ***C12N 15/82*** | (2006.01) |

(52) U.S. Cl.

CPC ................ *C07K 14/36* (2013.01); *A61P 1/00* (2018.01); *A61P 11/00* (2018.01); *A61P 31/18* (2018.01); *A61P 35/00* (2018.01); *A61P 35/04* (2018.01); *C12N 15/8258* (2013.01); *A61K 38/00* (2013.01); *C07K 2319/30* (2013.01)

(58) Field of Classification Search

CPC ..... C07K 14/36; C07K 2319/30; A61P 31/18; C12N 15/8258

See application file for complete search history.

(56) References Cited

U.S. PATENT DOCUMENTS

| | | | |
|---|---|---|---|
| 8,802,822 | B2 | 8/2014 | Matoba et al. |
| 2008/0254507 | A1 | 10/2008 | Tanaka et al. |
| 2009/0117106 | A1 | 5/2009 | Satomaa et al. |
| 2013/0288272 | A1 | 10/2013 | Narimatsu et al. |
| 2014/0314761 | A1 | 10/2014 | Matoba et al. |
| 2015/0125517 | A1 | 5/2015 | McDonald et al. |
| 2017/0242015 | A1 | 8/2017 | Mechta-Grigoriou et al. |
| 2024/0092841 | A1 | 3/2024 | Matoba |
| 2024/0123026 | A1 | 4/2024 | Matoba et al. |

FOREIGN PATENT DOCUMENTS

| | | | |
|---|---|---|---|
| WO | WO 2008/069290 | A1 | 6/2008 |
| WO | WO 2015/197919 | A1 | 12/2015 |
| WO | 201814854 | A1 | 8/2018 |
| WO | WO 2022/159413 | | 1/2022 |
| WO | WO 2022/187851 | A1 | 9/2022 |

OTHER PUBLICATIONS

Arnold, K., et al., "The Swiss-Model workspace: a web-based environment for protein structure homology modelling", 22(2): 195-201 (2006).

Balzarini, J., "Targeting the glycans of glycoproteins: a novel paradigm for antiviral therapy", Microbiology, 5: 583-597 (Aug. 2007).

Benoist, H., et al., "Two structurally identical mannose-specific jacalin-related lectins display different effects on human T lymphocyte activation and cell death", Journal of Leukocyte Biology, 86: 103-114 (Jul. 2009).

Czajkowsky, D.M., et al., "Fc-fusion proteins: new developments and future perspectives", EMBO Mol. Med (2012) 4, 1015-1028.

De Leoz, M.L.A., et al., "High-Mannose Glycans are Elevated during Breast Cancer Progression", Molecular & Cellular Proteomics, (10(1):M110.002717. doi: 10.1074/mcp.M110.002717 (2011).

Everest-Dass, A.V., "N-glycan MALDI Imaging Mass Spectrometry on Formalin-Fixed Paraffin-Embedded Tissue Enables the Delineation of Ovarian Cancer Tissues", 15.9, 3003-3016 (2016).

Forthal, D.N., et al., "Rhesus Macaque Polyclonal and Monoclonal Antibodies Inhibit Simian Immunodefiency Virus in the Presence of Human or Autologous Rhesus Effector Cells", Journal of virology, 80(18): 9217-9225 (Sep. 2006).

Gleba, Y., et al., "Magnifection—a new platform for expressing recombinant vaccines in plants", Vaccine 23, 2042-2048 (2005).

Hamorsky, K.T., et al., "Efficient Single Tobamoviral Vector-Based Bioproduction of Broadly Neutralizing Anti-HIV-1 Monoclonal Antibody VRC01 in *Nicotiana benthamiana* Plants and Utility of VRC01 in Combination Microbicides", Antimicrobial Agents and Chemotherapy, 57(5): 2076-2086 (May 2013).

(Continued)

*Primary Examiner* — Elly-Gerald Stoica

(74) *Attorney, Agent, or Firm* — Hamilton, Brook, Smith & Reynolds, P.C.

(57) ABSTRACT

Polypeptides are provided that include an actinohivin variant polypeptide. The actinohivin variant polypeptide can be operably connected to an antibody fragment, such as a fragment crystallizable (Fc) region of immunoglobulin (Ig) G. Nucleic acid sequences, expression vectors, and transformed plant cells useful for producing the polypeptides are also provided. Further provided are methods for treating a viral infection or a cancer in a subject and include the step of administering the actinohivin variant polypeptide to the subject.

17 Claims, 34 Drawing Sheets

Specification includes a Sequence Listing.

(56) References Cited

OTHER PUBLICATIONS

Hivrale, AU, et al., "Plant as a plenteous reserve of lectin", Plant Signaling & Behavior, 8(12): e26595-1-e26595-7 (Dec. 2013).
Holst, S., et al., "N-glycosylation Profiling of Colorectal Cancer Cell Lines Reveals Association of Fucosylation with Dieefferentiation and Caudal Type Homebox 1 (CDS1)/Villin mRNA Expression", Molecular & Cellular Proteomics 15.1, 124-140 (2016).
Hoorelbeke, B., et al., "Actinohivin, a Broadly Neutralizing Prokaryotic Lectin, Inhibits HIV-1 Infection by Specifically Targeting High-Mannose-Type Glycans on the gp120 Envelope", Antimicrobial Agents and Chemotherapy, 54(8): 3287-3301 (Aug. 2010).
International Search Report and Written Opinion for International Application No. PCT/US2018/017617, "Actinohivin Variant Polypeptides and Related Methods", dated Aug. 22, 2019.
Kouokam, J.C., et al., "Investigation of Griffithsin's Interactions with Human Cells Confirms Its Outstanding Safety and Efficacy Profile as a Microbicide Candidate", PLOS One, 6(8): e22635, 15 pages (Aug. 2011).
Lam, S.K., et al., "Lectins: production and practical applications", Appl Microbiol. Biotechnol (2011) 89: 45-55.
Li, W.W., et al., "Concanavalin A: a potential anti-neoplastic agent targeting apoptosis, autophagy and anti-angiogenesis for cancer therapeutics", Biochemical and biophysical research communications, 414, 282-286 (2011).
Liu, X., et al., "Cell Surface-Specific N-Glycan Profiling in Breast Cancer", PLOS, 8*8): e72704, 11 pgs (Aug. 2013).
Marillonnet, S., et al., "In planta engineering of viral RNA replicons: Efficient assembly by recombination of DNA modules delivered by *Agrobacterium*", PNAS, 101(18): 6852-6857 (May 4, 2004).
Matoba, N. et alc., "HIV-1 Neutralization Profile and Plant-Based Recombinant Expression of Actinohivin, an Env Glycan-Specific Lectin Devoid of T-Cell Mitogenic Activity", PLOS One, 5(6): e11143, 11 pgs (Jun. 2010).
Molinari, M., "N-glycan structure dictates extension of protein folding or onset of disposal", Nature Chemical Biology, 3(6): 313-320 (Jun. 2007).
Newsom-Davis, T.E., et al., "Enhanced Immune Recognition of Cryptic Glycan Markers in Human Tumors", Cancer Res 2009; 69(5): 2018-2025.
Notification Concerning Transmittal of International Preliminary Report on Patentability for International Application No. PCT/US2018/017617, "Actinohivin Variant Polypeptides and Related Methods", dated Aug. 22, 2019.
Oliveira, C., et al., "Recombinant lectins: an array of tailor-made glycan-interaction biosynthetic tools", Critical reviews in biotechnology, 33, 66-80 (2013).
Sharon, N., "Lectins: Carbohydrate-specific Reagents and Biological Recognition Molecules", The Journal of Biological Chemistry 282(5): 2753-2764 (Feb. 2, 2007).
Tanaka, H., "Mechanism by which the lectin actinohivin blocks HIV infection of target cells", PNAS 106(37): 15633-15638 (Sep. 15, 2009).
Zhang, F. et al., "The Characteristic Structure of Anti-HIV Actinohivin in Complex with Three HMTG D1 Chains of HIV-gp120", Chembiochem : a European journal of chemical biology, 15(18): 2766-2773 (Dec. 15, 2014).
Aghajanian, C., et al., "OCEANS: a randomized, double-blind, placebo-controlled phase III trial of chemotherapy with or without bevacizumab in patients with platinum-sensitive recurrent epithelial ovarian, primary peritoneal, or fallopian tube cancer," *Journal of Clinical Oncology*, 30(17): 2039-2045 (2012).
Ahmed AA et al., "Structural characterization of Gasdalie Fc bound to the activating Fc receptor FcγRIIIa," *J Struct Biol*, 194(1): 78-89 (Apr. 2016).
Alonso-Garcia, V, Chaboya, C, Li, Q, Le, B, Congleton, TJ, Florez, J, et al. (2020). High Mannose N-Glycans Promote Migration of Bone-Marrow-Derived Mesenchymal Stromal Cells. Int J Mol Sci 21.
Al-Saad, S, Richardsen, E, Kilvaer, TK, Donnem, T, Andersen, S, Khanehkenari, M, et al. (2017). The impact of MET, IGF-1, IGF1R expression and EGFR mutations on survival of patients with non-small-cell lung cancer. PLoS One 12: e0181527.
Anugraham, M., et al., "Specific glycosylation of membrane proteins in epithelial ovarian cancer cell lines: glycan structures reflect gene expression and DNA methylation status," *Molecular & Cellular Proteomics*, 13.9: 2213-2232 (2014).
Boyaval, F, Van Zeijl, R, Dalebout, H, Holst, S, van Pelt, G, Farina-Sarasqueta, A, et al. (2021). N-glycomic signature of stage II colorectal cancer and its association with the tumor microenvironment. Mol Cell Proteomics: 100057.
Bray, F., et al., "Global cancer statistics 2018: Globocan estimates of incidence and mortality worldwide for 36 cancers in 185 countries," *CA: A Cancer Journal for Clinicians*, 68(6): 394-424 (2018).
Chen, H, Deng, Z, Huang, C, Wu, H, Zhao, X, and Li, Y (2017). Mass spectrometric profiling reveals association of N-glycan patterns with epithelial ovarian cancer progression. Tumour Biol 39: 1010428317716249.
Chik, JH, Zhou, J, Moh, ES, Christopherson, R, Clarke, SJ, Molloy, MP, et al. (2014). Comprehensive glycomics comparison between colon cancer cell cultures and tumours: implications for biomarker studies. J Proteomics 108: 146-162.
Choi, Y., et al., "Studying cancer immunotherapy using patient-derived xenografts (PDXs) in humanized mice," *Experimental & Molecular Medicine*, 50(8): 99 (2018).
Coleman, R.L., et al., "Bevacizumab and paclitaxel-carboplatin chemotherapy and secondary cytoreduction in recurrent, platinum-sensitive ovarian cancer (NRG Oncology/Gynecologic Oncology Group study GOG-0213): a multicentre, open-label, randomised, phase 3 trial," *The Lancet Oncology*, 18(6): 779-791 (2017).
Coleman, R.L., et al., "Rucaparib maintenance treatment for recurrent ovarian carcinoma after response to platinum therapy (ARIEL3): a randomised, double-blind, placebo-controlled, phase 3 trial," *The Lancet*, 390(10106): p. 1949-1961 (2017).
Dent, M., et al., "Safety and Efficacy of Avaren-Fc Lectibody Targeting HCV High-Mannose Glycans in a Human Liver Chimeric Mouse Model," *Cellular and Molecular Gastroenterology and Hepatology*, 11(1): 185-198 (2021).
Engelman, JA, and Cantley, LC (2006). The role of the ErbB family members in non-small cell lung cancers sensitive to epidermal growth factor receptor kinase inhibitors. Clin Cancer Res 12: 4372s-4376s.
Friedl, P, and Wolf, K (2003). Tumour-cell invasion and migration: diversity and escape mechanisms. Nat Rev Cancer 3: 362-374.
Gaudinski et al., VRC 606 Study Team. "Safety and pharmacokinetics of the Fc-modified HIV-1 human monoclonal antibody Vrcoils: A Phase 1 open-label clinical trial in healthy adults," *PLoS Med.*, 15(1): e1002493 (Jan. 2018).
Gentilini, D, Busacca, M, Di Francesco, S, Vignali, M, Vigano, P, and Di Blasio, AM (2007). PI3K/Akt and ERK1/2 signalling pathways are involved in endometrial cell migration induced by 17beta-estradiol and growth factors. Mol Hum Reprod 13: 317-322.
Ghisoni, E., et al., "Ovarian Cancer Immunotherapy: Turning up the Heat," *International Journal of Molecular Sciences*, 20(12): 16 pages (2019).
Guo, XF, Zhu, XF, Cao, HY, Zhong, GS, Li, L, Deng, BG, et al. (2017). A bispecific enediyne-energized fusion protein targeting both epidermal growth factor receptor and insulin-like growth factor 1 receptor showing enhanced antitumor efficacy against non-small cell lung cancer. Oncotarget 8: 27286-27299.
Guo, Z., et al., "PD-1 blockade and OX40 triggering synergistically protects against tumor growth in a murine model of ovarian cancer," PloS one, 9(2): eB9350, 10 pages (2014).
Hamanishi, J., et al., "Safety and antitumor activity of anti-PD-1 antibody, nivolumab, in patients with platinum-resistant ovarian cancer," Journal of Clinical Oncology, 33(34): 4015-4022 (2015).
Hamorsky, K.T., et al., "Engineering of a Lectibody Targeting High-Mannose-Type Glycans of the HIV Envelope," *Molecular Therapy*, 27(11): 2038-2052 (2019).

(56) References Cited

OTHER PUBLICATIONS

Huang, F, Xu, LA, and Khambata-Ford, S (2012). Correlation between gene expression of IGF-1R pathway markers and cetuximab benefit in metastatic colorectal cancer. Clin Cancer Res 18: 1156-1166.
ImmunoGen Inc., "ImmunoGen Announces Top-Line Results from Phase 3 Forward I Study of Mirvetuximab Soravtansine in Ovarian Cancer," 2 pages (2019). [cited Apr. 13, 2020]; Available from: http://investor.immunogen.com/news-releases/news-release-details/immunogen-announces-top-line-results-phase-3-forward-i-study.
International Preliminary Report on Patentability for International Application No. PCT/US2022/012853, "Actinohivin Variant Polypeptides and Related Methods" date of completion: Jul. 20, 2023.
Janku, F, Garrido-Laguna, I, Petruzelka, LB, Stewart, DJ, and Kurzrock, R (2011). Novel therapeutic targets in non-small cell lung cancer. J Thorac Oncol 6: 1601-1612.
Johns et al., The antitumor monoclonal antibody 806 recognizes a high-mannose form of the EGF receptor that reaches the cell surface when cells over-express the receptor, The FASEB Journal, Mar. 17, 2005, vol. 19, Iss. 7, pp. 1-18.
Kavran, JM, McCabe, JM, Byrne, PO, Connacher, MK, Wang, Z, Ramek, A, et al. (2014). How IGF-1 activates its receptor. Elife 3.
Kiernan, JA (1975). Localization of alpha-D-glucosyl and alpha-D-mannosyl groups of mucosubstances with concanavalin A and horseradish peroxidase. Histochemistry 44: 39-45.
Kjaer, I, Lindsted, T, Frohlich, C, Olsen, JV, Horak, ID, Kragh, M, et al. (2016). Cetuximab Resistance in Squamous Carcinomas of the Upper Aerodigestive Tract is Driven by Receptor Tyrosine Kinase Plasticity: Potential for mAb Mixtures. Mol Cancer Ther 15: 1614-1626.
Laron, Z (2001). Insulin-like growth factor 1 (IGF-1): a growth hormone. Mol Pathol 54: 311-316.
Lengyel, E., "Ovarian cancer development and metastasis," *The American Journal of Pathology*, 177(3): 1053-1064 (2010).
Li, J, Choi, E, Yu, H, and Bai, XC (2019). Structural basis of the activation of type 1 insulin-like growth factor receptor. Nat Commun 10: 4567.
Liu, P, Cleveland, TEt, Bouyain, S, Byrne, PO, Longo, PA, and Leahy, DJ (2012). A single ligand is sufficient to activate EGFR dimers. Proc Natl Acad Sci U S A 109: 10861-10866.
Liu, Q, Guan, JZ, Sun, Y, Le, Z, Zhang, P, Yu, D, et al. (2017). Insulin-like growth factor 1 receptor-mediated cell survival in hypoxia depends on the promotion of autophagy via suppression of the PI3K/Akt/mTOR signaling pathway. Mol Med Rep 15: 2136-2142.
Ludovini, V, Bellezza, G, Pistola, L, Bianconi, F, Di Carlo, L, Sidoni, A, et al. (2009). High coexpression of both insulin-like growth factor receptor-1 (IGFR-1) and epidermal growth factor receptor (EGFR) is associated with shorter disease-free survival in resected non-small-cell lung cancer patients. Ann Oncol 20: 842-849.
Mirza, M.R., et al., "Niraparib maintenance therapy in platinum-sensitive, recurrent ovarian cancer," *New England Journal of Medicine*, 375(22): 2154-2164 (2016).
Moginger, U, Grunewald, S, Hennig, R, Kuo, CW, Schirmeister, F, Voth, H, et al. (2018). Alterations of the Human Skin N- and O-Glycome in Basal Cell Carcinoma and Squamous Cell Carcinoma. Front Oncol 8: 70.
Moore, K., et al., "Maintenance olaparib in patients with newly diagnosed advanced ovarian cancer," *New England Journal of Medicine*, 379(26): 2495-2505 (2018).
Morgillo, F, Kim, WY, Kim, ES, Ciardiello, F, Hong, WK, and Lee, HY (2007). Implication of the insulin-like growth factor-IR pathway in the resistance of non-small cell lung cancer cells to treatment with gefitinib. Clin Cancer Res 13: 2795-2803.
Munkley, J, Mills, IG, and Elliott, DJ (2016). The role of glycans in the development and progression of prostate cancer. Nat Rev Urol 13: 324-333.
Notification of Transmittal of the International Search Report and the Written Opinion of the International Searching Authority, or the Declaration for International Application No. PCT/US2022/012853, "Actinohivin Variant Polypeptides and Related Methods" date of mailing: Apr. 1, 2022.
Notification of Transmittal of the International Search Report and the Written Opinion of the International Searching Authority, or the Declaration for International Application No. PCT/US2022/070961, "Actinohivin Variant Polypeptides and Related Methods" date of mailing: May 12, 2022.
Oh et al., Antitumor activity of a lectibody targeting cancer-associated high-mannose glycans, bioRxiv, Apr. 29, 2021, [retrieved on Mar. 15, 2022], Retrieved from internet: <URL: https://doi.org/10.1101/2021.04.28.441869>.
Park, DD, Phoomak, C, Xu, G, Olney, LP, Tran, KA, Park, SS, et al. (2020). Metastasis of cholangiocarcinoma is promoted by extended high-mannose glycans. Proc Natl Acad Sci U S A 117: 7633-7644.
Pearce, O.M., "Cancer glycan epitopes: biosynthesis, structure and function," *Glycobiology*, 28(9): 670-696 (2018).
Pirker, R, Pereira, JR, Szczesna, A, von Pawel, J, Krzakowski, M, Ramlau, R, et al. (2009). Cetuximab plus chemotherapy in patients with advanced non-small-cell lung cancer (FLEX): an open-label randomised phase III trial. Lancet 373: 1525-1531.
Powers, TW, Holst, S, Wuhrer, M, Mehta, AS, and Drake, RR (2015). Two-Dimensional N-Glycan Distribution Mapping of Hepatocellular Carcinoma Tissues by MALDI-Imaging Mass Spectrometry. Biomolecules 5: 2554-2572.
Pujol, JL, Pirker, R, Lynch, TJ, Butts, CA, Rosell, R, Shepherd, FA, et al. (2014). Meta-analysis of individual patient data from randomized trials of chemotherapy plus cetuximab as first-line treatment for advanced non-small cell lung cancer. Lung Cancer 83: 211-218.
Ruhaak, LR, Taylor, SL, Stroble, C, Nguyen, UT, Parker, EA, Song, T, et al. (2015). Differential N-Glycosylation Patterns in Lung Adenocarcinoma Tissue. J Proteome Res 14: 4538-4549.
Sato et al., High mannose-binding Pseudomonas fluorescens lectin (PFL) downregulates cellsurface integrin/EGFR and induces autophagy in gastric cancer cells, BMC Cancer, Feb. 6, 2016, vol. 16, Iss. 63, pp. 1-13.
Seber Kasinger, LE, Dent, MW, Mahajan, G, Hamorsky, KT, and Matoba, N (2019). A novel anti-HIV-1 bispecific bNAb-lectin fusion protein engineered in a plant-based transient expression system. Plant Biotechnol J.
Sertkaya, A., et al., "Key cost drivers of pharmaceutical clinical trials in the United States," *Clin Trials*, 13(2): 117-26 (2016).
Steiner, P, Joynes, C, Bassi, R, Wang, S, Tonra, JR, Hadari, YR, et al. (2007). Tumor growth inhibition with cetuximab and chemotherapy in non-small cell lung cancer xenografts expressing wild-type and mutated epidermal growth factor receptor. Clin Cancer Res 13: 1540-1551.
Strasser R et al., "Generation of glyco-engineered *Nicotiana benthamiana* for the production of monoclonal antibodies with a homogeneous human-like *N*-glycan structure," *Plant Biotechnology Journal*, 6(4): 392-402 (May 2008).
Takayama, H, Ohta, M, Iwashita, Y, Uchida, H, Shitomi, Y, Yada, K, et al. (2020). Altered glycosylation associated with dedifferentiation of hepatocellular carcinoma: a lectin microarray-based study. BMC Cancer 20: 192.
Van Brummelen, E.M., et al., "Antidrug antibody formation in oncology: clinical relevance and challenges," The Oncologist, 21(10): 1260 (2016).
Wei, H., et al., "Combinatorial PD-1 blockade and CD137 activation has therapeutic efficacy in murine cancer models and synergizes with cisplatin," *PloS One*, 8(12): e84927-e84927 (2013).
Wong, MY, Chen, K, Antonopoulos, A, Kasper, BT, Dewal, MB, Taylor, RJ, et al. (2018). XBP1s activation can globally remodel N-glycan structure distribution patterns. Proc Natl Acad Sci U S A 115: E10089-E10098.
Xu, Q, Malecka, KL, Fink, L, Jordan, EJ, Duffy, E, Kolander, S, et al. (2015). Identifying three-dimensional structures of autophosphorylation complexes in crystals of protein kinases. Sci Signal 8: rs13.
Zhang, X., et al., "Discovery of specific metastasis-related N-glycan alterations in epithelial ovarian cancer based on quantitative glycomics," PLoS One, 9(2): e87978 (2014).

(56) References Cited

OTHER PUBLICATIONS

Zheng, WH, and Quirion, R (2006). Insulin-like growth factor-1 (IGF-1) induces the activation/phosphorylation of Akt kinase and cAMP response element-binding protein (CREB) by activating different signaling pathways in PC12 cells. BMC Neurosci 7: 51.
Zhong, L., et al., "Cost-Effectiveness of Niraparib and Olaparib as Maintenance Therapy for Patients with Platinum-Sensitive Recurrent Ovarian Cancer," *Journal of Managed Care & Specialty Pharmacy*, 24(12): 1219-1228 (2018).
International Preliminary Report on Patentability for International Application No. PCT/US2022/070961, "Actinohivin Variant Polypeptides and Related Methods" date of issuance: Aug. 29, 2023.
BCC Publishing. "Therapies and Diagnostics for Ovarian Cancer: Global Markets to 2022," Available from: www.bccresearch.com/market-research/healthcare/therapies-and-diagnostics-for-ovarian-cancer-report.html (2018).
Chiba H. et al., "Actinohivin, a novel anti-HIV protein from an actinomycete that inhibits syncytium formation: isolation, characterization, and biological activities," Biochem Biophys Res Commun, 282(2):595-601 (Mar. 2001).
Colombo, I., et al., "Immunologic and genomic characterization of high grade serous ovarian cancer (HGSOC) in patients (pts) treated with pembrolizumab (Pembro) in the phase II Inspire trial," American Society of Clinical Oncology (2017).
Lheureux, S., et al., "Epithelial ovarian cancer," The Lancet, 393(10177): 1240-1253 (2019).
Loke, I., et al., "Emerging roles of protein mannosylation in inflammation and infection," Molecular aspects of medicine, 51: 31-55 (2016).
Oliveira-Ferrer, L., K. Legler, and K. Milde-Langosch, "Role of protein glycosylation in cancer metastasis," in Seminars in cancer biology. 2017. Elsevier.
Richardson, D.L., et al., "Antibody Drug Conjugates in the Treatment of Epithelial Ovarian Cancer," Hematology/Oncology Clinics of North America, 32(6): 1057-1071 (2018).
Torre, L.A., et al., Ovarian cancer statistics, 2018. CA: A Cancer Journal for Clinicians, 2018. 68(4): p. 284-296.
Sethi, MK, Hancock, WS, and Fanayan, S (2016). Identifying N-Glycan Biomarkers in Colorectal Cancer by Mass Spectrometry. Acc Chem Res 49: 2099-2106.
Park, HM, Hwang, MP, Kim, YW, Kim, KJ, Jin, JM, Kim, YH, et al. (2015). Mass spectrometry-based N-linked glycomic profiling as a means for tracking pancreatic cancer metastasis. Carbohydr Res 413: 5-11.
Maley, F, Trimble, RB, Tarentino, AL, and Plummer, TH, Jr. (1989). Characterization of glycoproteins and their associated oligosaccharides through the use of endoglycosidases. Anal Biochem 180: 195-204.
Yeo, CD, Park, KH, Park, CK, Lee, SH, Kim, SJ, Yoon, HK, et al. (2015). Expression of insulin-like growth factor 1 receptor (IGF-1R) predicts poor responses to epidermal growth factor receptor (EGFR) tyrosine kinase inhibitors in non-small cell lung cancer patients harboring activating EGFR mutations. Lung Cancer 87: 311-317.
Downward, J, Parker, P, and Waterfield, MD (1984). Autophosphorylation sites on the epidermal growth factor receptor. Nature 311: 483-485.
Gates, RE, and King, LE, Jr. (1985). Different forms of the epidermal growth factor receptor kinase have different autophosphorylation sites. Biochemistry 24: 5209-5215.
Yarden, Y (2001). The EGFR family and its ligands in human cancer. signalling mechanisms and therapeutic opportunities. Eur J Cancer 37 Suppl 4: S3-8.
Pirker, R, Pereira, JR, von Pawel, J, Krzakowski, M, Ramlau, R, Park, K, et al. (2012). EGFR expression as a predictor of survival for first-line chemotherapy plus cetuximab in patients with advanced non-small-cell lung cancer: analysis of data from the phase 3 FLEX study. Lancet Oncol 13: 33-42.
Zhang, G, Isaji, T, Xu, Z, Lu, X, Fukuda, T, and Gu, J (2019). N-acetylglucosaminyltransferase-I as a novel regulator of epithelial-mesenchymal transition. FASEB J 33: 2823-2835.
Hasegawa, Y. et al. (2015) Surfactant protein D suppresses lung cancer progression by downregulation of epidermal growth factor signaling. Oncogene 34, 4285-4286.
Ullrich, A., et al., "Human epidermal growth factor receptor cDNA sequence and aberrant expression of the amplified gene in A431 epidermoid carcinoma cells", Nature 309:418-425, 1984.

| | | | |
|---|---|---|---|
| Actinohivin | 1 | ASVTIRNAQTGRLLDSNYNGNVYTLPANGGNYQRWTGP | 38 |
| | 39 | GDGTVRNAQTGRCLDSNYDGAVYTLPCNGGSYQKWLFY | 76 |
| | 77 | SNGYIQNVETGRVLDSNYNGNVYTLPANGGNYQKWYTG | 114 |
| Variant 1 | 1 | ASGTIRNAETGRLLDSNYDGAVYTLPANGGSYQRWTGP | 38 |
| | 39 | GDGTVRNAETGRLLDSNYDGAVYTLPANGGSYQKWTGP | 76 |
| | 77 | GDGTIQNAETGRLLDSNYDGAVYTLPANGGSYQKW-TG | 114 |
| Variant 2 | 1 | ASGTIRNAETGRCLDSNYDGAVYTLPCNGGSYQRWTGP | 38 |
| | 39 | GDGTVRNAETGRCLDSNYDGAVYTLPCNGGSYQKWTGP | 76 |
| | 77 | GDGTIQNAETGRCLDSNYDGAVYTLPCNGGSYQKW-TG | 114 |
| Variant 3 | 1 | ASVTIRNAETGRLLDSNYNGNVYTLPANGGNYQRWTGP | 38 |
| | 39 | GDGTVRNAETGRCLDSNYDGAVYTLPCNGGSYQKWLFY | 76 |
| | 77 | SNGYIQNVETGRVLDSNYNGNVYTLPANGGNYQKWYTG | 114 |
| Variant 4 | 1 | ASVTIRNAETGRCLDSNYNGNVYTLPCNGGNYQRWTGP | 38 |
| | 39 | GDGTVRNAETGRCLDSNYDGAVYTLPCNGGSYQKWLFY | 76 |
| | 77 | SNGYIQNVETGRCLDSNYNGNVYTLPCNGGNYQKWYTG | 114 |
| Variant 5 | 1 | ASGTIRNAETGRLLDSNYNGNVYTLPANGGNYQRWTGP | 38 |
| | 39 | GDGTVRNAETGRCLDSNYDGAVYTLPCNGGSYQKWTGP | 76 |
| | 77 | GDGTIQNAETGRVLDSNYNGNVYTLPANGGNYQKW-TG | 114 |
| Variant 6 | 1 | ASGTIRNAETGRCLDSNYDGNVYTLPCNGGSYQRWTGP | 38 |
| | 39 | GDGTVRNAETGRCLDSNYDGNVYTLPCNGGSYQKWTGP | 76 |
| | 77 | GDGTIQNAETGRCLDSNYDGNVYTLPCNGGSYQKW-TG | 114 |
| Variant 7 | 1 | ASGTIRNAQTGRCLDSNYNGNVYTLPCNGGNYQRWTGP | 38 |
| | 39 | GDGTVRNAQTGRCLDSNYDGAVYTLPCNGGSYQKWTGP | 76 |
| | 77 | GDGTIQNAETGRCLDSNYNGNVYTLPCNGGNYQKW-TG | 114 |
| Variant 8 | 1 | ASGTIRNAETGRCLDSNYNGNVYTLPCNGGNYQRWTGP | 38 |
| | 39 | GDGTVRNAETGRCLDSNYDGAVYTLPCNGGSYQKWTGP | 76 |
| | 77 | GDGTIQNAETGRCLDSNYNGNVYTLPCNGGNYQKW-TG | 114 |
| Variant 9 | 1 | ASGTIRNAQTGRCLDSNYNGNVYTLPCNGGNYQRWTGP | 38 |
| | 39 | GDGTVRNAETGRCLDSNYDGAVYTLPCNGGSYQKWTGP | 76 |
| | 77 | GDGTIQNAETGRCLDSNYNGNVYTLPCNGGNYQKW-TG | 114 |
| Variant 10 | 1 | ASGTIRNAETGRCLDSNYNGNVYTLPCNGGNYQRWTGP | 38 |
| | 39 | GDGTVRNAQTGRCLDSNYDGAVYTLPCNGGSYQKWTGP | 76 |
| | 77 | GDGTIQNAETGRCLDSNYNGNVYTLPCNGGNYQKW-TG | 114 |
| Variant 11 | 1 | ASGTIRNAQTGRLLDSNYNGNVYTLPANGGNYQRWTGP | 38 |
| | 39 | GDGTVRNAQTGRLLDSNYNGNVYTLPANGGNYQKWTGP | 76 |
| | 77 | GDGTIQNAQTGRVLDSNYNGNVYTLPANGGNYQKW-TG | 114 |
| Variant 12 | 1 | ASGTIRNAETGRLLDSNYNGNVYTLPANGGNYQRWTGP | 38 |
| | 39 | GDGTVRNAETGRLLDSNYNGNVYTLPANGGNYQKWTGP | 76 |
| | 77 | GDGTIQNAETGRVLDSNYNGNVYTLPANGGNYQKW-TG | 114 |
| Variant 13 | 1 | ASGTIRNAETGRCLDSNYNGNVYTLPCNGGNYQRWTGP | 38 |
| | 39 | GDGTVRNAETGRCLDSNYNGNVYTLPCNGGNYQKWTGP | 76 |
| | 77 | GDGTIQNAETGRCLDSNYNGNVYTLPCNGGNYQKW-TG | 114 |
| Variant 14 | 1 | ASGTIRNAETGRCLDSNYDGNVYTLPCNGGNYQRWTGP | 38 |
| | 39 | GDGTVRNAETGRCLDSNYDGNVYTLPCNGGNYQKWTGP | 76 |
| | 77 | GDGTIQNAETGRCLDSNYDGNVYTLPCNGGNYQKW-TG | 114 |

FIG. 4A

FIG. 11A
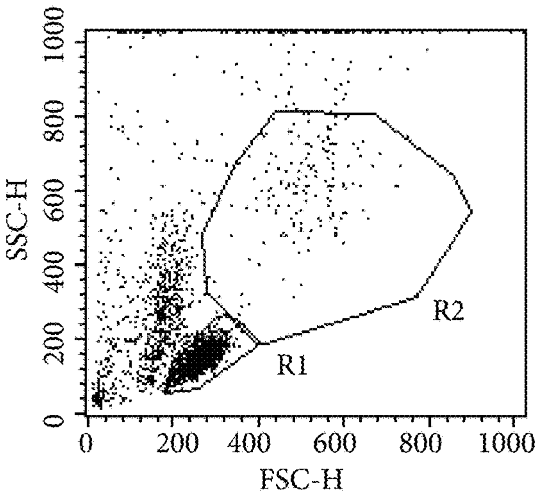
FIG. 11B
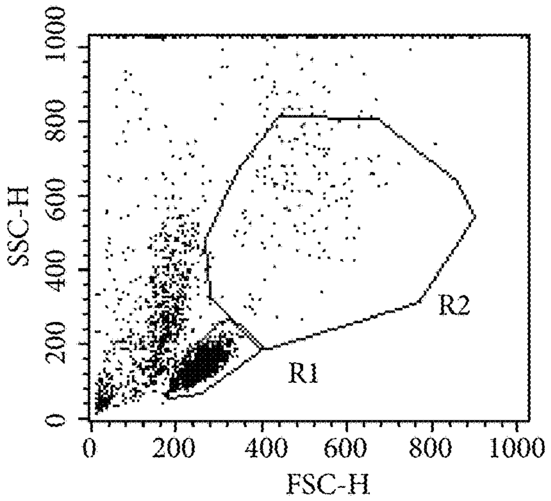
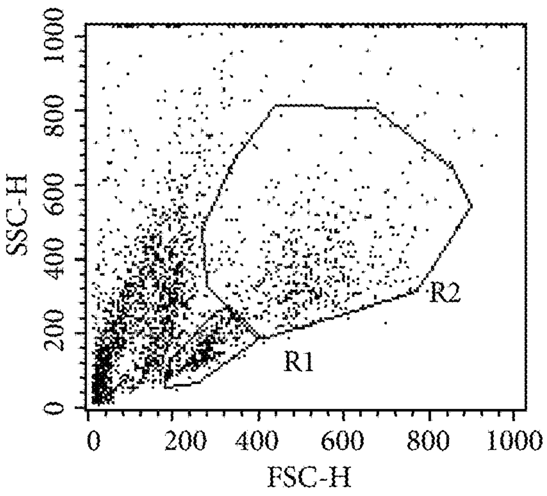
FIG. 11C
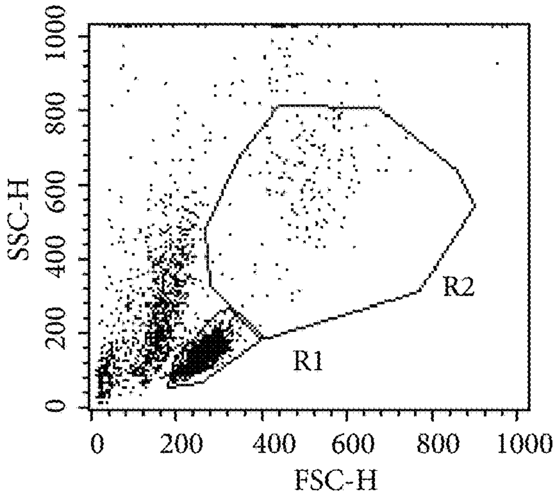
FIG. 11D

ACTINOHIVIN VARIANT POLYPEPTIDES AND METHODS OF TREATMENT USING THEM

RELATED APPLICATIONS

This application is the U.S. National Stage of International Application No. PCT/US2018/017617, filed Feb. 9, 2018, which designates the U.S., published in English, and claims the benefit of U.S. Provisional Application No. 62/457,308, filed Feb. 10, 2017. The entire teachings of the above applications are incorporated herein by reference.

GOVERNMENT INTEREST

This invention was made with government support under grant number DoD/USAMRMC W81XWH-10-2-0082-CLIN 2 awarded by the U.S. Department of Defense, and grant number NIH/NIAID AI088585 awarded by the National Institutes of Health. The government has certain rights in the invention.

INCORPORATION BY REFERENCE OF MATERIAL IN ASCII TEXT FILE

This application incorporates by reference the Sequence Listing contained in the following ASCII text file:

a) File name: 56001002001_SEQUENCE_LISTING.txt; created Aug. 9, 2019, 20 KB in size.

TECHNICAL FIELD

The presently-disclosed subject matter generally relates to actinohivin variant polypeptides and related methods. In particular, certain embodiments of the presently-disclosed subject matter relate to actinohivin variant polypeptides and methods of using those actinohivin variant polypeptides to treat a viral infection or a cancer.

BACKGROUND

High-mannose-type glycans (HMGs) are often clustered on the envelope glycoproteins of HIV and other enveloped viruses. These glycans are also elevated in malignant cell glycocalyx and cancer patient sera. In human and other eukaryotic cells, HMGs appear in the early-stage N-glycosylation of nascent polypeptides within the endoplasmic reticulum. These “immature” oligosaccharides are subsequently processed into more complex glycoforms during protein secretion through the Golgi apparatus before they reach the cell membrane. Hence, HMGs are rare in the extracellular environment under normal conditions, and conversely, high levels of HMGs displayed on enveloped viruses and cancer cells provide a unique biomarker for drug development.

Carbohydrate-binding proteins, or lectins, are widely found in animals, plants, and microorganisms, playing critical roles in diverse biological processes, such as cellular signaling, microbe-host interactions and host defense. In biomedical research, several lectins of heterologous origins have shown immunomodulatory, anti-tumor, anti-microbial and anti-viral effects, highlighting their potential use as drugs. Actinohivin (AH) is an actinomycete-derived lectin specific to HMGs. It exhibits anti-HIV activity without cytotoxicity or mitogenicity in human blood cells. A drawback, however, is that AH is hydrophobic, prone to aggregate and thus recalcitrant to efficient recombinant production, hampering its antiviral drug development. Accordingly, AH compositions that overcome the foregoing limitations would be both highly desirable and beneficial.

SUMMARY

The presently-disclosed subject matter meets some or all of the above-identified needs, as will become evident to those of ordinary skill in the art after a study of information provided in this document.

This summary describes several embodiments of the presently-disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this summary or not. To avoid excessive repetition, this summary does not list or suggest all possible combinations of such features.

The presently-disclosed subject matter includes actinohivin variant polypeptides and related methods. In particular, certain embodiments of the presently-disclosed subject matter include actinohivin variant polypeptides as well as methods of using those actinohivin variant polypeptides to treat a viral infection or a cancer.

In some embodiments of the presently-disclosed subject matter, a polypeptide is provided that comprises an actinohivin variant polypeptide. In some embodiments, the actinohivin variant polypeptide is selected from the group consisting of SEQ ID NOS: 2-13. In some embodiments, the actinohivin variant polypeptide comprises SEQ ID NO: 9.

In some embodiments of the presently-described polypeptides, an actinohivin variant polypeptide is provided that is directed fused (e.g., via a linking polypeptide) or is otherwise operably connected to an antibody fragment which, in some embodiments, increases the therapeutic effectiveness of the polypeptides. In some embodiments, the antibody fragment comprises a fragment crystallizable (Fc) region of immunoglobulin (Ig) G. In some embodiments, a polypeptide is provided that comprises an actinohivin variant polypeptide of the presently-disclosed subject matter fused to an Fc region of IgG, such as the polypeptide of SEQ ID NO: 16. In some embodiments, a pharmaceutical composition is provided that comprises a polypeptide of the presently-disclosed subject matter and a pharmaceutically-acceptable vehicle, carrier, or excipient.

Further provided, in some embodiments, are isolated nucleic acids comprising a nucleic acid sequence encoding an actinohivin variant polypeptide of the presently-disclosed subject matter. In some embodiments, the nucleic acids are incorporated into an appropriate expression vector for expressing the polypeptides of the presently-disclosed subject matter in a desired cell, such as, in some embodiments, a eukaryotic cell. For example, in some embodiments, the desired cell is a plant cell transfected with the vectors, or a progeny of the plant cell, where the cell or the progeny of the cell expresses the polypeptide. In some embodiments, the nucleic acids incorporated into the vectors are operably linked to an expression cassette.

Still further provided, in some embodiments of the presently-disclosed subject matter, are methods of treating a viral infection or a cancer. In some embodiments, a method of treating a viral infection is provided that comprises administering an actinohivin variant polypeptide of the presently-disclosed subject matter to a subject in need thereof. In some embodiments, the viral infection is a human immunodeficiency virus (HIV) infection. In some embodiments, a method of treating a cancer is provided that comprises administering an actinohivin variant polypeptide of the presently-disclosed subject matter to a subject in need thereof. In some embodiments, the cancer is selected from lung cancer, breast cancer, colon cancer, blood cancer, cervical cancer, and prostate cancer. In some embodiments, the cancer treated with the presently-disclosed polypeptides is characterized by one or more cancer cells having high-mannose-type glycans on a cell membrane of the one or more cancer cells.

Further features and advantages of the presently-disclosed subject matter will become evident to those of ordinary skill in the art after a study of the description, figures, and non-limiting examples in this document.

BRIEF DESCRIPTION OF THE DRAWINGS

(FIG. 1A) a graph showing the screening of AH variants (amino acid sequences in FIG. 4) accumulated in *N. benthamiana* leaf tissue by ELISA, where variant 8 (SEQ ID NO: 9) was designated Avaren; (FIG. 1B) graphs showing circular dichroism (CD) analysis with far-UV CD spectra of AH and Avaren (upper panel) and near-UV CD spectra of AH and Avaren. (lower panel); (FIG. 1C) a schematic diagram showing the crystal structure of AH (PDB ID: 4G1R) superimposed with a homology model of Avaren, shown from the top (top) and side (bottom) views (PyMOL software), where homology modeling was performed using SWISS-MODEL using AH as a template, and where the zoomed images of the surface exposed loop between Domains 2 and 3 (amino acids 74-80) are boxed; (FIG. 1D) images showing the expression and purification of AvFc, where reducing and non-reducing sodium dodecyl sulfate polyacrylamide gel electrophoresis (SDS-PAGE) was performed to analyze crude leaf extracts and purified AvFc, stained with Coomassie Brilliant Blue (Lane 1: Non-infiltrated leaf extract, Lane 2: Empty vector infiltrated leaf extract, Lane 3: AvFc expressing leaf extract, Lane 4: 10 μg of purified AvFc); (FIG. 1E) graphs showing glycan array analysis, where sugar binding profiles of AH (top) and AvFc (bottom) were analyzed in a mammalian glycan array with 610 glycans by Consortium for Functional Glycomics, and where glycans with a mean relative fluorescence unit exceeding 3,000 were ranked and shown with schematic diagrams (green circle: mannose; blue square: N-acetylglucosamine); (FIG. 1F) graphs showing surface plasmon resonance (SPR) showing the binding affinity ($K_D$; mean±SEM of duplicate analysis) of AH (top) and AvFc (bottom), to $gp120_{SF162}$; and (FIG. 1G) graphs showing HIV-neutralizing activity of AH, AvFc and the CD4 binding site-specific broadly neutralizing human monoclonal antibody VRC01, where a representative graph of two independent assays is shown.

(FIG. 2A) a graph showing human PBMC-based primary HIV neutralization assay, where horizontal bars represent median IC50s (2.00 μg/mL and 0.02 μg/mL for AH and AvFc, respectively), where each assay was done in quadruplicate, and where wilcoxon matched-pairs signed rank test (GraphPad Prism 5) was used to analyze the differences; (FIG. 2B) a graph showing the anti-HIV activity of AvFc and N200Q-AvFc in human PBMCs infected by the primary BaL strain, where infection of human PBMC by the primary isolate BaL was used to assess the contribution of Fc-mediated functions to the overall antiviral activity, and where data shown is a representative of two independent experiments, with each done in triplicate (expressed as mean±SEM); (FIG. 2C) a graphs showing ADCVI activity of AvFc and VRC01, where $CD4^+$ lymphocytes were infected with HIV-$1_{92US657}$ at a multiplicity of infection of approximately 0.05 for 72 hr prior to the addition of AvFc (solid line) or VRC01 (broken line) and natural killer effector cells at an effector/target cell (E:T) ration of 2:1, and where data shown is a representative of three independent experiments, with each done in triplicate (expressed as mean±SEM); (FIG. 2D) a schematic diagram showing results of flow cytometry analysis of AvFc binding to various human cells, where the percentages of FITC positive cells are shown as a heatmap; (FIG. 2E) images showing immunocytochemistry assessing the non-tumorigenic mammary epithelial cell line MCF10A and non-small cell lung carcinoma cell line H460 with 1 μg/mL AvFc, where samples were analyzed by fluorescent microscopy (63×); (FIG. 2F) PET/CT (image "A") and CT (image "B") of $^{64}$Cu-AvFc in B16F10 tumor-bearing C57 mouse, where the PET/CT image clearly shows that the $^{64}$Cu-AvFc accumulated in the B16F10 tumor at 24 hrs post i.v. injection, where the tumor is indicated by the white arrow, and where the accumulation of the tracer is also evident in the liver, suggesting the hepatic clearance of the radiolabeled lectibody; and (FIG. 2G) images showing immunohistochemistry staining of formalin-fixed paraffin embedded human colon tissue sections, where immunohistochemistry was performed on a colon tissue array (US Biomax, Rockville, MD), where tissue sections were incubated with 10 μg/ml AvFc and detected with the anti-Avaren monoclonal antibody 3A7F9, and where tissues were then counterstained with hematoxylin, dehydrated, and analyzed by Aperio Image Scope and software.

(FIG. 3A) a graph showing Human PBMC viability assessed by flow cytometry after staining with propidium iodide (PI); (FIGS. 3B-3D) graphs showing an analysis of PBMC activation, where PBMCs were treated with a vehicle control, ConA or AvFc and analyzed for CD25 (FIG. 3B), CD69 (FIG. 3C) and HLA-DR (FIG. 3D) after dual fluorescent staining; (FIG. 3E) a graph showing cytokine and chemokine secretion by PBMCs stimulated with AvFc or ConA, and assessed by a multiplex bead array; (FIG. 3F) a graph showing pharmacokinetic evaluation of Avaren and AvFc, where serum Avaren and AvFc concentrations were measured by specific immunoassays at different time points after single bolus dose administration via the tail vein, and where data represent mean±SEM obtained for each group (n=4) and half-life values were derived using nonlinear regression (curve fitting) in GraphPad Prism software; (FIGS. 3G-3I) graphs showing the effects of AvFc repeated systemic dosing on body weight (FIG. 3G), blood chemistry (FIG. 3H) and complete blood count (FIG. 3I) in mice (n=10), where blood chemistry and complete blood count data were analyzed one day after the last dose in the mouse repeated dosing study, where values are relative to the vehicle control group (mean±SEM), where actual measured values are shown in Tables 2 and 3, where AvFc showed significantly lower BUN (blood urea nitrogen) and CA (calcium) levels than the vehicle control (*$P<0.05$; one-way ANOVA with Bonferroni's posttests); however, these values remained within the normal range for mice (10-33 mg/dL for BUN and 8.0-15.5 mg/dL for CA according to the University of Louisville Pathology Laboratory).

FIGS. 4A-4C include schematic diagrams, images, and graphs showing AH and AH variants, including: (FIG. 4A) a schematic diagram showing the amino acid sequences of AH and AH mutants, where the three domains of AH (aa 1-38, 39-76, and 77-114) are aligned, where shaded areas indicate conserved residues among the three modules, and where the mutant, Avaren, is variant 8 (SEQ ID NO:9); (FIG. 4B) an image of a sodium dodecyl sulfate polyacrylamide gel electrophoresis performed to analyze crude extracts of *N. benthamiana* leaves expressing AH or its variants and stained with Coomassie Brilliant Blue, where, at 5 dpi, leaf proteins were extracted with PBS (pH 7.2) containing 40 mM ascorbic acid using a 3:1 buffer to leaf ratio (NI: Non-infiltrated leaf extract, EV: Empty vector infiltrated leaf extract, AH: AH expressing leaf extract, Lane 1-14: Leaf extracts of AH variants); (FIG. 4C) a graph showing analysis of the anti-HIV activity of AH variants in crude leaf extracts, where a syncytium formation assay was utilized to assess the anti-HIV activity of crude leaf extracts from plants expressing AH variants that showed a positive signal in gp120-ELISA in FIG. 1A (i.e., Variants 2, 3, 5, 6, 7, 8, 9, 10, 13 and 14), where a 1/20 final dilution of extract was mixed with HL2/3 cells expressing HIV gp120 and TZM-b1 $CD4^+$ cells and incubated for 18 h, and where % inhibition was reflected by the reduction in β-galactosidase activity based on HL2/3 plus TZM-b1 cells only control.

(FIGS. 9A-9B) graphs showing surface plasmon resonance, where the binding affinity ($K_D$) of recombinant human FcγRI (FIG. 9A) and FcγRIIIa (FIG. 9B) to AvFc was measured using a Biacore X100 2.0 instrument, where representative sensorgrams obtained with AvFc are shown, where, in the FcγRI sensorgram, the raw (colored lines) and fitted (black lines) curves represent FcγRI concentrations (1.2, 0.4, 0.13, 0.044, and 0.015 μg/ml from top to bottom), where the $K_D$ was determined to be 0.0715±0.0219 nM based on 1:1 binding kinetics, where, in the FcγRIIIa sensorgram, the raw data curves (colored lines) represent FcγRIIIa concentrations (100, 33.3, 11.1, 3.7, 1.2 and 0.41 μg/ml from top to bottom), where the $K_D$ was determined to be 0.282±0.0035 μM based on steady state (inset), and where the data are expressed as mean±SEM of experimental duplicate analysis; (FIGS. 9C-9D) graphs showing flow cytometry results, where FcγR binding of AvFc was analyzed on a BD FACSAria flow cytometer, where human FcγRI (FIG. 9C) and FcγRIIIA (FIG. 9D) were expressed on the surface of TZM-b1 cells were incubated with either human IgG1κ isotype control, AvFc, or Asn200→Gln AvFc mutant (N200Q-AvFc), where representative histograms are shown depicting % binding compared to cell only controls, where cells were incubated with secondary antibody only (inset: Bar graph showing statistical differences of FcγR binding based on one-way analysis of variance (ANOVA) followed by Bonferroni's post-test; *P<0.001 and ns, not significant (GraphPad Prism5)); (FIG. 9**E) a graph showing surface plasmon resonance analysis of AvFc's binding to FcRn, where the binding affinity ($K_D$) of AvFc to FcRn was measured using a Biacore X100 2.0 instrument, where the assay was performed in duplicate and a representative sensorgram is shown, where AvFc was captured on a gp$120_{CM}$ immobilized CM5 chip to a surface density of about 120 RUs, where three fold serial dilutions of recombinant human FcRn (5 μg/ml to 0.0617 μg/ml) were prepared in running buffer (HPS-P+) and injected, at a flow rate of 5 μl/min, where the equilibrium dissociation constant, $K_D$, was determined to be 60.1±2.2 nM based on steady state (inset), and where data are expressed as mean±SEM of two independent analyses.

(FIG. 10A) a graph showing the results of an experiment where A549 breast cancer cells were incubated with AvFc (1 μg/ml) and various concentrations of gp120 and mannan for 30 minutes at 4° C., where cells were washed and stained with 10 μg/ml of goat anti-human IgG FITC for 30 minutes at 4° C., where cells were then washed and analyzed for binding on a FACS Canto II (BD Biosciences) using FACSDiva (BD Biosciences); (FIG. 10B) a graph showing human PBMC-based ADCC assay using A549 lung cancer cells, where cells were pre-incubated with serial dilutions of AvFc or Erbitux (cetuximab) for 30 min in a 37° C./5% $CO_2$ incubator, where PBMCs were added to initiate the ADCC effects at an optimized effector/target ratio (50:1 for AvFc, 25:1 for Erbitux) where, after incubation in a 37° C./5% $CO_2$ incubator for 6 h, cell supernatants were collected for measuring released lactose dehydrogenase to calculate % target cell lysis, and where the experiment was done in triplicates, with mean±SEM shown for each data point; and (FIG. 10C) graphs showing ADCC assays, where A549, MCF7 and RKO cells were co-cultured with Jurkat/FcγRIIIa/NFAT-Luc reporter cells in the presence of varying concentrations of AvFc, N200Q-AvFc, cetuximab or trastuzumab, where N200Q-AvFc has significantly reduced FcγR binding affinities, were target cells were co-cultured with the effector cells at a 15:1 ratio, where, after 24 hours cells were lysed, and firefly luciferase activity was measured as relative luminescence units (RLU), and where each data point represents mean±SEM of triplicate analysis.

FIGS. 11A-11E are graphs showing mitogenic activity of AvFc on PBMC as evaluated by flow-cytometry, where cells were treated with 100 μg/ml AvFc (FIG. 11A), 30 μg/ml AvFc (FIG. 11B), 10 μg/ml ConA (FIG. 11C), and buffer (FIG. 11D) for three days, and analyzed flow-cytometrically, where typical live PBMC were gated in region R1, and a subpopulation with increased size and higher SSC was gated in region R2, and where quantitation of cells in these regions is shown in FIG. 11E (***P<0.001; one-way ANOVA with Bonferroni's posttests).

(FIG. 12E) confirmation of the multiplex bead array results by individual cytokine ELISA, where treatment of PBMCs with 100 μg/ml AvFc resulted in IL-1b, IL-6, and IL-8 levels similar to those obtained with the buffer (n.d. (levels below detection). *P<0.001; one-way ANOVA with Bonferroni's posttests).

FIG. 13A shows major organ weights of buffer control, 5 mg/kg AvFc and 20 mg/kg AvFc groups (mean±SEM). *P<0.05; one-way ANOVA with Bonferroni's posttests, and FIG. 13B shows representative photographs showing hematoxilin and eosin-stained liver and spleen tissue sections from buffer and 20 mg/kg AvFc groups.

BRIEF DESCRIPTION OF THE SEQUENCE LISTING

Figure 1A:
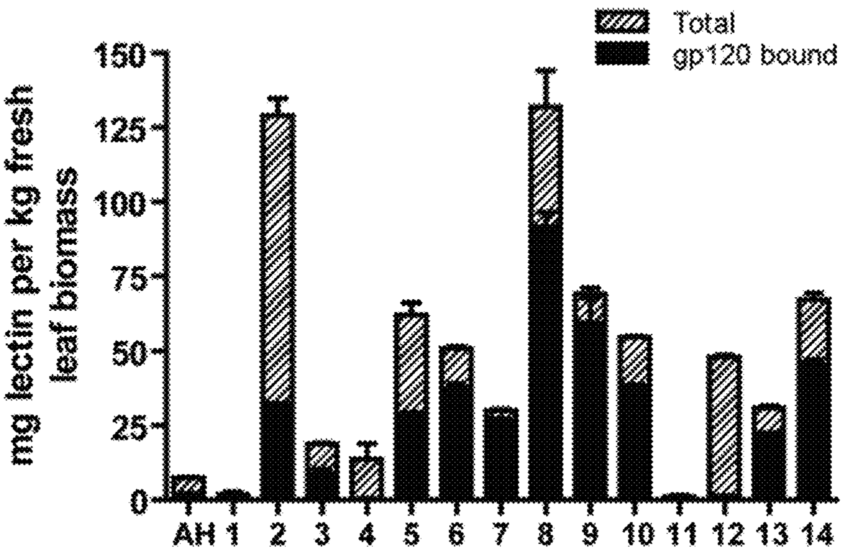
FIGS. 1A-1G include schematic diagrams, images, and graphs, showing the molecular engineering and characterization of an actinohivin variant polypeptide (SEQ ID NO: 9, "Avaren" or actinohivin variant expressed in *Nicotiana*) and of an actinohivin variant polypeptide fused to a fragment crystallizable (Fc) region of immunoglobulin (Ig) G (SEQ ID NO: 16, "AvFc") including.

SEQ ID NO: 1 is an amino acid sequence of a wild type actinohivin polypeptide.

SEQ ID NO: 2 is an amino acid sequence of an actinohivin variant polypeptide made in accordance with the presently-disclosed subject matter and designated herein as variant 1.

SEQ ID NO: 3 is an amino acid sequence of another actinohivin variant polypeptide made in accordance with the presently-disclosed subject matter and designated herein as variant 2.

SEQ ID NO: 4 is an amino acid sequence of another actinohivin variant polypeptide made in accordance with the presently-disclosed subject matter and designated herein as variant 3.

SEQ ID NO: 5 is an amino acid sequence of another actinohivin variant polypeptide made in accordance with the presently-disclosed subject matter and designated herein as variant 4.

SEQ ID NO: 6 is an amino acid sequence of another actinohivin variant polypeptide made in accordance with the presently-disclosed subject matter and designated herein as variant 5.

SEQ ID NO: 7 is an amino acid sequence of another actinohivin variant polypeptide made in accordance with the presently-disclosed subject matter and designated herein as variant 6.

SEQ ID NO: 8 is an amino acid sequence of another actinohivin variant polypeptide made in accordance with the presently-disclosed subject matter and designated herein as variant 7.

SEQ ID NO: 9 is an amino acid sequence of another actinohivin variant polypeptide made in accordance with the presently-disclosed subject matter and designated herein as variant 8 or Avaren (actinohivin variant expressed in *Nicotiana*).

SEQ ID NO: 10 is an amino acid sequence of another actinohivin variant polypeptide made in accordance with the presently-disclosed subject matter and designated herein as variant 9.

SEQ ID NO: 11 is an amino acid sequence of another actinohivin variant polypeptide made in accordance with the presently-disclosed subject matter and designated herein as variant 10.

SEQ ID NO: 12 is an amino acid sequence of another actinohivin variant polypeptide made in accordance with the presently-disclosed subject matter and designated herein as variant 11.

SEQ ID NO: 13 is an amino acid sequence of another actinohivin variant polypeptide made in accordance with the presently-disclosed subject matter and designated herein as variant 12.

SEQ ID NO: 14 is an amino acid sequence of another actinohivin variant polypeptide made in accordance with the presently-disclosed subject matter and designated herein as variant 13.

SEQ ID NO: 15 is an amino acid sequence of another actinohivin variant polypeptide made in accordance with the presently-disclosed subject matter and designated herein as variant 14.

SEQ ID NO: 16 is an amino acid sequence including the actinohivin variant polypeptide of SEQ ID NO: 9 (Variant 8) fused, via a linker polypeptide, to an amino acid sequence comprising the fragment crystallizable (Fc) region of immunoglobulin (Ig) G, and referred to herein as AvFc.

DESCRIPTION OF EXEMPLARY EMBODIMENTS

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by those of ordinary skill in the art, certain definitions are set forth to facilitate explanation of the presently-disclosed subject matter.

Unless defined otherwise, all technical and scientific terms used herein have the same meaning as is commonly understood by one of skill in the art to which the invention(s) belongs.

All patents, patent applications, published applications and publications, GenBank sequences, databases, websites and other published materials referred to throughout the entire disclosure herein, unless noted otherwise, are incorporated by reference in their entirety.

Where reference is made to a URL or other such identifier or address, it understood that such identifiers can change and particular information on the internet can come and go, but equivalent information can be found by searching the internet. Reference thereto evidences the availability and public dissemination of such information.

As used herein, the abbreviations for any protective groups, amino acids and other compounds, are, unless indicated otherwise, in accord with their common usage, recognized abbreviations, or the IUPAC-IUB Commission on Biochemical Nomenclature (see, Biochem. (1972) 11(9): 1726-1732).

Although any methods, devices, and materials similar or equivalent to those described herein can be used in the practice or testing of the presently-disclosed subject matter, representative methods, devices, and materials are described herein.

The present application can "comprise" (open ended), "consist" (closed), or "consist essentially of" the components of the present invention as well as other ingredients or elements described herein. As used herein, "comprising" is open ended and means the elements recited, or their equivalent in structure or function, plus any other element or elements which are not recited. The terms "having" and "including" are also to be construed as open ended unless the context suggests otherwise.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, "optional" or "optionally" means that the subsequently described event or circumstance does or does not occur and that the description includes instances where said event or circumstance occurs and instances where it does not. For example, an optionally variant portion means that the portion is variant or non-variant The presently-disclosed subject matter is based, at least in part, on the development of a novel lectibody (i.e., a polypeptide including a lectin or a portion thereof and an antibody or fragment thereof). In some embodiments, the developed lectibody consists of a novel HMG-specific lectin, referred to herein as an actinohivin variant polypeptide. In some embodiments, the actinohivin variant polypeptide has an amino acid sequence selected from those included in the group consisting of SEQ ID NOS: 2-13. In some embodiments, the actinohivin variant polypeptide has or is comprised of the amino acid sequence of SEQ ID NO: 9, which, in some embodiments, is referred to herein as Avaren.

The terms "polypeptide," "protein," and "peptide," which are used interchangeably herein, refer to a polymer of the 20 protein amino acids, or amino acid analogs, regardless of its size or function. Although "protein" is often used in reference to relatively large polypeptides, and "peptide" is often used in reference to small polypeptides, usage of these terms in the art overlaps and varies. The term "polypeptide" as used herein refers to peptides, polypeptides, and proteins, unless otherwise noted. The terms "protein," "polypeptide," and "peptide" are used interchangeably herein when referring to a gene product. Thus, exemplary polypeptides include gene products, naturally occurring or native proteins, homologs, orthologs, paralogs, fragments and other equivalents, variants, and analogs of the foregoing. The term "native," when used with reference to a polypeptide, refers to a polypeptide that is encoded by a gene that is naturally present in the genome of an untransformed cell.

The terms "polypeptide fragment" or "fragment," when used in reference to a reference polypeptide, refers to a polypeptide in which amino acid residues are deleted as compared to the reference polypeptide itself, but where the remaining amino acid sequence is usually identical to the corresponding positions in the reference polypeptide. Such deletions can occur at the amino-terminus or carboxy-terminus of the reference polypeptide, or alternatively both.

A fragment can also be a "functional fragment," in which case the fragment retains some or all of the activity of the reference polypeptide as described herein. For example, in some embodiments, a functional fragment of an actinohivin polypeptide can refer to a polypeptide in which amino acid residues have been deleted as compared to the full-length actinohivin polypeptide, but which retains some or all of the ability of the full-length actinohivin polypeptide to bind to bind to a carbohydrate, such as a high-mannose-type glycan (HMGs).

The terms "modified amino acid," "modified polypeptide," and "variant" are used herein to refer to an amino acid sequence that is different from the reference polypeptide by one or more amino acids, e.g., one or more amino acid substitutions or additions. A variant of a reference polypeptide also refers to a variant of a fragment of the reference polypeptide, for example, a fragment wherein one or more amino acid substitutions have been made relative to the reference polypeptide. A variant can also be a "functional variant," in which the variant retains some or all of the activity of the reference protein as described herein. For example, in some embodiments, the actinohivin variant polypeptides described herein and shown in SEQ ID NOS: 2-13 include amino acid sequences in which one or more amino acids have been added, deleted, and/or replaced, but which nonetheless retain and/or enhance some or all of the ability of the full-length actinohivin polypeptide (e.g., SEQ ID NO: 1) to bind to bind to a carbohydrate, such as a high-mannose-type glycan (HMGs).

In some embodiments of the presently-disclosed subject matter, an actinohivin variant polypeptide is provided in which the actinohivin variant polypeptide is fused or otherwise linked to a an antibody fragment. As used herein, the term "antibody" when used in relation to an antibody fragment can be used to refer to fragments from a number of different antibodies including, but not limited to, monoclonal antibodies, recombinant antibodies, chimeric antibodies, humanized antibodies, bispecific antibodies, catalytic antibodies, single chain antibodies, antibodies from different species (e.g., mouse, goat, rabbit, human, rat, bovine, llama, etc.), anti-idiotypic antibodies, antibodies of different isotype (IgG, IgM, IgE, IgA, etc.), as well as many fragments of those antibodies (e.g., $(Fab)_2$, Fab, Fv, Fab, 2(Fab), Fab', $(Fab')_2$, or Fc fragments). In some embodiments, the antibody has an IgG isotype, while, in other embodiments, the antibody has an IgA isotype. In some embodiments, the antibody fragment comprises a fragment crystallizable (Fc) region of immunoglobulin (Ig) G.

In some embodiments of the presently-disclosed subject matter, a polypeptide is provided that comprises an actinohivin variant polypeptide of the presently-disclosed subject matter fused to a Fc region of IgG. In some embodiments, the actinohivin variant polypeptide of SEQ ID NO: 9 is fused to a Fc region of IgG via a linking peptide. In some embodiments, such a polypeptide or lectibody comprises the sequence of SEQ ID NO: 16.

Further provided, in some embodiments of the presently-disclosed subject matter are pharmaceutical compositions. In some embodiments, a pharmaceutical composition is provided that comprises an actinohivin variant polypeptide or lectibody of the presently-disclosed subject matter and a pharmaceutically-acceptable vehicle, carrier, or excipient.

With regard to the pharmaceutically-acceptable vehicle, carrier, or excipient suitable for use with the polypeptides of the presently-disclosed subject matter, solid formulations of the compositions for oral administration can contain suitable carriers or excipients, such as corn starch, gelatin, lactose, acacia, sucrose, microcrystalline cellulose, kaolin, mannitol, dicalcium phosphate, calcium carbonate, sodium chloride, or alginic acid. Disintegrators that can be used include, but are not limited to, microcrystalline cellulose, corn starch, sodium starch glycolate, and alginic acid. Tablet binders that can be used include acacia, methylcellulose, sodium carboxymethylcellulose, polyvinylpyrrolidone, hydroxypropyl methylcellulose, sucrose, starch, and ethylcellulose. Lubricants that can be used include magnesium stearates, stearic acid, silicone fluid, talc, waxes, oils, and colloidal silica. Further, the solid formulations can be uncoated or they can be coated by known techniques to delay disintegration and absorption in the gastrointestinal tract and thereby provide a sustained/extended action over a longer period of time. For example, glyceryl monostearate or glyceryl distearate can be employed to provide a sustained-/extended-release formulation. Numerous techniques for formulating sustained release preparations are known to those of ordinary skill in the art and can be used in accordance with the present invention, including the techniques described in the following references: U.S. Pat. Nos. 4,891,223; 6,004,582; 5,397,574; 5,419,917; 5,458,005; 5,458,887; 5,458,888; 5,472,708; 6,106,862; 6,103,263; 6,099,862; 6,099,859; 6,096,340; 6,077,541; 5,916,595; 5,837,379; 5,834,023; 5,885,616; 5,456,921; 5,603,956; 5,512,297; 5,399,362; 5,399,359; 5,399,358; 5,725,883; 5,773,025; 6,110,498; 5,952,004; 5,912,013; 5,897,876; 5,824,638; 5,464,633; 5,422,123; and 4,839,177; and WO 98/47491, each of which is incorporated herein by this reference.

Furthermore, liquid formulations of the compositions for oral administration can be prepared in water or other aqueous vehicles, and can contain various suspending agents such as methylcellulose, alginates, tragacanth, pectin, kelgin, carrageenan, acacia, polyvinylpyrrolidone, and include solutions, emulsions, syrups, and elixirs containing, together with the active components of the composition, wetting agents, sweeteners, and coloring and flavoring agents.

Various liquid and powder formulations can also be prepared by conventional methods for inhalation into the lungs of the subject to be treated. For example, the compositions can be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. Capsules and cartridges of, for example, gelatin for use in an inhaler or insufflator may be formulated containing a powder mix of the desired compound and a suitable powder base such as lactose or starch.

Injectable formulations of the compositions can contain various carriers such as vegetable oils, dimethylacetamide, dimethylformamide, ethyl lactate, ethyl carbonate, isopropyl myristate, ethanol, polyols (glycerol, propylene glycol, liquid polyethylene glycol), and the like. For intravenous injections, water soluble versions of the compositions can be administered by the drip method, whereby a formulation including a pharmaceutical composition of the presently-disclosed subject matter and a physiologically-acceptable excipient is infused. Physiologically-acceptable excipients can include, for example, 5% dextrose, 0.9% saline, Ringer's solution or other suitable excipients. Intramuscular preparations, e.g., a sterile formulation of a suitable soluble salt form of the compositions, can be dissolved and administered in a pharmaceutical excipient such as Water-for-Injection, 0.9% saline, or 5% glucose solution. A suitable insoluble form of the compositions can be prepared and administered as a suspension in an aqueous base or a pharmaceutically-acceptable oil base, such as an ester of a long chain fatty acid, (e.g., ethyl oleate).

In addition to the formulations described above, the compositions of the presently-disclosed subject matter can also be formulated as rectal compositions, such as suppositories or retention enemas, e.g., containing conventional suppository bases such as cocoa butter or other glycerides. Further, the compositions can also be formulated as a depot preparation by combining the compositions with suitable polymeric or hydrophobic materials (for example as an emulsion in an acceptable oil) or ion exchange resins, or as sparingly soluble derivatives, for example, as a sparingly soluble salt.

In some embodiments of the presently-disclosed subject matter, the compositions of the present invention may be incorporated as part of a nanoparticle. A "nanoparticle" within the scope of the presently-disclosed subject matter is meant to include particles at the single molecule level as well as those aggregates of particles that exhibit microscopic properties. Methods of using and making a nanoparticle that incorporates a compound of interest are known to those of ordinary skill in the art and can be found following references: U.S. Pat. Nos. 6,395,253, 6,387,329, 6,383,500, 6,361,944, 6,350,515, 6,333,051, 6,323,989, 6,316,029, 6,312,731, 6,306,610, 6,288,040, 6,272,262, 6,268,222, 6,265,546, 6,262,129, 6,262,032, 6,248,724, 6,217,912, 6,217,901, 6,217,864, 6,214,560, 6,187,559, 6,180,415, 6,159,445, 6,149,868, 6,121,005, 6,086,881, 6,007,845, 6,002,817, 5,985,353, 5,981,467, 5,962,566, 5,925,564, 5,904,936, 5,856,435, 5,792,751, 5,789,375, 5,770,580, 5,756,264, 5,705,585, 5,702,727, and 5,686,113, each of which is incorporated herein by this reference.

A topical formulation (e.g., a semi-solid ointment formulation) can also be provided and can contain a desired concentration of the active ingredient (e.g., a polypeptide of the presently-disclosed subject matter) in a carrier such as a pharmaceutical cream base. Various formulations for topical use include drops, tinctures, lotions, creams, solutions, and ointments containing the active ingredient and various supports and vehicles. The optimal percentage of the therapeutic agent in each pharmaceutical formulation varies according to the formulation itself and the therapeutic effect desired in the specific pathologies and correlated therapeutic.

In some embodiments, the pharmaceutical compositions of the presently-disclosed subject matter are in the form of a vaccine. In some embodiments, such immunogenic compositions and vaccines according to the presently disclosed subject matter can comprise or consist essentially of one or more adjuvants. Suitable adjuvants for use in the practice of the presently-disclosed subject matter include, but are not limited to: (1) polymers of acrylic or methacrylic acid, maleic anhydride and alkenyl derivative polymers, (2) immunostimulating sequences (ISS), such as oligodeoxyribonucleotide sequences having one or more non-methylated CpG units (Klinman et al., Proc. Natl. Acad. Sci., USA, 1996, 93, 2879-2883; WO98/16247), (3) an oil in water emulsion, such as the SPT emulsion described on p. 147 of "Vaccine Design, The Subunit and Adjuvant Approach" published by M. Powell, M. Newman, Plenum Press 1995, and the emulsion MF59 described on p 183 of the same work, (4) cation lipids containing a quaternary ammonium salt, (5) cytokines, (6) aluminum hydroxide or aluminum phosphate or (7) other adjuvants such as toll-like receptor ligands or those discussed in any document cited and incorporated by reference into the instant application, or (8) any combinations or mixtures thereof.

The oil in water emulsion (3), which can be particularly appropriate for viral vaccines, can be based on: light liquid paraffin oil (European pharmacopoeia type), isoprenoid oil such as squalane, squalene, oil resulting from the oligomerization of alkenes, e.g. isobutene or decene, esters of acids or alcohols having a straight-chain alkyl group, such as vegetable oils, ethyl oleate, propylene glycol, di(caprylate/caprate), glycerol tri(caprylate/caprate) and propylene glycol dioleate, or esters of branched, fatty alcohols or acids, especially isostearic acid esters. The oil can be used in combination with emulsifiers to form an emulsion. The emulsifiers can be nonionic surfactants, such as: esters of, on the one hand, sorbitan, mannide (e.g. anhydromannitol oleate), glycerol, polyglycerol or propylene glycol and, on the other hand, oleic, isostearic, ricinoleic or hydroxystearic acids, the esters being optionally ethoxylated, or polyoxypropylene-polyoxyethylene copolymer blocks, such as Pluronic® (BASF Corporation, NJ), e.g., L121.

Among the type (1) adjuvant polymers, in some embodiments, the polymers are polymers of crosslinked acrylic or methacrylic acid, including those crosslinked by polyalkenyl ethers of sugars or polyalcohols. These compounds are known under the name carbomer (Pharmeuropa, vol. 8, no. 2, June 1996). One skilled in the art can also refer to U.S. Pat. No. 2,909,462, which provides such acrylic polymers crosslinked by a polyhydroxyl compound having at least three hydroxyl groups, preferably no more than eight such groups, the hydrogen atoms of at least three hydroxyl groups being replaced by unsaturated, aliphatic radicals having at least two carbon atoms. The preferred radicals are those containing 2 to 4 carbon atoms, e.g. vinyls, allyls and other ethylenically unsaturated groups. The unsaturated radicals can also contain other substituents, such as methyl. Products sold under the name CARBOPOL™ (BF Goodrich, Ohio, USA) are, in some embodiments, especially suitable, as such products are crosslinked by allyl saccharose or by allyl pentaerythritol. Among them, reference is made to CARBOPOL™ 974P, 934P and 971 P. As to the maleic anhydride-alkenyl derivative copolymers, in some embodiments, the derivative copolymers are EMA polymers, which are straight-chain or crosslinked ethylene-maleic anhydride copolymers that are, for example, crosslinked by divinyl ether. Reference is also made to J. Fields et al., Nature 186: 778-780, Jun. 4, 1960.

Still further provided, in some embodiments of the presently-disclosed subject matter, are isolated nucleic acids. In some embodiments, isolated nucleic acid sequences are provided that encode an actinohivin variant polypeptide of the presently-disclosed subject matter. In some embodiments, the actinohivin variant polypeptide encoded by the nucleic acids is selected from the group consisting of SEQ ID NOS: 2-13, such as, in certain embodiments, SEQ ID NO: 9. In some embodiments, the nucleic acids described herein further encode an antibody fragment fused or otherwise operably connected to the actinohivin variant polypeptide, such an Fc region of IgG connected to the carboxy-terminus of an actinohivin variant polypeptide. In some embodiments, the nucleic acid sequence encodes a polypeptide having the sequence of SEQ ID NO: 16.

The term "nucleic acid" refers to deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are metabolized in a manner similar to naturally-occurring nucleotides. Unless otherwise indicated, a particular nucleic acid sequence also implicitly encompasses conservatively modified variants thereof (e.g., degenerate codon substitutions or degenerate variants) and complementary sequences and as well as the sequence explicitly indicated.

The term "isolated", when used in the context of an isolated nucleic acid molecule or an isolated polypeptide, is a nucleic acid molecule or polypeptide that, by the hand of man, exists apart from its native environment and is therefore not a product of nature. An isolated nucleic acid molecule or polypeptide can exist in a purified form or can exist in a non-native environment such as, for example, in a transgenic host cell.

The term "degenerate variant" refers to a nucleic acid having a residue sequence that differs from a reference nucleic acid by one or more degenerate codon substitutions. Degenerate codon substitutions can be achieved by generating sequences in which the third position of one or more selected (or all) codons is substituted with mixed base and/or deoxyinosine residues (Batzer et al. (1991) *Nucleic Acid Res* 19:5081; Ohtsuka et al. (1985) *J Biol Chem* 260:2605 2608; Rossolini et al. (1994) *Mol Cell Probes* 8:91 98).

Further provided, in some embodiments, are expression vectors comprising the nucleic acid molecules of the presently-disclosed subject matter operably linked to an expression cassette. The term "vector" is used herein to refer to any vehicle that is capable of transferring a nucleic acid sequence into another cell. For example, vectors which can be used in accordance with the presently-disclosed subject matter include, but are not limited to, plasmids, cosmids, bacteriophages, or viruses, which can be transformed by the introduction of a nucleic acid sequence of the presently-disclosed subject matter. Such vectors are well known to those of ordinary skill in the art.

In some embodiments, the nucleic acids of the presently-disclosed subject matter are operably linked to one another or to an expression cassette. The terms "associated with", "operably linked", and "operatively linked" refer to two sequences that are related physically or functionally. For example, a promoter or regulatory DNA sequence is said to be "associated with" a DNA sequence that encodes an RNA or a polypeptide if the two sequences are operatively linked, or situated such that the regulator DNA sequence will affect the expression level of the coding or structural DNA sequence.

The term "expression cassette" refers to a nucleic acid molecule capable of directing expression of a particular nucleotide sequence in an appropriate host cell, comprising a promoter operatively linked to the nucleotide sequence of interest which is operatively linked to termination signals. It also typically comprises sequences required for proper translation of the nucleotide sequence. The coding region usually encodes a polypeptide of interest but can also encode a functional RNA of interest, for example antisense RNA or a non-translated RNA, in the sense or antisense direction. The expression cassette comprising the nucleotide sequence of interest can be chimeric, meaning that at least one of its components is heterologous with respect to at least one of its other components. The expression cassette can also be one that is naturally occurring but has been obtained in a recombinant form useful for heterologous expression.

The presently-disclosed subject matter also provides transgenic plant cells or plants that have been transformed with one or more of the vectors disclosed herein (i.e., a vector including a nucleic acid molecule encoding an actinohivin variant polypeptide fused to an Fc region of IgG and that directs expression of the nucleic acid molecule in a plant cell). In some embodiments, a plant cell, or a progeny of the plant cell, is provided wherein the plant cell and/or its progeny is transfected with a vector of the presently-disclosed subject matter such that the cell and/or its progeny expresses the polypeptide. As used herein, the term "plant cell" is understood to mean any cell derived from a monocotyledonous or a dicotyledonous plant and capable of constituting undifferentiated tissues such as calli, differentiated tissues such as embryos, portions of monocotyledonous plants, monocotyledonous plants or seed. The term "plant" is understood to mean any differentiated multicellular organism capable of photosynthesis, including monocotyledons and dicotyledons. In some embodiments, the plant cell is a *Nicotiana* or tobacco plant cell, such as a *Nicotiana benthamiana* plant cell that has been transformed with a vector of the presently-disclosed subject matter.

The terms "transformed," "transgenic," and "recombinant" are used herein to refer to a cell of a host organism, such as a plant, into which a heterologous nucleic acid molecule has been introduced. The nucleic acid molecule can be stably integrated into the genome of the cell or the nucleic acid molecule can also be present as an extrachromosomal molecule. Such an extrachromosomal molecule can be auto-replicating. Transformed cells, tissues, or subjects are understood to encompass not only the end product of a transformation process, but also transgenic progeny thereof.

The terms "heterologous," "recombinant," and "exogenous," when used herein to refer to a nucleic acid sequence (e.g., a DNA sequence) or a gene, refer to a sequence that originates from a source foreign to the particular host cell or, if from the same source, is modified from its original form. Thus, a heterologous gene in a host cell includes a gene that is endogenous to the particular host cell but has been modified through, for example, the use of site-directed mutagenesis or other recombinant techniques. The terms also include non-naturally occurring multiple copies of a naturally occurring DNA sequence. Thus, the terms refer to a DNA segment that is foreign or heterologous to the cell, or homologous to the cell but in a position or form within the host cell in which the element is not ordinarily found. Similarly, when used in the context of a polypeptide or amino acid sequence, an exogenous polypeptide or amino acid sequence is a polypeptide or amino acid sequence that originates from a source foreign to the particular host cell or, if from the same source, is modified from its original form. Thus, exogenous DNA segments can be expressed to yield exogenous polypeptides.

Introduction of a nucleic acid (e.g., a nucleic acid incorporated into an appropriate vector) of the presently-disclosed subject matter into a plant cell can be performed by a variety of methods known to those of ordinary skill in the art including, but not limited to, insertion of a nucleic acid sequence of interest into an *Agrobacterium rhizogenes* Ri or *Agrobacterium tumefaciens* Ti plasmid, microinjection, electroporation, or direct precipitation. By way of providing an example, in some embodiments, transient expression of a nucleic acid sequence or gene of interest can be performed by agro-infiltration methods. In this regard, a suspension of *Agrobacterium tumefaciens* containing a nucleic acid sequence or gene of interest can be grown in culture and then vacuum-infiltrated into a plant. Once inside the tissues of the plant (e.g., the leaves of the plant), the *Agrobacterium* transforms the gene of interest to a portion of the plant cells where the gene is then transiently expressed.

As another example, transformation of a plasmid or nucleic acid of interest into a plant cell can be performed by particle gun bombardment techniques. In this regard, a suspension of plant embryos can be grown in liquid culture and then bombarded with plasmids or nucleic acids that are attached to gold particles, wherein the gold particles bound to the plasmid or nucleic acid of interest can be propelled through the membranes of the plant tissues, such as embryonic tissue. Following bombardment, the transformed embryos can then be selected using an appropriate antibiotic to generate new, clonally propagated, transformed embryogenic suspension cultures.

For additional guidance regarding methods of transforming and producing transgenic plant cells, see U.S. Pat. Nos. 4,459,355; 4,536,475; 5,464,763; 5,177,010; 5,187,073; 4,945,050; 5,036,006; 5,100,792; 5,371,014; 5,478,744; 5,179,022; 5,565,346; 5,484,956; 5,508,468; 5,538,877; 5,554,798; 5,489,520; 5,510,318; 5,204,253; 5,405,765; EP Nos. 267,159; 604,662; 672,752; 442,174; 486,233; 486,234; 539,563; 674,725; and, International Patent Application Publication Nos. WO 91/02071 and WO 95/06128, each of which is incorporated herein by this reference.

Still further provided, in some embodiments of the presently-disclosed subject matter, are methods for treating a disease or disorder using the polypeptides (e.g., the lectibodies) described herein. In some embodiments, a method of treating a viral infection is provided that comprises administering a polypeptide of the presently-disclosed subject matter (e.g., an actinohivin variant polypeptide or a lectibody) to a subject in need thereof.

As used herein, the terms "treatment" or "treating" relate to any treatment of a condition of interest (e.g., a viral infection, a cancer, etc.), including, but not limited to, prophylactic treatment and therapeutic treatment. As such, the terms treatment or treating include, but are not limited to: reducing the likelihood of the occurrence of a condition of interest or the development of a condition of interest; inhibiting the progression of a condition of interest; arresting development of a condition of interest; reducing the severity of a condition of interest; ameliorating or relieving symptoms associated with a condition of interest; and causing a regression of the condition of interest or one or more of the symptoms associated with the condition of interest.

In some embodiments, the viral infection is selected from a herpes simplex virus 2 (HSV2) infection, a human immunodeficiency virus (HIV) infection, a hepatitis C virus (HCV) infection, a middle east respiratory virus syndrome (MERS) coronavirus infection, a severe acute respiratory syndrome (SARS) coronavirus infection, an ebola virus infection, a human papilloma virus (HPV) infection, an influenza virus (e.g., H5N1 and other) infection, a simian immunodeficiency virus (SIV) infection, a human T-lymphotrophic virus infection, and a Japanese encephalitis (JE) virus infection. In some embodiments, the viral infection is an HIV infection.

In some embodiments, the polypeptides and compositions described herein can also be administered with one or more additional antiviral agents that are capable of treating a viral infection as defined herein. Antiviral agents that are useful in this regard include, but are not limited to, protease inhibitors, other antiviral lectins, integrase inhibitors, nucleoside reverse transcriptase inhibitors, non-nucleoside reverse transcriptase inhibitors, and nucleotide/nucleoside analogs, with specific examples of such antiviral agents including cyanovirin-N, actinohivin, zidovudine, tenofovir, acyclovir, gangcyclovir, vidarabine, idoxuridine, trifluridine, levovirin, viramidine and ribavirin, as well as foscarnet, amantadine, rimantadine, saquinavir, indinavir, amprenavir, lopinavir, ritonavir, the alpha-interferon, beta-interferon, adefovir, clevadine, entecavir, and pleconaril. In some embodiments, the use of such additional antiviral agents can exhibit synergy when administered with the polypeptides described herein.

In some embodiments of the presently-disclosed therapeutic methods described herein, a method of treating a cancer is provided that comprises administering a polypeptide described herein to a subject in need thereof. The term "cancer" is used herein to refer to all types of cancer or neoplasm or malignant tumors found in a subject, including leukemias, lymphomas, myelomas, carcinomas, melanomas, teratomas, and sarcomas. Examples of cancers include cancer of the liver, pancreas, esophagus, brain, bladder, breast, central nervous system (e.g., spine), cervix, colon, rectum, head and neck, kidney, lung, ovary, prostate, sarcoma, stomach, uterus, leukemias, lymphomas, myelomas, and melanomas. In some embodiments, the cancer is lung cancer, breast cancer, colon cancer, blood cancer, cervical cancer, and/or prostate cancer. In some embodiments, the cancer is characterized by one or more cancer cells having high-mannose-type glycans on a cell membrane of the one or more cancer cells.

For administration of a therapeutic composition as disclosed herein (e.g., a composition comprising an actinohivin variant polypeptide of the presently-disclosed subject matter and a pharmaceutically-acceptable vehicle, carrier, or excipient), conventional methods of extrapolating human dosage based on doses administered to a murine animal model can be carried out using the conversion factor for converting the mouse dosage to human dosage: Dose Human per kg=Dose Mouse per kg/12 (Freireich, et al., (1966) Cancer Chemother Rep. 50:219-244). Drug doses can also be given in milligrams per square meter of body surface area because this method rather than body weight achieves a good correlation to certain metabolic and excretionary functions. Moreover, body surface area can be used as a common denominator for drug dosage in adults and children as well as in different animal species as described by Freireich, et al. (Freireich et al., (1966) Cancer Chemother Rep. 50:219-244). Briefly, to express a mg/kg dose in any given species as the equivalent mg/sq m dose, multiply the dose by the appropriate km factor. In an adult human, 100 mg/kg is equivalent to 100 mg/kg×37 kg/sq m=3700 mg/$m^2$.

Suitable methods for administering a therapeutic composition in accordance with the methods of the presently-disclosed subject matter include, but are not limited to, systemic administration, parenteral administration (including intravascular, intramuscular, intraarterial administration), oral delivery, topical administration, buccal delivery, rectal delivery, vaginal delivery, subcutaneous administration, intraperitoneal administration, inhalation, intratracheal installation, surgical implantation, transdermal delivery, local injection, and hyper-velocity injection/bombardment. Where applicable, continuous infusion can enhance drug accumulation at a target site (see, e.g., U.S. Pat. No. 6,180,082).

Regardless of the route of administration, the compounds of the presently-disclosed subject matter are typically administered in amount effective to achieve the desired response. As used herein, the terms "effective amount" and "therapeutically effective amount" refer to an amount of the therapeutic composition (e.g., a composition comprising an actinohivin variant polypeptide of the presently-disclosed subject matter, and a pharmaceutically-acceptable vehicle, carrier, or excipient) sufficient to produce a measurable biological response (e.g., a reduction in viral infection). Actual dosage levels of active ingredients in a therapeutic composition of the presently-disclosed subject matter can be varied so as to administer an amount of the active polypeptide(s) that is effective to achieve the desired therapeutic response for a particular subject and/or application. Of course, the effective amount in any particular case will depend upon a variety of factors including the activity of the therapeutic composition, formulation, the route of administration, combination with other drugs or treatments, severity of the condition being treated, and the physical condition and prior medical history of the subject being treated. Preferably, a minimal dose is administered, and the dose is escalated in the absence of dose-limiting toxicity to a minimally effective amount. Determination and adjustment of a therapeutically effective dose, as well as evaluation of when and how to make such adjustments, are known to those of ordinary skill in the art.

For additional guidance regarding formulation and dose, see U.S. Pat. Nos. 5,326,902 and 5,234,933; PCT International Publication No. WO 93/25521; Berkow, et al., (1997) The Merck Manual of Medical Information, Home ed. Merck Research Laboratories, Whitehouse Station, New Jersey; Goodman, et al., (2006) Goodman & Gilman's the Pharmacological Basis of Therapeutics, 11th ed. McGraw-Hill Health Professions Division, New York; Ebadi. (1998) CRC Desk Reference of Clinical Pharmacology. CRC Press, Boca Raton, Florida; Katzung, (2007) Basic & Clinical Pharmacology, 10th ed. Lange Medical Books/McGraw-Hill Medical Pub. Division, New York; Remington, et al., (1990) Remington's Pharmaceutical Sciences, 18th ed. Mack Pub. Co., Easton, Pennsylvania; Speight, et al., (1997) Avery's Drug Treatment: A Guide to the Properties, Choice, Therapeutic Use and Economic Value of Drugs in Disease Management, 4th ed. Adis International, Auckland/Philadelphia; and Duch, et al., (1998) Toxicol. Lett. 100-101:255-263, each of which are incorporated herein by reference.

As used herein, the term "subject" includes both human and animal subjects. Thus, veterinary therapeutic uses are provided in accordance with the presently-disclosed subject matter. As such, the presently-disclosed subject matter provides for the treatment of mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economic importance to humans. Thus, also provided is the treatment of livestock, including, but not limited to, domesticated swine, ruminants, ungulates, horses (including race horses), poultry, and the like.

The practice of the presently-disclosed subject matter can employ, unless otherwise indicated, conventional techniques of cell biology, cell culture, molecular biology, transgenic biology, microbiology, recombinant DNA, and immunology, which are within the skill of the art. Such techniques are explained fully in the literature. See, e.g., Molecular Cloning A Laboratory Manual (1989), 2nd Ed., ed. by Sambrook, Fritsch and Maniatis, eds., Cold Spring Harbor Laboratory Press, Chapters 16 and 17; U.S. Pat. No. 4,683,195; DNA Cloning, Volumes I and II, Glover, ed., 1985; Polynucleotide Synthesis, M. J. Gait, ed., 1984; Nucleic Acid Hybridization, D. Hames & S. J. Higgins, eds., 1984; Transcription and Translation, B. D. Hames & S. J. Higgins, eds., 1984; Culture Of Animal Cells, R. I. Freshney, Alan R. Liss, Inc., 1987; Immobilized Cells And Enzymes, IRL Press, 1986; Perbal (1984), A Practical Guide To Molecular Cloning; See Methods In Enzymology (Academic Press, Inc., N.Y.); Gene Transfer Vectors For Mammalian Cells, J. H. Miller and M. P. Calos, eds., Cold Spring Harbor Laboratory, 1987; Methods In Enzymology, Vols. 154 and 155, Wu et al., eds., Academic Press Inc., N.Y.; Immunochemical Methods In Cell And Molecular Biology (Mayer and Walker, eds., Academic Press, London, 1987; Handbook Of Experimental Immunology, Volumes I-IV, D. M. Weir and C. C. Blackwell, eds., 1986.

The presently-disclosed subject matter is further illustrated by the following specific but non-limiting examples.

EXAMPLES

The examples below describe the development and characterization of an AvFc lectibody that was engineered and produced by a plant virus vector overexpression system in *Nicotiana benthamiana* plants. As described below, in flow cytometry analysis, AvFc exhibited broad recognition of tumor cell lines, including breast, colorectal, cervical, lung and blood cancer; with the binding being saturated at less than or equal to 10 μg/mL in many cells. By contrast, AvFc showed marginal binding to untransformed cells including peripheral blood mononuclear cells (PBMCs) and the non-tumorigenic breast epithelial cell line MCF 10A, indicating AvFc's high specificity to malignant cells. Surface plasmon resonance demonstrated AvFc's capacity to bind to Fc receptors. In vitro bioassays further revealed that AvFc was capable of inducing antibody dependent cell-mediated cytotoxicity (ADCC) with less than or equal to 1 μg/mL effective concentrations against multiple cancer cells. Meanwhile, AvFc showed no cytotoxicity or mitogenicity in human PBMCs. A single-dose (4 mg/kg) intravenous infusion study in rats showed an extended half-life of AvFc compared to Avaren. A multiple dosing study (5 and 20 mg/kg, twice a week over 4 weeks) in mice showed no significant toxicity according to macroscopic, histological and blood analyses. Collectively, these results indicated that the AvFc lectibody holds unique immunotherapeutic and diagnostic capabilities against a broad range of carcinomas and a good safety profile upon intravenous administration.

Materials and Methods

Vector construction of AH and AH variants. A "deconstructed" tobamovirus replicon system (magnICON; Icon Genetics GmbH) was used to express actinohivin (AH) and AH variants in *N. benthamiana*. AH (GenBank accession no. AB032371) and AH variant coding sequences (*Nicotiana benthamiana* codon optimized) were generated synthetically and sub-cloned into the magnICON vector pICH11599 via standard molecular biology/subcloning procedures using Nco I/Sac I restriction sites.

Viral vector-based overexpression of AH and AH variants in *Nicotiana benthamiana*. Plant expression of AH and AH variants was performed using the magnICON® system. The 3' provector of each AH and AH variant was used with the 5' provectors pICH20155 and pICH14011. The vectors were delivered into *Nicotiana benthamiana* leaves using the *Agrobacterium* vacuum infiltration method. After 5 days, leaf material was homogenized by a Precellys 24 homogenizer (Bertin Technologies, Rockville, MD) in extraction buffer (Phosphate buffered saline pH 7.2, 40 mM ascorbic acid). The resulting extract was clarified by centrifugation at 10,000×g for 5 minutes, and analyzed for protein expression by SDS-PAGE and gp120-capture ELISA.

Circular dichroism (CD) studies. AH and Avaren (Ah Variant 8 of 14) were buffer exchanged into a low salt buffer (10 mM phosphate buffer, pH 7.0) using 3.5 MWCO dialysis cassettes. CD spectra were collected on a JASCO J-815 CD spectrometer (JASCO Ltd. UK) with a 1 nm bandwidth, using 1.0 mm and 10.0 mm pathlength cuvettes for far-UV and near-UV scans, respectively. The scans were performed at 20° C., and corrected for the blank (low salt buffer) control. Protein concentrations were determined by absorbance at 280 nm and converted to mean residue ellipticity [0] or molar ellipticity.

Biomass production and agro-infiltration of AvFc. K1DFX-P2 *Nicotiana benthamiana* plants were grown for 25 days within a contained growth room environment under artificial lighting. AvFc *agrobacterium* vectors were transiently delivered into the plants by vacuum infiltration (24" vacuum for 2 minutes). Post-infiltration, the plants were incubated for seven days, and whole leaf tissues were harvested by mechanical cutting.

Extraction and clarification of AvFc. The harvested biomass was mechanically disintegrated in a 2:1 buffer (20 mM sodium phosphate, 40 mM ascorbic acid, pH 7.0) to tissue ratio. The raw extract was adjusted to pH 7.0±0.05 using sodium hydroxide. Celpure diatomaceous earth (Advanced Minerals) was added at 33 g per liter as a filter aid. The extract and diatomaceous earth (DE) slurry were then clarified using a plate-frame filter press and cellulose 0.3 micron pads (Ertel Alsop). The packed press was then washed with 10 volumes of extraction buffer to improve recovery. The filter press filtrate and wash were combined to create the Protein A feed.

Purification of AvFc. AvFc from the clarified extract was captured on a MabSelect SuRe Protein A column (GE Healthcare), which was equilibrated with 5 column volumes (CV) of 20 mM sodium phosphate, pH 7.0; the clarified extract was applied through a 1.2 micron glass fiber filter with a residence time of 2-10 minutes per CV. After feed application, the column was washed with equilibration buffer (5 mM Sodium Phosphate, pH 6.8) to reach the UV baseline. The column was then eluted using a step to 2M Arginine, pH 3.0. The elution fraction was immediately neutralized to pH 6.8±0.05 using 1M Tris, pH 8.0 buffer, and sterile-filtered prior to further chromatography. AvFc was further purified using a CHT Type II m column (Bio-Rad). The column was conditioned using 1 CV of neutralization buffer (250 mM Sodium Phosphate, pH 6.8), and equilibrated using 10 CV of equilibration buffer. The Protein A elution pool was diluted to <10 mS/cm with Water for Irrigation (WFI) and loaded onto the column with a two minute residence time. After feed application, the column was washed with 5 CV of equilibration buffer to reach the UV baseline and eluted using a 15 CV linear gradient to 5 mM sodium Phosphate+800 mM NaCl, pH 6.8. After collection of the elution peak, the CHT column was stripped using 250 mM Sodium Phosphate, 4M NaCl, pH 6.8. The CHT elution pool was concentrated 10-20 fold using a 30 kDa tangential flow ultrafiltration cassette (Sartorius), followed by a 7× diafiltration against Dulbecco's PBS (Invitrogen). The retentate was sterile-filtered using a 0.2 micron cellulose acetate filter prior to storage at 2-8° C.

Surface plasmon resonance (for gp120 Binding). The binding affinity ($K_D$) of AH, Avaren, or AvFc to gp120 was measured using a Biacore X100 2.0 instrument at ambient temperature. Recombinant His-tagged gp120 (Q759.h5 Immune-tech #IT-001-0012p, SF162 Immune-tech #IT-001-0028p-PBS, ZM53M.PB12 Immune-tech #IT-001-RC8p) was captured on a sensor chip NTA following the manufacturer's instructions to a surface density of about 30 RU. A reference flow cell was utilized to correct response contributions such as bulk shifts that occur equally in the sample and reference flow cells. Serial dilutions of AH, Avaren or AvFc were made in running buffer (HPS-P+ with 50 μM EDTA, GE Healthcare), and injected at a flow rate of 5 μl/min, for a contact time of 120 s and a dissociation time of 1200 s. A blank cycle (running buffer) was performed and all sample injections were blank subtracted to correct the sensorgrams for drifts and other disturbances that affect the reference subtracted curve. Between sample injections the system was washed with NTA wash buffer, with the surface regenerated with the NTA regeneration solution. A replicate of a non-zero concentration of gp120 and the blank were injected in each experiment for double referencing, thus verifying the reliability of the immobilized chip throughout the experiment. The data were assessed by Steady State binding analysis.

ELISA-based binding analysis using HIV-1 gp120 treated with α-mannosidase. Recombinant gp120 (SF162, HIV1/Clade B, Immune-tech #IT-001-0028p-PBS) was cleaved with α(1-2,3,6) mannosidase (PROzyme #GKX-5010). A volume of 1 μl of gp120 was added to 10 μl of 5× reaction buffer (supplied from PROzyme), 20 μl of α(1-2,3,6) mannosidase and 19 μl of de-ionized water. A control untreated reaction was set up in the same manner replacing the α(1-2,3,6) mannosidase with de-ionized water. The treated and untreated reactions were incubated for 24 hours at 37° C. After 24 hours, a gp120-captured enzyme-linked immunosorbent assay (gp120 ELISA) was performed. ELISA plates were coated with treated or untreated reactions (diluted to 3 ml in 50 mM carbonate-bicarbonate, pH 9.6, coating buffer; final concentration of 330 ng/ml gp120) and blocked with blocking buffer (phosphate-buffered saline [PBS], pH 7.2, 0.05% Tween-20, 5% [w/v] non-fat dry milk). Three fold serially diluted antibodies (AvFc, VRC01 or 2G12) starting at 1 μg/ml were applied onto the plates and incubated for 1 h at 37° C. The gp120-bound antibodies were detected by HRP conjugated mouse anti-human IgG (FC) (Southern Biotech #9040-05) at a 1:5,000 dilution. A tetramethylbenzidine substrate (BioFX Laboratories #TMBS-1000-01, Owings Mills, MD) was used for detection; absorbance at 450 nm was measured on a plate reader (Biotek, Winooski, VT). Graphs were plotted in the GraphPad Prism 5.0 software.

Env-pseudotyped HIV-1 neutralization assay. The antiviral activity of AvFc was assessed based on reduction in luciferase reporter gene expression after infection of HOS cells with Env-pseudotyped viruses. The assay was done in triplicates and performed essentially as described elsewhere. Antiviral activity was reflected by $IC_{50}$, which is the sample concentration yielding 50% of relative luminescence units (RLUs) compared with those of virus control after subtraction of background RLUs. Env-pseudotyped viruses were prepared by co-transfection of 293T/17 cells with various env-expressing plasmids and an env-deficient HIV-1 backbone vector (pNL4-3.Luc.R-.E-), and were titrated in HOS cells to determine the optimal viral dilution yielding ~150,000 RLUs. Samples and virus preparations were incubated for 1 h at 37° C., and 10,000 cells/well of HOS cells were added for 72 h. Luciferase activity was measured using the Luciferase Assay System (Promega).

Syncytium formation assay. The assay was performed in triplicate and essentially as previously described, except that HL2/3 cells expressing HIV-1 gp120 were used for fusion with TZM-b1 $CD4^+$ target cells[3]. To prepare leaf extract samples, leaf materials were homogenized in 3 v/w extraction buffer (PBS, pH 7.2, 40 mM ascorbic acid) and centrifuged. Samples, diluted 1/20 in GIBCO Dulbecco's modified Eagle's medium (DMEM; Invitrogen) containing 10% fetal bovine serum, 1% penicillin/streptomycin and 500 μg/ml geneticin, were added to 12,000 each of HL2/3 and TZM-b1 cells in a 96-well plate, and incubated for 18 h at 37° C. in a humid environment containing 5% $CO_2$. Cells were washed and lysed with 0.05% Triton X-100. To quantify syncytia, a developing reagent (60 mM $Na_2HIPO_4$, 40 mM $NaH_2PO_4$, 10 mM KCl, 1 mM $MgSO_4$, 50 mM 2-mercaptoethanol, 0.8 mg/mL ortho-Nitrophenyl-b-galactoside) was added and incubated at 37° C. for 2 to 4 h. The reaction was stopped with 2 M $Na_2CO_3$, and OD420 was read. Percent syncytium formation was reflected by the reduction in β-galactosidase activity from sample wells versus that of cell only positive control wells.

Primary HIV-1 neutralization assay. Fresh PBMCs (ZenBio, Research Triangle Park, NC) were stimulated with phytohemagglutinin (PHA) (Roche, Indianapolis, IN) (5 μg/ml) for 24 h at 37° C. in a humid environment containing 5% $CO_2$, in 1:1 (v/v) RPMI 1640 (Gibco/Invitrogen, Carlsbad, CA) and AIM-V medium, supplemented with 10% FBS (Hyclone), 100 μg/ml streptomycin, 100 U/ml penicillin, L-glutamine and N-2-hydroxyethylpiperazine-N'-2-ethanesulfonic acid (HEPES) (cRPMI). PHA blasts were then grown in cRPMI supplemented with 50 U/mL recombinant human IL-2 (ZeptoMetrix, Buffalo, NY). Samples and virus solutions were incubated for 1 h at 37° C. with 5% $CO_2$ prior to the addition of 250,000 cells per well. After 72 h of culture, the media were changed for further 24 h of incubation. Upon addition of lysis buffer (1% Triton X-100), the plates were stored at −20° C. $IC_{50}$s, expressed as 50% reduction of p24, were determined according to the manufacturer's protocol (Sino Biologicals, China). The assay was done in quadruplicate for each virus strain.

Surface plasmon resonance (for FcγR binding). The binding affinity ($K_D$) of recombinant human Fc gamma receptors, IA or IIIA, to AvFc was measured on a Biacore X100 2.0 instrument at ambient temperature. AvFc was captured on a sensor chip via an anti-human IgG (Fc) antibody of IgG1 isotype, and varying concentrations of each recombinant FcγR were used as analytes. Briefly, monoclonal mouse anti-human IgG (Fc) antibody of IgG1 isotype (25 μg/ml) was immobilized on a CM5 sensor chip (GE Healthcare Biosciences) to 10,000 resonance units (RU) using the human antibody capture kit (GE Healthcare Biosciences). A reference flow cell was immobilized with the antibody to correct response contributions such as bulk shifts that occur equally in the sample and reference flow cells. AvFc was captured on the anti-human IgG (Fc) chip to a surface density of about 200 RU. In the FcγRI sensorgram the raw (colored lines) and fitted (black lines) curves represent FcγRI concentrations (1.2, 0.4, 0.13, 0.044, and 0.015 μg/ml from top to bottom). In the FcγRIIIa sensorgram, the raw data curves (colored lines) represent FcγRIIIa concentrations (100, 33.3, 11.1, 3.7, 1.2 and 0.41 μg/ml from top to bottom). The analysis was done in two independent experiments. The average equilibrium dissociation constant $K_D$ (mean±SEM) was determined based on 1:1 binding kinetics for FcγRI or on steady state for FcγRIIIA.

Flow cytometry (for FcγR binding). Fc gamma receptor (FcγR) binding by AvFc was demonstrated on a BD FACSAria flow cytometer using both FcγRI (CD64+) and FcγRIIIA ($CD16A^+$) TZM-b1 cells (NIH ARP). Initially, background binding of Avaren to TZM-b1 cells was blocked by incubating AvFc with mannan. Then a 1:1 mixture of blocked AvFc and $1\times10^6$ of FcγR expressing cells were mixed for one hour at room temperature followed by three independent washes in DPBS. AvFc bound to FcγR was detected by incubating the cells with a goat $F(ab')_2$ anti-human IgG (Fc)—FITC secondary antibody. After one hour cells were again washed three times with DPBS. Cells were then fixed in 1% paraformaldehyde and analyzed on the flow cytometer. A non-FcγR binding AvFc mutant was used as a negative control and human $IgG_\kappa$ was used as a positive control. The analysis was done in triplicate. % Binding was taken as the percent of the total viable cell population with a fluorescence intensity greater than a cell only control.

Surface plasmon resonance (for neonatal Fc receptor [FcRn] binding). The binding affinity ($K_D$) of FcRn to AvFc was measured using a Biacore X100 2.0 instrument at ambient temperature. Briefly, gp120CM (NIH AIDS Reagent Program) was immobilized on a CM5 sensor chip (Biacore) to 8,000 resonance units (RUs) using the amine coupling kit (Biacore). A reference flow cell was immobilized with gp120CM to correct response contributions such as bulk shifts that occur equally in the sample and reference flow cells. AvFc was captured on the gp120CM chip to a surface density of about 100-200 RUs. Serial dilutions of recombinant human FcRn (rFCGRT and B2M, Sino Bio #CT009-H08H) (5 μg/ml to 0.0617 μg/ml) were made in running buffer (HPS-EP, GE Healthcare) and injected, at a flow rate of 5 μl/min, for a contact time of 60 s and a dissociation time of 600 s. A blank cycle (running buffer) was performed and all sample injections were blank subtracted to correct the sensorgrams for drifts and other disturbances that affect the reference subtracted curve. Between sample injections the system was washed with running buffer; the immobilized surface was regenerated with Regeneration solution included in the human antibody capture kit. A replicate of a non-zero concentration of FcRn and the blank were injected in each experiment for double referencing, thus verifying the reliability of the immobilized chip throughout the experiment. The data were assessed by Steady State analysis in the Biacore X100 2.0 evaluation software.

ADCVI assay. HIV-$1_{92US657}$ is an R5 primary isolate obtained from the NIH AIDS Reagents Program. The virus was propagated by infecting phytohemagglutinin (PHA)- stimulated PBMCs from a healthy donor by spinoculation (1200×g at room temperature for 2 h). The virus was passaged twice on PHA-stimulated PBMCs, and stocks were stored at −80° C. until use. Human PBMCs obtained by Ficoll-Hypaque gradient centrifugation were allowed to adhere to polystyrene flasks for 1 h. Non-adherent cells were collected and stimulated for 24 h with 5 μg/ml PHA-L in cRPMI. $CD4^+$ lymphocytes and natural killer (NK) effector cells were then magnetically separated from PBMCs with anti-CD4 and anti-CD56 monoclonal antibodies, respectively (Miltenyi Biotech, Auburn, Calif.). $CD4^+$ lymphocytes were infected with HIV-$1_{92US657}$ at a multiplicity of infection of approximately 0.05 for 48-72 h. $CD4^+$ lymphocytes were initially propagated for 3 days in cRPMI supplemented with PHA-L (5 μg/ml) and IL-2 (20 U/ml), followed by maintenance with just IL-2. NK cells were propagated in cRPMI supplemented with IL-2 (20 U/ml). Next, $5\times10^4$ $CD4^+$ infected lymphocytes and $1\times10^5$ NK cells, effector/target cell (E:T) ratio of 2:1, were co-incubated with various concentrations of AvFc and VRC01 in 96 well plate for 72 h. Supernatants were sampled for p24 detection by ELISA (ZeptoMetrix; Buffalo, N.Y.). Control wells lacking the compound but containing NK cells (effector control, $CD4^+$ lymphocytes+NK cells), and viral replication control wells lacking both the compound and NK cells ($CD4^+$ lymphocytes only) were included in every 96-well plate. The assay was done in triplicate. Virus inhibition was calculated as follows: % inhibition$=\{1-([p24_t]/[p24_{ut}])\}\times100$, where $[p24_t]$ is the concentration of p24 in the supernatant of wells containing a given compound, and $[p24_{ut}]$ the concentration of p24 from the wells lacking the compound.

Flow cytometry analysis of AvFc binding to human cells. All cell lines were obtained from American Type Culture Collection (ATCC, Manassas, VA) and authenticated by the supplier. Cells were grown according to ATCC's recommendations, regularly screened for *Mycoplasma* using a commercial PCR-based kit (ATCC) and used for analysis at low passage numbers, with quality ensured based on viability and morphologic inspection. Cells were incubated with various concentrations of AvFc (0.1, 1 and 10 μg/mL) in medium for 30 minutes on ice, then washed 3 times with DPBS. Cells were then incubated with a goat $F(ab')_2$ anti-Human IgG Fc FITC antibody (Abcam, Cambridge, MA) for 30 minutes in the dark on ice. After washing 3 additional times with DPBS, cells were fixed with 1% paraformaldehyde. Data were acquired on a FACSAria (BD BioSciences, San Jose, CA), counting 10,000 events per sample, and percentage of FITC+ cells was determined using FlowJo (version 10) software. VRC01 was used as a control. The analysis was done in triplicate for each cell type.

Immunocytochemistry. Fluorescent imaging (Axio Observer. Z1, ZEISS) was used to visualize AvFc binding to N-linked HMGs on the surface of cancer cells. MCF10A or H460 cancer cells (10,000 cells/chamber) were incubated overnight at 37° C. with 5% $CO_2$ in an 8-well chamber slide (Nunc, Rochester, NY) before fixation with 1% paraformaldehyde. Chambers were then blocked prior to the addition of AvFc at 1 μg/mL for 2 hours at room temperature. AvFc bound cancer cells were finally detected with anti-human (Fc) FITC secondary antibody (Abcam, Cambridge, MA), with the nuclei stained with a mounting medium containing DAPI (Vector Labs, Burlingame, CA).

Immunohistochemistry. Formalin-fixed paraffin embedded human colon tissue sections were obtained as a human colon cancer tissue microarray (US Biomax, Rockville, MD). Samples consisted of duplicate cores of 6 colon adenocarcinomas of varying grades and stages and the corresponding adjacent normal colon tissue. Tissue sections were de-paraffinized and rehydrated and endogenous peroxidase was quenched with 3% $H_2O_2$. The sections were then blocked with the Endogenous Avidin+Biotin Blocking System (Abcam, Cambridge, MA), Human-to-Human Blocking Reagent (ScyTek Labs, Logan, UT), Blocking Buffer containing relevant animal serum and Human Fc Block (BD BioSciences, San Jose, CA). After blocking, sections were incubated overnight at 4° C. with 10 μg/mL AvFc in blocking buffer, or blocking buffer only as a negative control. After washing, AvFc was detected with the anti-Avaren monoclonal antibody 3A7F9, washed again, and incubated with the corresponding biotinylated secondary antibody (Vector Labs, Burlingame, CA). VECTASTAIN Elite ABC Kit (Vector Labs, Burlingame, CA) was used to amplify the immunoreactions, followed by ImmPACT DAB Peroxidase Substrate (Vector Labs, Burlingame, CA), both according to the manufacturer's protocols. Samples were counterstained with hematoxylin, dehydrated, and mounted with Permount mounting medium (Thermo-Fisher, Waltham, MA). The immunostained slides were viewed and imaged using an Aperio Digital Pathology Slide Scanner (Leica Biosystems, Buffalo Grove, IL).

ADCC Assay. Antibody-dependent cellular cytoxicity (ADCC) was assessed using an ADCC Reporter Bioassay (Promega, Madison, WI) following the manufacturer's protocol. The assay was done in triplicate. Briefly, A549, MCF7 and RKO cells were used as target cells and seeded in 96-well flat-bottom Falcon culture plates (Corning, Tewksbury, MA) and incubated at 37° C. with 5% $CO_2$. Twenty-four hours later, various concentrations of AvFc, N200Q-AvFc, cetuximab or trastuzumab were added to target cells along with the Jurkat NFAT-luc FcγRIIIa-expressing cell line (Jur-γRIIIa; Promega, Madison, WI) at a ratio of 15:1. FcγRIIIa signaling activates the NFAT transcription factor, inducing expression of firefly luciferase driven by an NFAT responsive promoter (a). After co-culturing for 24 hours, the cells were lysed, transferred to a white 96-well assay plate, and firefly luciferase activity was measured using the Bio-Glo luciferase assay system (Promega, Madison, WI) on a Synergy HT luminometer. Jur-γRIIIa cells co-cultured with the target cells in the absence of antibody provided background (antibody-independent) luciferase production levels, which were subtracted from the actual signals to yield antibody-specific activation, in relative light units (RLUs).

Analysis of lectin interaction with PBMC surface molecules by flow cytometry. Cryopreserved human PBMCs from three different donors were purchased from Precision Bioservices (Frederick, MD). Cells were quickly thawed at 37° C. and immediately cultured in RPMI 1640 supplemented with 10% fetal bovine serum (FBS) and an antibiotic cocktail composed of penicillin and streptomycin at final concentrations of 100 U/ml and 100 μg/ml, respectively. PBMCs were seeded into 24-well culture plates (CellTreat, MA) at $1\times10^6$ cells per well. AvFc was added at concentrations of 30 and 100 μg/ml, respectively, followed by overnight incubation at 37° C. with 5% $CO_2$. For flow cytometry experiments, cells were blocked for 10 min with purified rat anti-mouse CD16/CD32 (Mouse BD Fc Block) on ice, and incubated in presence of guinea pig anti-AH antibodies for 1 h. After 2 washes with PBS containing 5% inactivated FBS (washing solution), Cy3-conjugated anti-guinea pig secondary antibodies raised in goat (EMD Millipore, Billerica, MA) were added to cells and incubated in dark for 20 min (on ice). Finally, PBMCs were washed and analyzed on a FACSCalibur (BD, San Jose, CA), counting 50 000 events per sample. Data were acquired and analyzed using Cell- Quest Pro from BD. Control cells were cultured solely in presence of the medium. To assess whether the binding of PBMCs by AvFc is mediated by Fc-receptors on the cell surface, PBMCs were blocked by addition of 50 μl human serum block (instead of the mouse Fc blocking reagent) prior to primary and secondary antibody incubation steps.

Cell viability assays. Cell viability of PBMCs from three different donors was assessed by flow cytometry after staining with propidium iodide, a dye excluded by live cells. Data were acquired on a FACSCalibur (BD, San Jose, CA), counting 10,000 events per sample; analyzes were carried out with the CellQuest Pro software from BD. ConA (10 μg/ml) and PBS were used as controls.

Mitogenicity assays. Proliferation of human PBMCs from three different donors was studied by flow cytometry according to well established protocols used in lectin studies. Briefly, cells were treated with AvFc for 72 h and analyzed for any changes in size and/or morphology using forward scatter (FSC) and side scatter (SSC) on a FACSCalibur (BD, San Jose, CA), counting 10,000 events per sample. Data were acquired and analyzed using CellQuest Pro from BD. ConA (10 μg/ml) and PBS were used as controls.

Evaluation of cellular activation markers. Freshly thawed human PBMCs from three different donors were cultured for 3 days and analyzed by flow cytometry after dual fluorescent staining with monoclonal antibodies purchased from BD Pharmingen (San Diego, CA). Briefly, cell cultures were transferred from plates to 5 ml round bottom tubes and washed with 5% inactivated FBS in PBS (washing solution). After blocking for 10 min with purified rat anti-mouse CD16/CD32 (Mouse BD Fc Block), the cells were incubated in the dark with FITC-conjugated anti-CD4 mAb in combination with PE-conjugated anti-CD25, anti-CD69 or anti HLA-DR mAb for 30 min on ice. After a final washing step, data were acquired on a FACSCalibur (BD, San Jose, CA), counting 10 000 events per sample, and analyzed using CellQuest Pro from BD. ConA (10 μg/ml) and PBS were used as controls.

Immunoassays for cytokine detection in PBMC supernatants. PBMCs from 5 different blood donors were cultured in presence of 30 or 100 μg/ml AvFc for three days, and the concentrations of interleukin (IL)-1α, IL-1b, IL-2, IL-3, IL-4, IL-5, IL-6, IL-7, IL-8, IL-10, IL-12p40, IL-12p70, IL-13, IL-15, IL-17, eotaxin, granulocyte-macrophage colony-stimulating factor (GM-CSF or CSF2), granulocyte colony-stimulating factor (G-CSF or CSF3), interferon gamma (IFN)-γ, IFN-α2, interferon γ-inducible protein-10 (IP-10), monocyte chemoattractant protein-1(MCP-1), macrophage inflammatory protein (MIP)-1α, MIP-1β, tumor necrosis factor (TNF)-α, and TNF-b were evaluated in culture supernatants by the Luminex IS100 system (Milipore) using the Milliplex Human Cytokine/chemokine 26-plex kit according to the manufacturer's instructions. Data were generated with the xPONENT software. Individual ELISAs were employed to evaluate the amounts of IL-1β, IL-6 and IL-8 in cell culture supernatants collected from PBMC cultures after 24 hours of incubation in presence of AvFc (30 or 100 μg/ml) or controls (10 μg/ml ConA or PBS). ELISA Ready-SET-Go! Kits were purchased from eBioscience Inc. and used in these experiments following the manufacturer's instructions. The experiments were repeated for a total of at least two times.

Gene expression analysis in human PBMCs. PBMCs from three blood donors were incubated with AvFc (30 or 100 μg/ml), ConA (10 μg/ml), or buffer vehicle only for 16 hours. Cell lysates were homogenized using the Qiagen QIAshredder kit, and a Qiagen RNeasy Mini Kit was used for total RNA extraction and purification. Gene expression was assessed by quantitative RT-PCR using quality verified RNA samples. First strand cDNA was obtained from reverse transcription of 150 ng RNA using a SUPERSCRIPT VILO cDNA synthesis kit (Life Technologies) according to the manufacturer's instructions. Optimal amounts of template cDNA were added to a reaction mixture containing 10 μl of 2×TaqMan® Fast Advanced Master Mix (Life Technologies) and endonuclease free water to 20 μl and loaded in TaqMan® Array Standard 96 well Plates (Applied Biosystems). These plates contain pre-spotted individual TaqMan® Gene Expression probes for detection of monocyte chemoattractant protein-1 (MCP-1), macrophage inflammatory protein 1α (MIP-1α), Chemokine (C-C motif) ligand 5 also known as Regulated on Activation, Normal T Cell Expressed and Secreted (RANTES), granulocyte-macrophage colony-stimulating factor (GM-CSF), granulocyte colony-stimulating factor (G-CSF), interferon γ-inducible protein-10 (IP-10), interferon gamma-γ (IFN-γ), interleukin (IL)-10, IL-12A, IL-13, IL-15, IL-1A, IL-1B, IL-2, IL-3, IL-4, IL-5, IL-6, IL-7, IL-8, and tumor necrosis factor-α (TNF-α) as well as the house keeping genes 18 S, beta actin (ACTB), and glyceraldehyde 3-phosphate dehydrogenase (GAPDH), summarized in Table 1. PCR amplification was carried out using a 7900HT Fast Real-Time PCR System (Applied Biosystems) in the following conditions: 95° C., 20 min; 40 cycles (95° C., 1 min); 20 min at 60° C. The 7500 software v2.0.6 (Applied Biosystems) was used to determine the cycle threshold (Ct) for each reaction and derive the expression ratios as previously described.

TABLE 1

Relative expression of selected cytokine and chemokine genes after treatment with AvFc (100 and 30 μg/ml) and 10 μg/ml ConA as evaluated by quantitative PCR.

| | 100 μg/ml AvFc Means ± SEM (n ± 3) | 30 μg/ml AvFc Means ± SEM (n ± 3) | 10 μg/ml ConA Means ± SEM (n ± 3) |
|---|---|---|---|
| CCL2 | 1.47 ± 0.26 | 1.60 ± 0.52 | 7.44 ± 3.25 |
| CCL3 | 0.72 ± 0.10 | 0.72 ± 0.09 | 1.60 ± 1.06 |
| CCL5 | 0.96 ± 0.13 | 1.05 ± 0.04 | 0.99 ± 0.31 |
| CSF2 | 0.89 ± 0.77 | 1.14 ± 0.88 | 1778.30 ± 1380.19 |
| CSF3 | 0.23 ± 0.15 | 0.89 ± 1.19 | 19.04 ± 23.32 |
| CXCL10 | 8.90 ± 8.54 | 5.95 ± 4.66 | 142.13 ± 156.96 |
| IFN-G | 7.64 ± 10.33 | 13.16 ± 18.33 | 10815.00 ± 11127.79 |
| IL-10 | 1.23 ± 0.65 | 1.13 ± 0.11 | 6.52 ± 1.94 |
| IL-12A | 0.85 ± 0.16 | 0.96 ± 0.11 | 1.70 ± 0.45 |
| IL-13 | n.d. | n.d. | 1722.49* |
| IL-15 | 1.31 ± 0.52 | 1.25 ± 0.26 | 3.89 ± 0.96 |
| IL-1A | 0.90 ± 0.46 | 0.92 ± 0.16 | 74.32 ± 79.71 |
| IL-1B | 0.89 ± 0.56 | 1.06 ± 0.26 | 135.35 ± 109.88 |
| IL-2 | 1.48 ± 1.29 | 1.39 ± 0.76 | 1062.75 ± 645.83 |
| IL-3 | 1.41 ± 0.69 | 1.03* | 2289.12 ± 828.93 |
| IL-4 | n.d. | n.d. | 536.48 ± 620.80 |
| IL-5 | n.d. | n.d. | 562.94 ± 597.96 |
| IL-6 | 1.53 ± 0.54 | 1.62 ± 1.21 | 518.55 ± 443.20 |
| IL-7 | 1.49 ± 0.30 | 1.40 ± 0.22 | 2.54 ± 0.53 |
| IL-8 | 1.97 ± 0.93 | 1.43 ± 0.37 | 71.93 ± 60.94 |
| TNF-A | 1.35 ± 0.36 | 1.24 ± 0.47 | 26.54 ± 7.66 |

n.d.: non detected.
*Detected only in one PBMC sample

Animal housing and care. Eight week-old female Sprague-Dawley rats (Charles River Laboratories, Wilmington, MA) weighing approximately 250 g (for the single-dose biodistribution study), 6-to-8-week-old female BALB/c mice (Jackson Laboratory; for the repeated-dose toxicity study) and 6 week-old female C57bl/6 mice (Charles River; for the tumor imaging study) were housed in a temperature- and humidity-controlled environment, with an alternating light/dark cycle of 12 *h* and free access to standard diet and water. The investigators were not blinded for sample administration. All experimental procedures were approved by the University of Louisville's Institutional Animal Care and Use Committee.

PET/CT imaging. The in vivo tumor-targeting property of AvFc was determined with radiolabeled AvFc in B16/F10 melanoma-bearing C57bl/6 mice using small animal PET/CT. The C57 mice (n=2) were subcutaneously inoculated with $1\times10^6$ B16/F10 cells on the right flank for each mouse to generate B16/F10 tumors. The mice were used for imaging study when the weights of tumors reached approximately 0.2 g 10 days post-cell inoculation. Approximately 3.7 MBq of purified $^{64}$Cu-AvFc was injected into each mouse via the tail vein. The mice were scanned with small animal PET and CT at 24 h post-injection. The 10 min CT imaging (MicroCAT II) was immediately followed by the 30 min PET imaging conducted by MicroPET (Siemens R4) using the same animal bed. The PET and CT data were reconstructed and merged by Siemens IRW software.

Rat treatments and sample collection. The animals were randomly divided into three groups (n=4) to receive endotoxin free samples, including AvFc (4 mg/kg), Avaren (4 mg/kg) or/and an equivalent volume of the formulation buffer (30 mM histidine pH 7.4, 250 mM sucrose), respectively, administered by tail vein injection. Following treatment, blood samples were collected by tail-vein at various time points for serum preparation (centrifugation at 6000 g for 5 min). At 14 days post-treatment the rats were sacrificed, and blood was collected via the posterior vena cava. At termination, potassium-EDTA anticoagulated whole blood was collected for complete blood count.

Mouse treatments and sample collection. To evaluate the effects of repeated AvFc dosing, mice were randomly assigned to three groups (n=10) and injected subcutaneously with buffer control, 5 mg/kg AvFc, or 20 mg/kg AvFc, twice a week for 5 weeks. Mouse weights were assessed before each injection. The animals were sacrificed on day 35, and blood was collected from the inferior vena cava. Kidneys, livers, spleens, hearts, and lungs were excised, weighed, fixed in 10% buffered formalin for 16 h, and placed in 70% ethanol until use.

Hematology parameters and serum chemistry. Complete blood count was carried out in a blinded manner for mouse samples (n=10) on a Hemavet 950 system (Drew Scientific) standardized for mouse blood. The following parameters were quantified in potassium-EDTA anticoagulated whole blood: red blood cell count (RBC; $10^4$/μl), total and differential leukocyte counts (neutrophils, lymphocytes, monocytes, eosinophils, and basophils quantitated as $10^3$/μl or %), hemoglobin concentration (HGB; g/dl), hematocrit (HCT; %), mean corpuscular volume (MCV; fl), mean cell hemoglobin (MCH; pg), mean cell hemoglobin concentration (MCHC; g/dl), red cell distribution width (RDW; %), platelet count (PLT; $10^4$/μl), and mean platelet volume (MPV; fl). Levels of the following serum chemistry parameters were assessed, with the differences analyzed by two-way analysis of variance (ANOVA): serum albumin (Alb), alkaline phosphatase (ALKP), amylase (Amy), alanine aminotransferase (ALT), blood urea nitrogen (BUN), calcium (Ca), cholesterol (Chol), creatinine (Creat), globulin (Glob), glucose (Glu), phosphorus (Phos), total bilirubin (TBil), and total protein (TP).

Immunoassays for Avaren and AvFc quantitation in serum samples. Avaren and AvFc concentrations were quantitated in serum samples by enzyme-linked immunosorbent assays (ELISAs). For AvFc, 96 well plates were coated with 50 μl/well of 0.3 μg/ml gp120 (Protein Sciences, USA). After overnight incubation at 4° C., plates were blocked with 5% non-fat dry milk in PBS containing 0.05% Tween 20 (PBS-T). Then, samples diluted at 1:50-1:500 in blocking buffer were added and incubated at 37° C. for 1 h. AvFc was detected by mouse anti-Human IgG (Fc) conjugated to horse radish peroxidase (HRP) from Southern Biotech (USA). Plates were developed with SureBlue TMB Microwell Peroxidase Substrate, and reactions were stopped with 1N $H_2SO_4$. Finally, absorbance at 450 nm and 570 nm was measured on a BioTek Synergy HT plate reader. Avaren detection was carried out by sandwich ELISA using a mouse monoclonal anti-Avaren IgG and guinea pig anti-AH serum (produced in our laboratory) as capture and detection antibodies, respectively. Goat anti-guinea pig IgG conjugated to HRP (Santa Cruz, Texas) was used as secondary antibody, and Avaren quantification was similar to what described for AvFc. Serial dilutions of purified AvFc or Avaren were run in parallel to generate the respective standard curves.

Figure 1B:
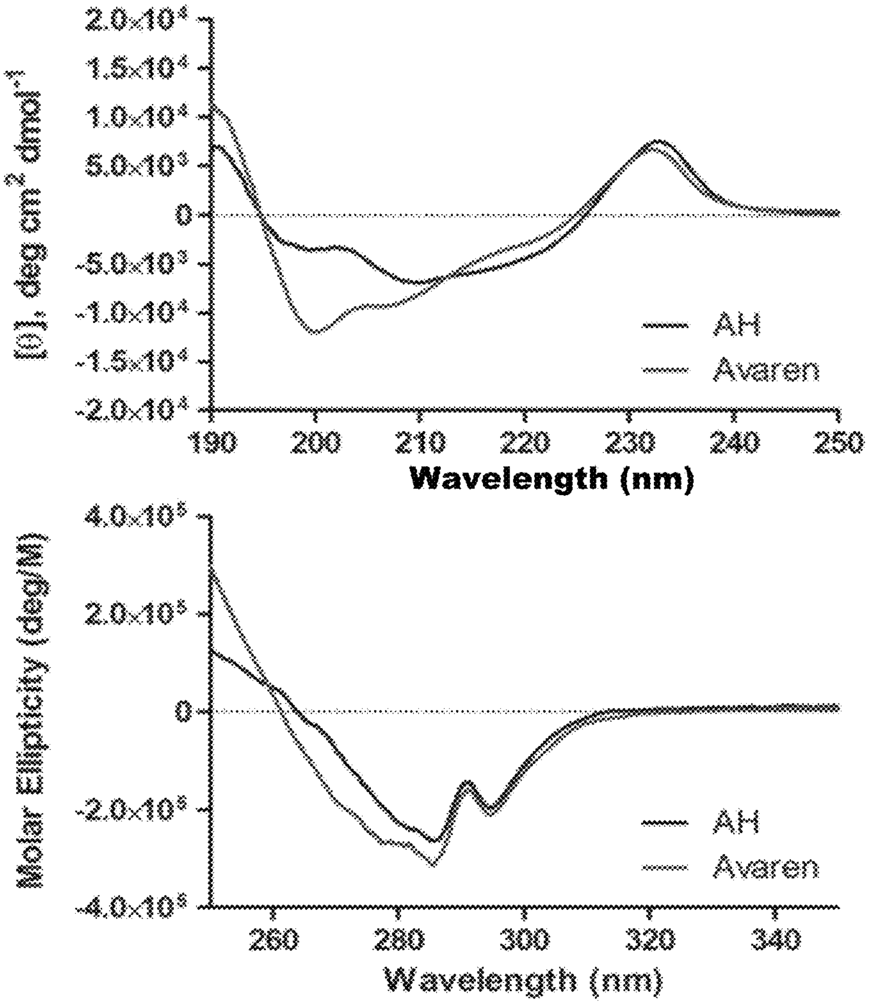
Figure 1C:
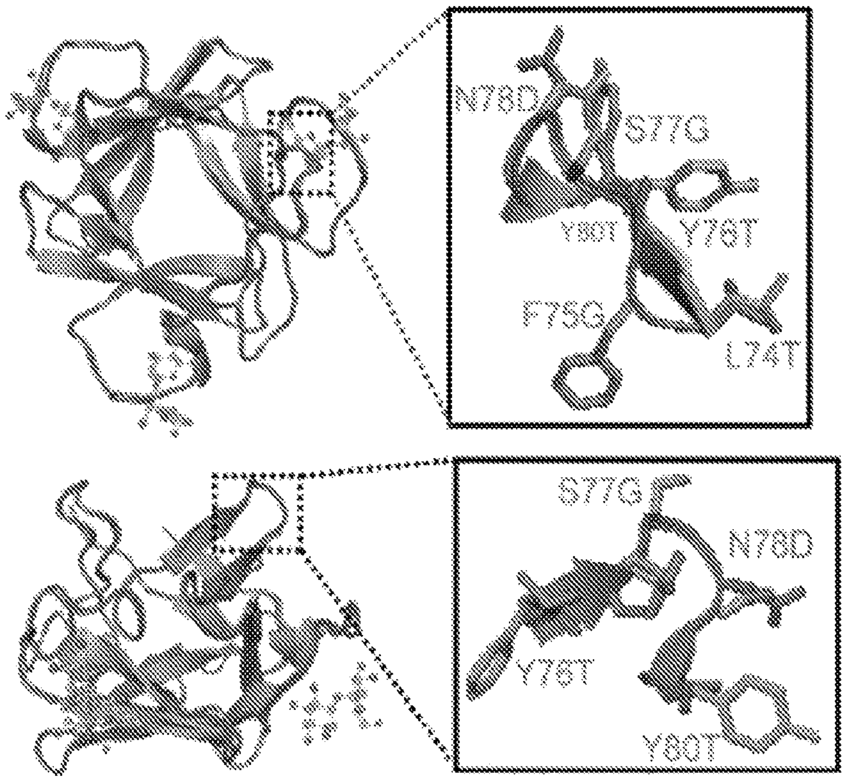
Figure 4B:
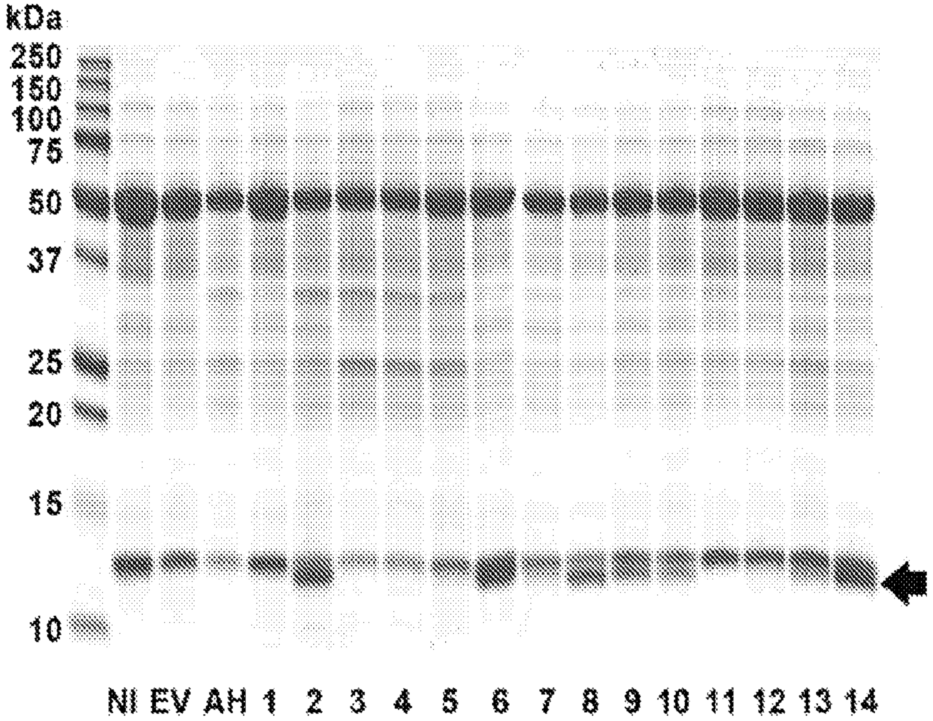
Figure 4C:
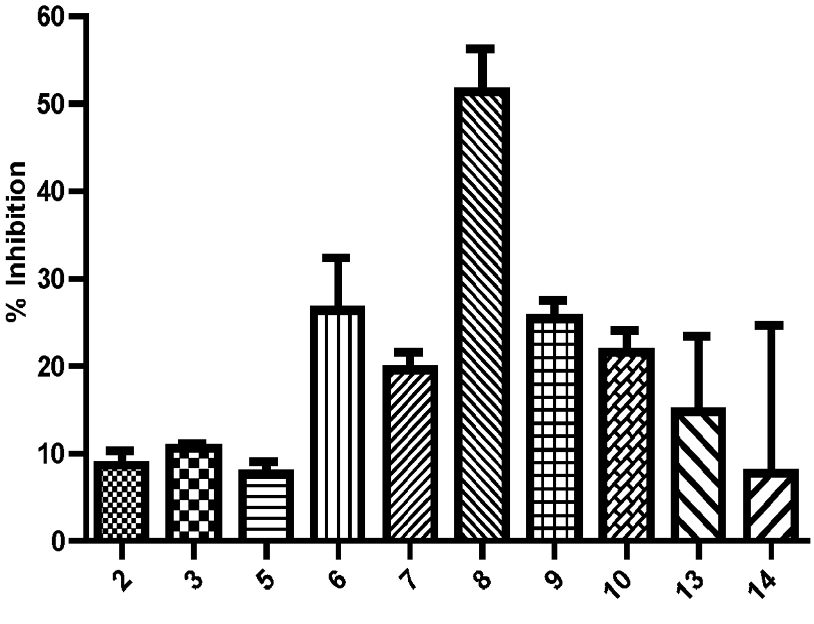
Figure 5:
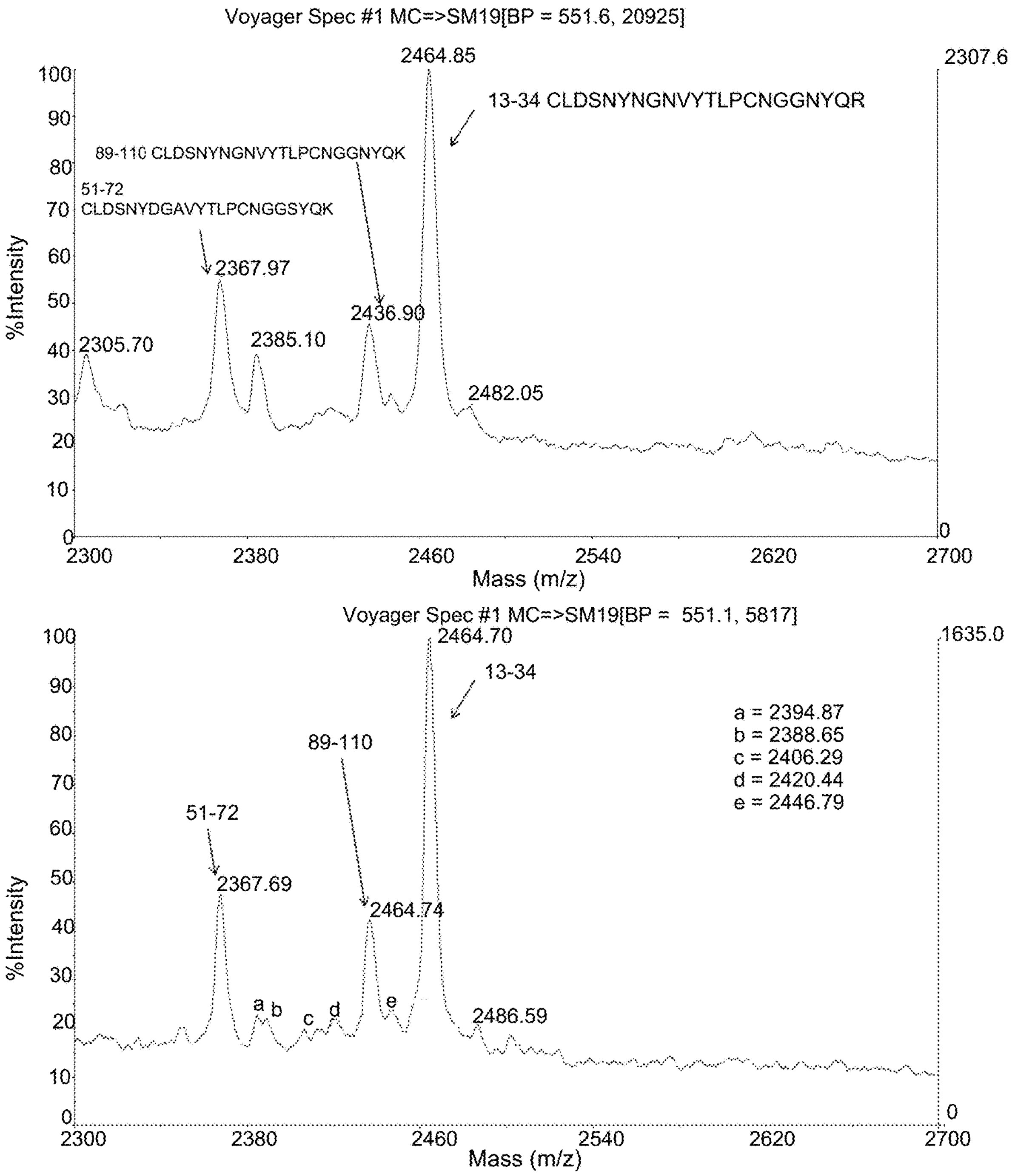
FIG. 5 includes graphs showing Matrix Assisted Laser Desorption Ionization Time-of-flight Mass Spectrometry (MALDI-TOF MS) analysis of Avaren, where purified Avaren was first digested with trypsin and an aliquot was analyzed by MALDI-TOF, where the half of the remaining tryptic digest was reduced with DTT and alkylated with iodoacetamide, and the other half was alkylated only without reduction (Top: The three peptides after digestion (reduced with DTT and alkylated with iodoacetamide, which alone provided evidence that the two Cys in each peptide were not bound to Cys in a different peptide; Bottom: Alkylation without reduction shows no change, suggesting that the Cys residues are not free but part of a disulfide bond).

Statistical analyses. Group means and standard errors were derived from the values obtained in three individual replicates, and assays were performed at least twice independently unless otherwise noted. For all data, outliers were determined by statistical analysis using the Grubb's test ($P<0.05$) and excluded from further analysis. Statistical significance was analyzed by one-way analysis of variance (ANOVA) with Bonferroni's posttests or Wilcoxon matched-pairs signed rank test as indicated in figure legends, using GraphPad Prism 5 (San Diego, CA). Differences were considered statistically significant if $P<0.05$ Results and Discussion AH (SEQ ID NO: 1) is composed of three near-homologous tandem repeats of a 38-amino-acid domain harboring a binding pocket for an α-1,2-linked mannobiose moiety of HMGs. Fourteen AH variants (SEQ ID NOS: 2-15) were designed by changing amino acids in one or two domains to corresponding residues in the other domain(s), such that all three domains were alike and had similar overall surface charge properties. For example, Gln9 (Domain 1) and Gln47 (Domain 2) were mutated to Glu to correspond to Glu85 in Domain 3 (FIG. 4A). To screen the variants, a plant virus vector-based transient overexpression system (magnICON®) was employed. Five days post vector inoculation (dpi), ten variants accumulated much higher than AH in *N. benthamiana* leaf tissue (FIG. 1A and FIG. 4B). Enzyme-linked immunosorbent assays (ELISA; FIG. 1A) showed that Variant 8 (SEQ ID NO: 9) accumulated at the highest level and retained gp120-binding capacity (FIG. 1A) and anti-HIV activity (FIG. 4C). This variant, named Avaren (actinohivin variant expressed in *Nicotiana*), has 17 of 114 amino acids changed from AH. Additionally, a disulfide bond was introduced at the rim of the sugar-binding pocket in Domains 1 and 3, as originally found in Domain 2 (confirmed by peptide mapping; FIG. 5). Circular dichroism (CD) analysis revealed an increase of random coils in Avaren's structure (FIG. 1B, upper panel). Nevertheless, the overall structure appeared to be similar to that of AH (FIG. 1B, lower panel). Homology modeling showed closely superimposed structures of AH and Avaren albeit a loss of a P-strand in the hinge between Domain 2 and 3 of Avaren (FIG. 1C). The melting temperatures of Avaren and AH determined by CD were both 72.9° C., indicative of their similar structural stability. Collectively, Avaren has a better recombinant producibility in plants than AH, while retaining overall conformational and functional properties.

Figure 1D:
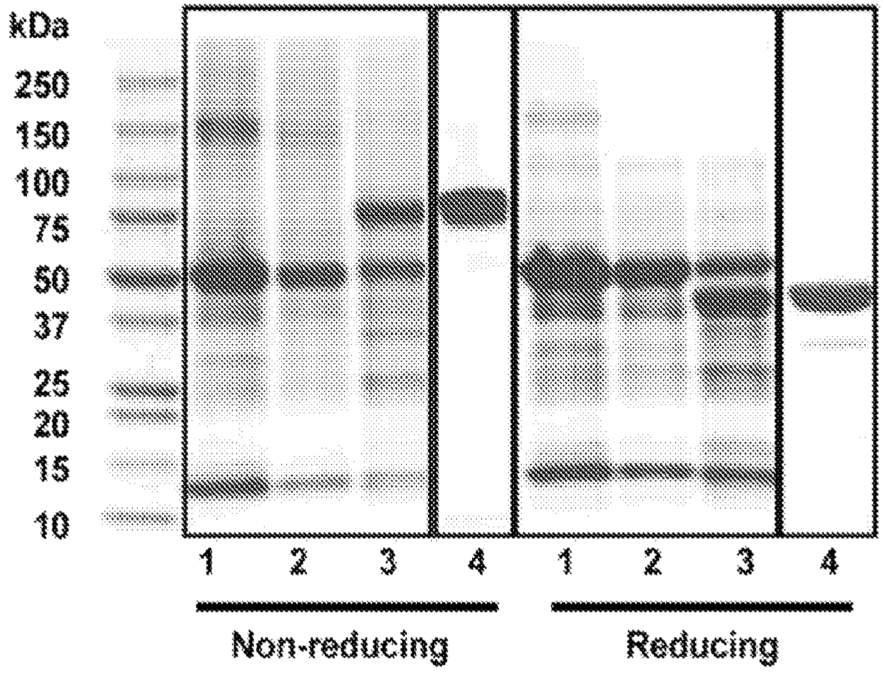
Figure 1E:
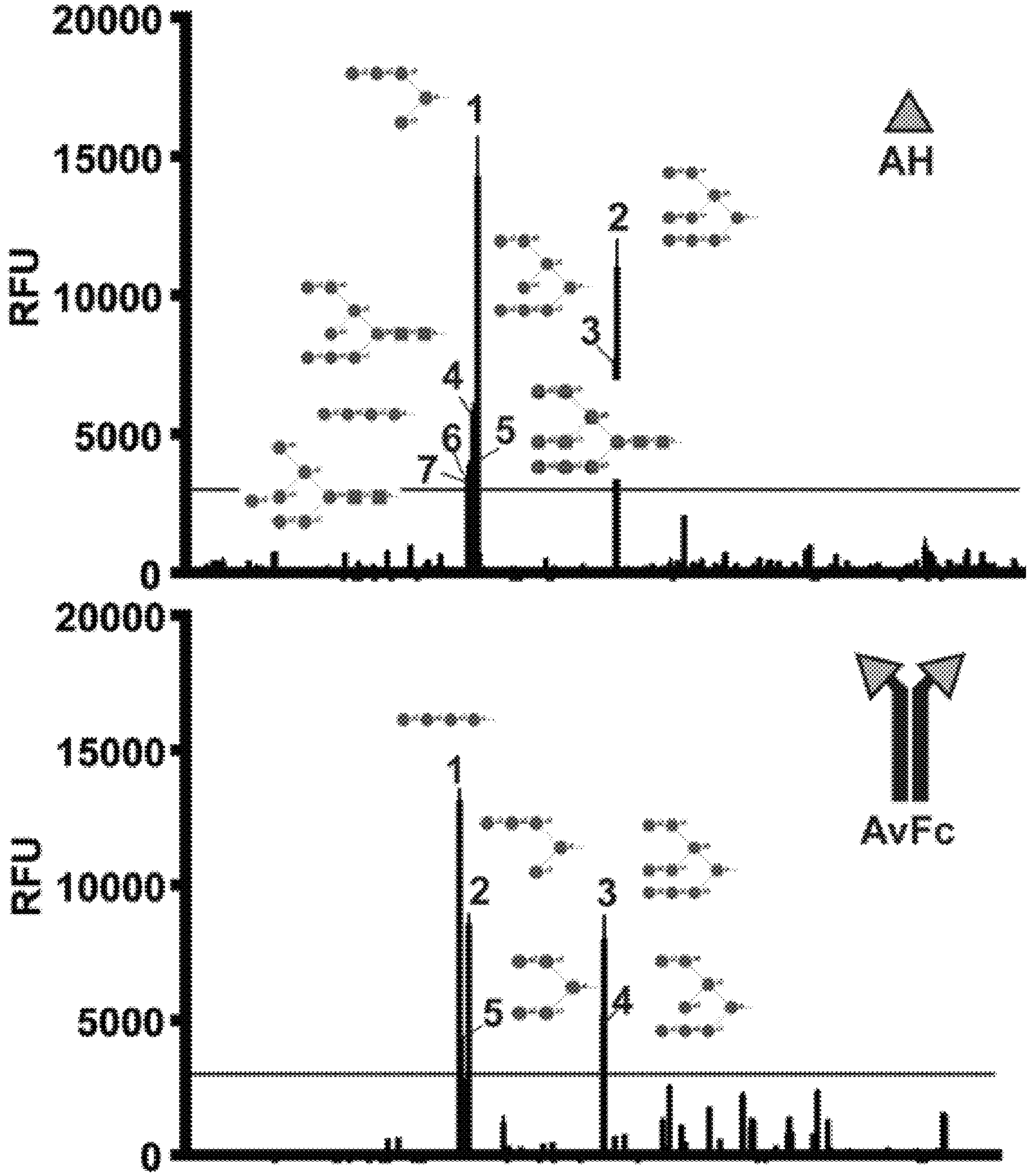
Figure 6:
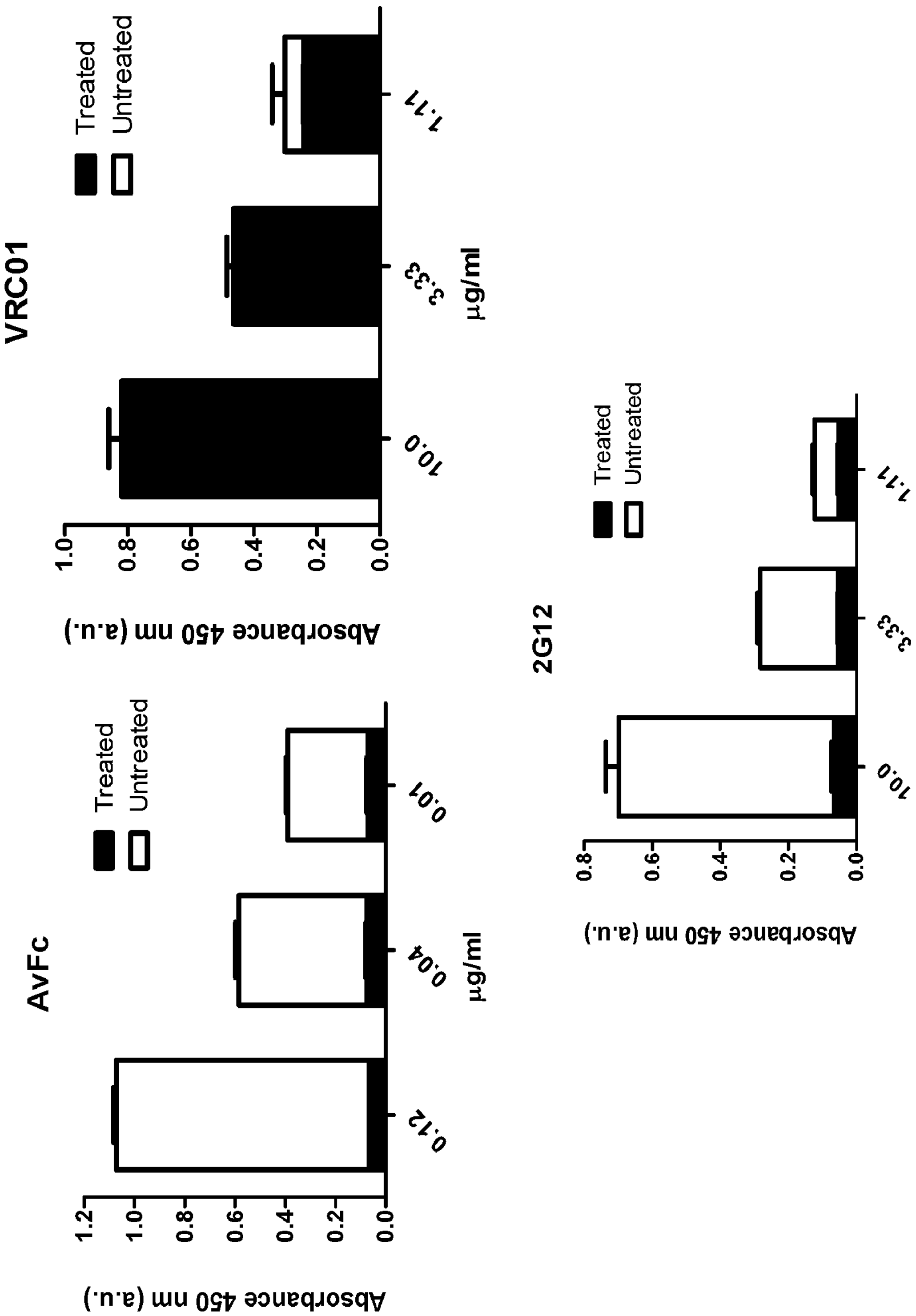
FIG. 6 includes graphs showing the analysis of AvFc's binding to gp120 treated with α-mannosidase, where the gp120-binding ELISA was performed on AvFc, VRC01 (a HIV-1 CD4 binding site-specific monoclonal antibody) and 2G12 (a HIV-1 envelope HMG-binding monoclonal antibody), using a recombinant HIV-1 gp120 or gp120 treated with α (1-2,3,6) mannosidase, where the gp120-binding activities of AvFc and 2G12, but not VRC01, were abolished by treating the Env protein with the α-mannosidase, demonstrating AvFc's specificity to the mannobiose moieties of HMGs.

To further enhance the drug potential of Avaren, it was genetically linked to the Fc region of a human IgG1 antibody (AvFc; SEQ ID NO: 16), because such a "lectibody" molecule may possess advantages over the parent lectin, including higher HMG affinity via dimerization, prolonged in vivo half-life and Fc-mediated anti-viral/tumor functions such as ADCC. Upon expression in *N. benthamiana* using the plant virus vector, AvFc accumulated ~50% of the total soluble leaf protein in 7 days (FIG. 1D) and was efficiently purified to >95% homogeneity (FIG. 1D, lane 4). Approximately 1 g of purified AvFc was obtained from 10 kg of plant biomass in a pilot-scale production facility. To determine AvFc's sugar binding specificity, a glycan array analysis was performed. Among 610 glycans analyzed, both AH and AvFc showed high specificity to oligomannose glycans containing terminal α-1,2-linked mannose (FIG. 1E). These results were corroborated by ELISA, in which the lectibody's binding was abrogated upon treating gp120 with a mannosidase (FIG. 6).

Figure 1F:
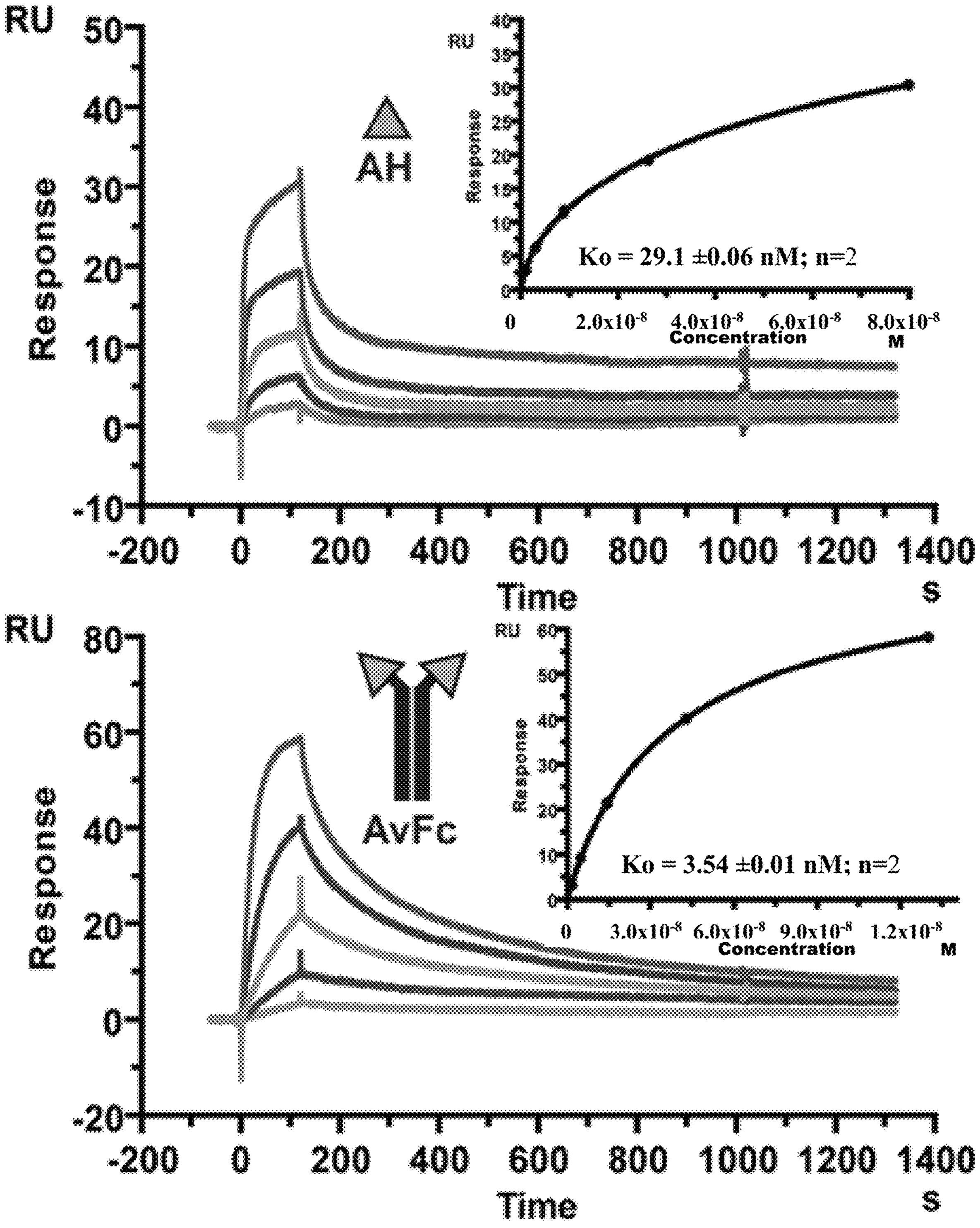
Figure 1G:
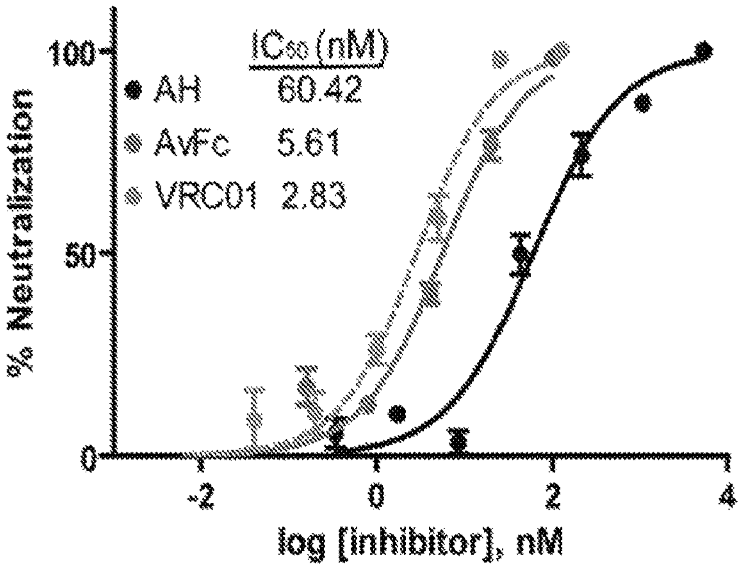
Figure 2A:
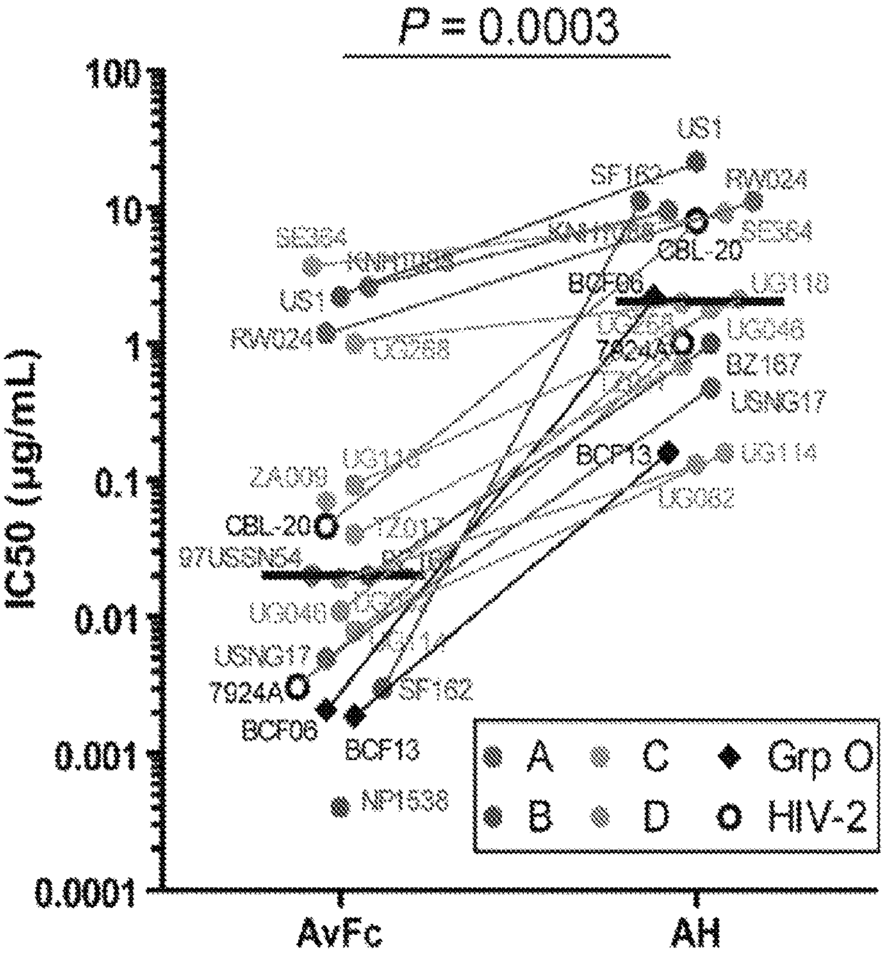
FIGS. 2A-2G includes graphs and images showing that AvFc potently neutralizes multiple HIV strains and recognizes various cancer cells and tumors, including.
Figure 2B:
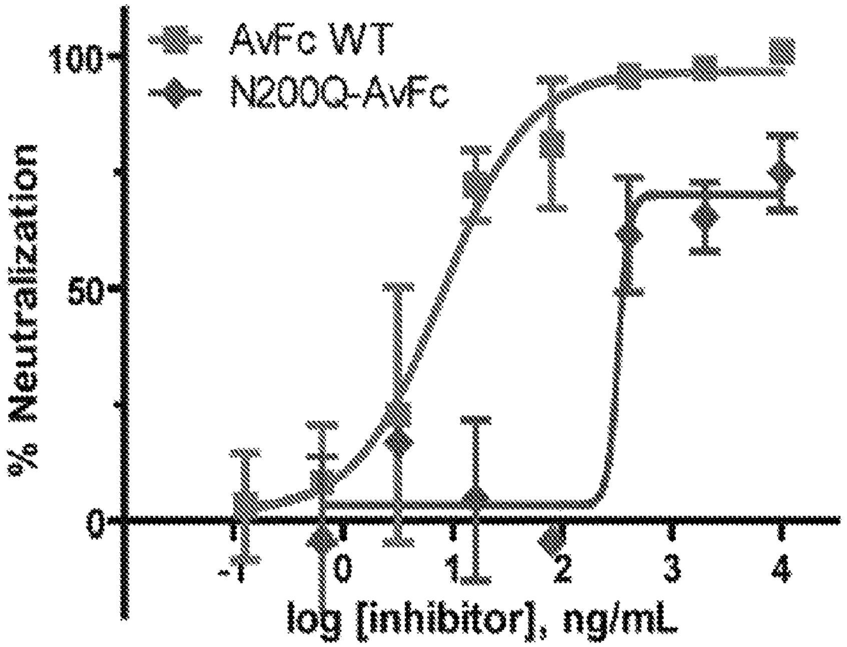
Figure 2C:
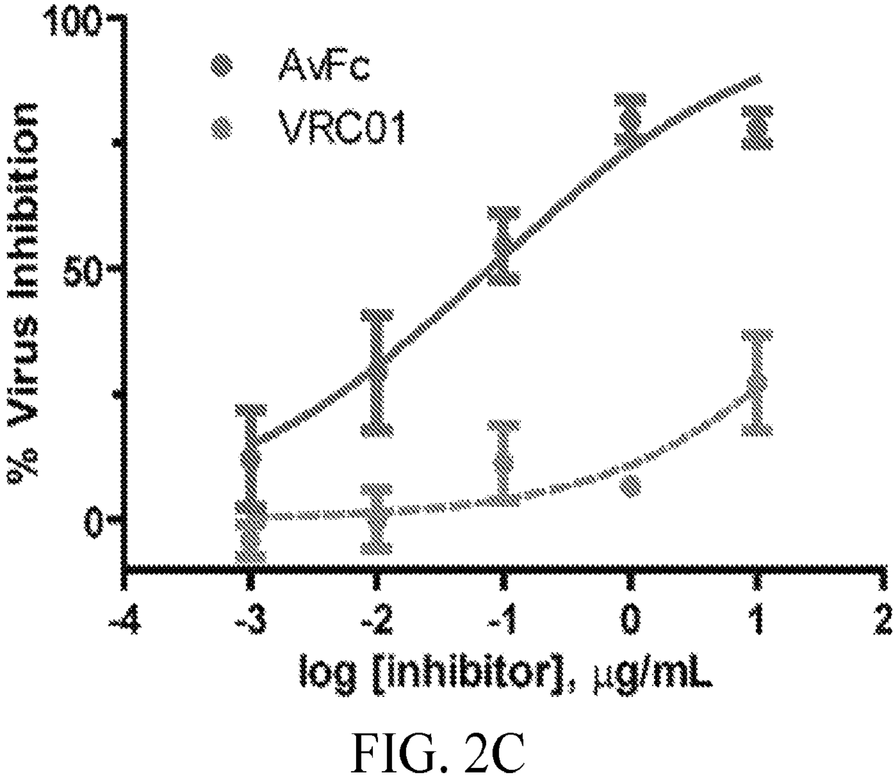
Figure 7:
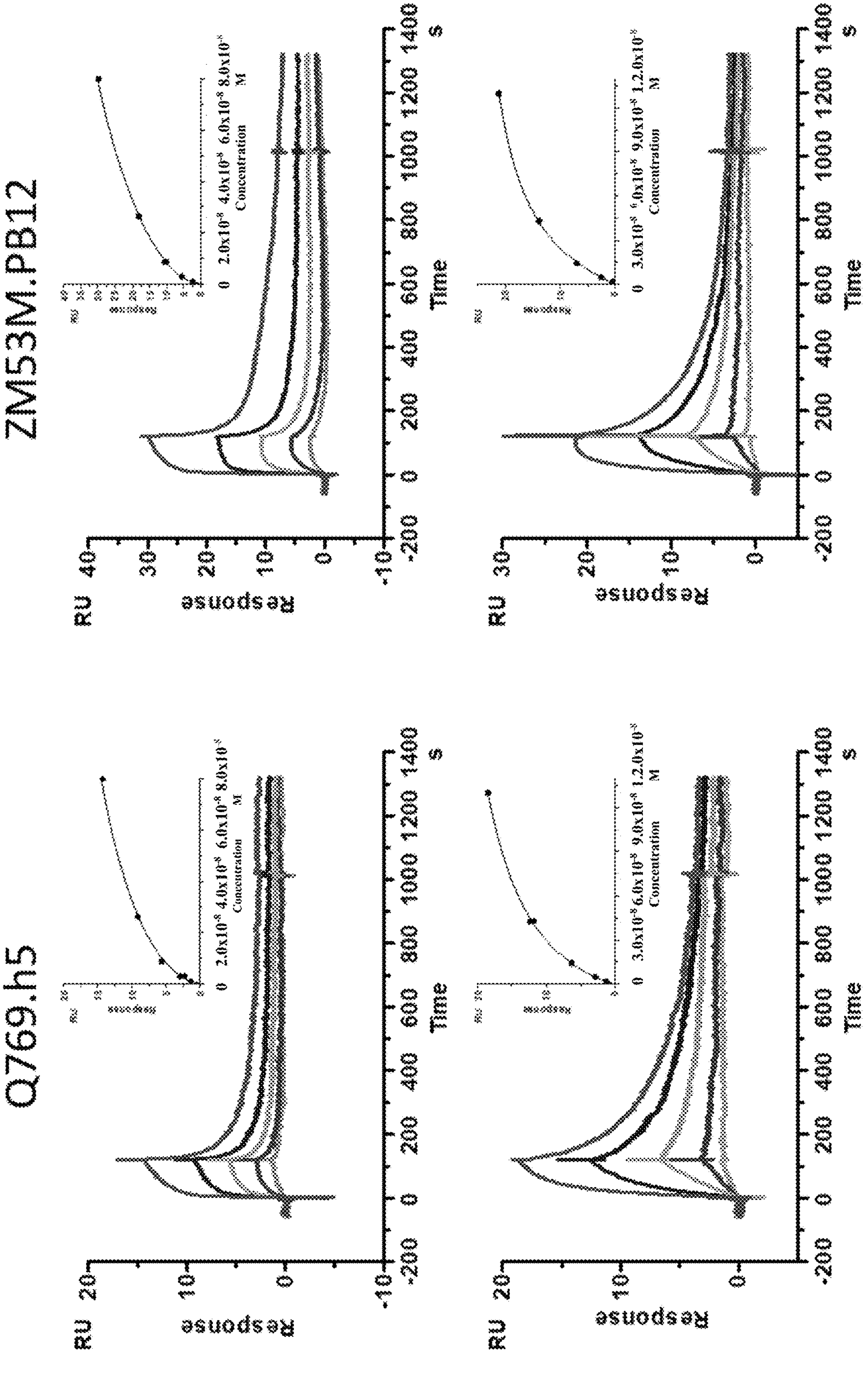
FIG. 7 includes graphs showing surface plasmon resonance analysis of the binding affinities of AH and AvFc to gp120 proteins, where the binding affinity ($K_D$) of AH (top) and AvFc (bottom), to $gp120_{(Q769.h5\ or\ ZM53M.PB12)}$ were measured using a Biacore X100 2.0 instrument at ambient temperature, where, for each protein, the assay was performed in duplicate, where representative sensorgrams are shown, where recombinant His-tagged $gp120_{(Q769.h5\ or\ ZM53M.PB12)}$ was captured on a sensor chip NTA following the manufacturer's instructions to a surface density of about 50-100 RU, where three fold serial dilutions of AvFc (1 μg/ml to 0.0123 μg/ml) or AH (1 μg/ml to 0.0123 μg/ml) were made in running buffer (HPS-P+ with 50 μM EDTA) and injected, at a flow rate of 5 μl/min, where the equilibrium dissociation constant $K_D$ was determined based on steady state (inset), where the $K_D$ values for AH and AvFc to $gp120_{Q769.h5}$ were determined to be 29.6±1.4 nM and 4.2±0.6 nM, respectively, where the $K_D$ values for AH and AvFc to $gp120_{ZM53M.PB12}$ were determined to be 35.7±0.1 nM and 4.4±0.2 nM, respectively, and where data are expressed as mean±SEM from two independent analyses.
Figure 8A:
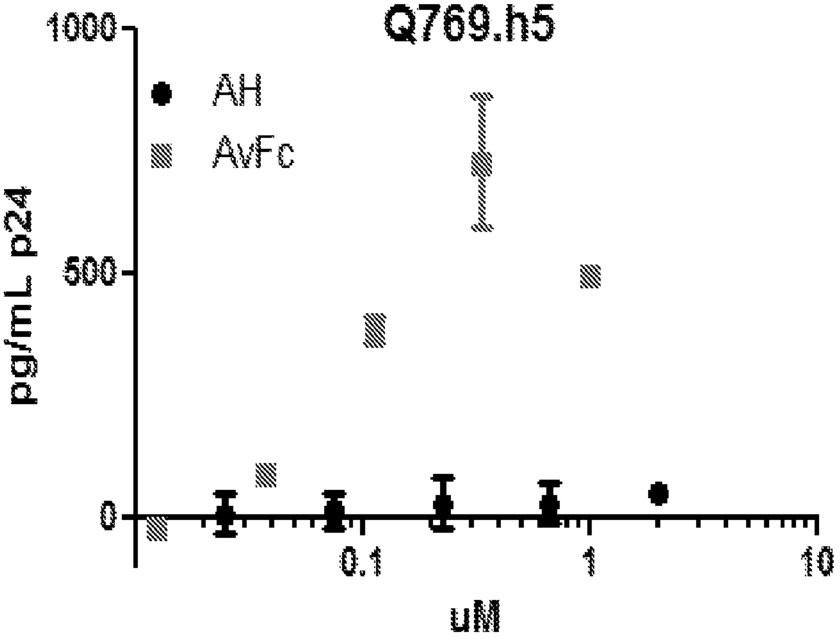
FIGS. 8A-8C are graphs showing a HIV-1 virus capture assay, where AH or AvFc were serially diluted and coated on a 96-well polystyrene plate and blocked with DMEM culture media containing 10% FBS, where Env-pseudotyped viruses (Q769.h5—Clade A (FIG. 8A), SF162—Clade B (FIG. 8B), or ZM53M.PB12—Clade C (FIG. 8C)) were added to the coated wells and incubated for 1 h at 37° C., where triton X-100 was then added at a final concentration of 1% to lyse the captured virions and release the core HIV antigen p24, where the lysates were transferred to an anti-p24 coated 96-well plate (Sino Biologicals, China), and where the sandwich ELISA was conducted according to the manufacturer's directions and the captured p24 was quantified based on a standard curve using the GraphPad Prism software.
Figure 8B:
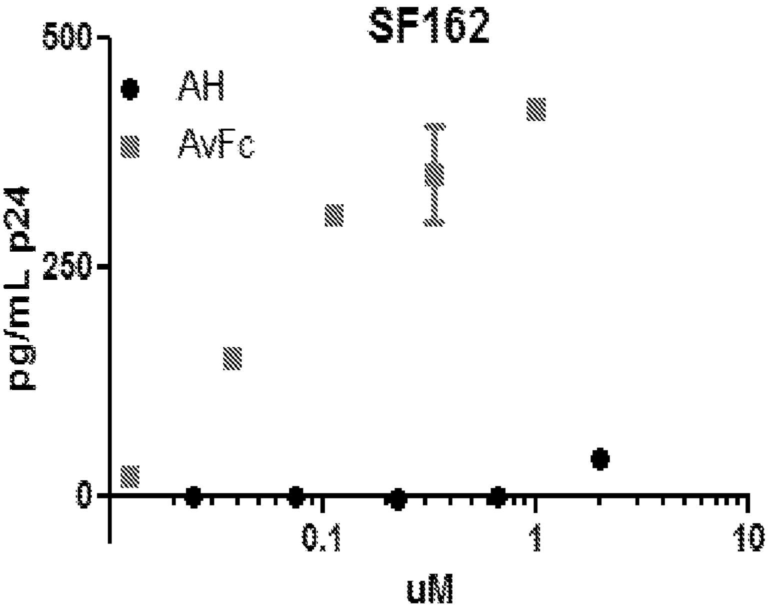
Figure 8C:
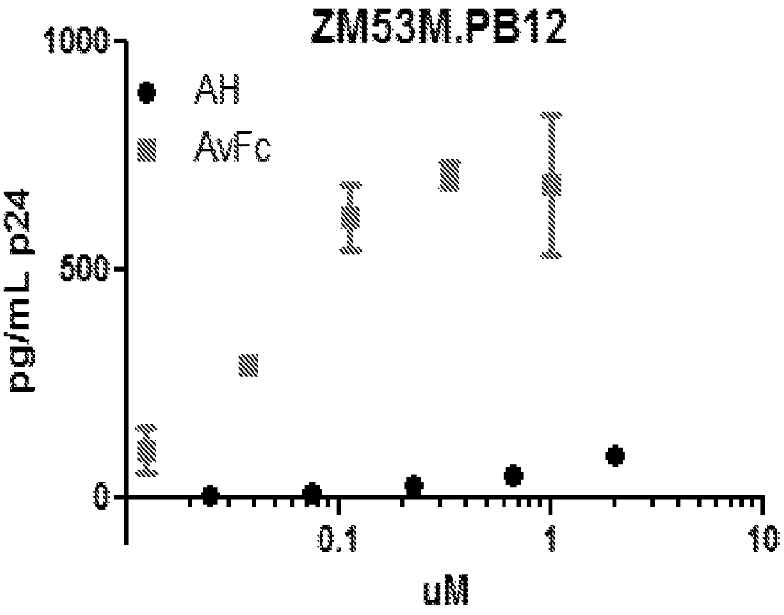
Figure 8D:
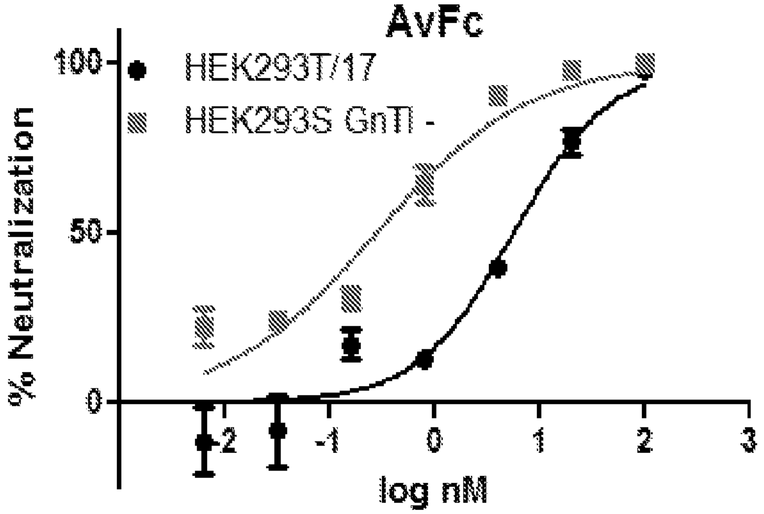
FIGS. 8D-8E are graphs showing Env-pseudotyped HIV-1 neutralization assays, where the assays were performed to determine the impact of the glycan structure of HIV-1 virions on the anti-viral activity of AvFc, where pseudoviruses were produced in HEK293T/17 and HEK293S GnTI—cells to give rise to either complex glycans and HMGs on Env, respectively, where the different pseudoviruses were then added to AvFc or 4E10 (anti-gp41 specific HIV monoclonal antibody) and mixed with HOS cells, where seventy-two h later the cells were lysed and the luciferase activity was determined, and where the reduced $IC_{50}$ for AvFc indicates its specificity for HMGs while the control antibody, 4E10, demonstrated no change in anti-HIV activity.
Figure 8E:
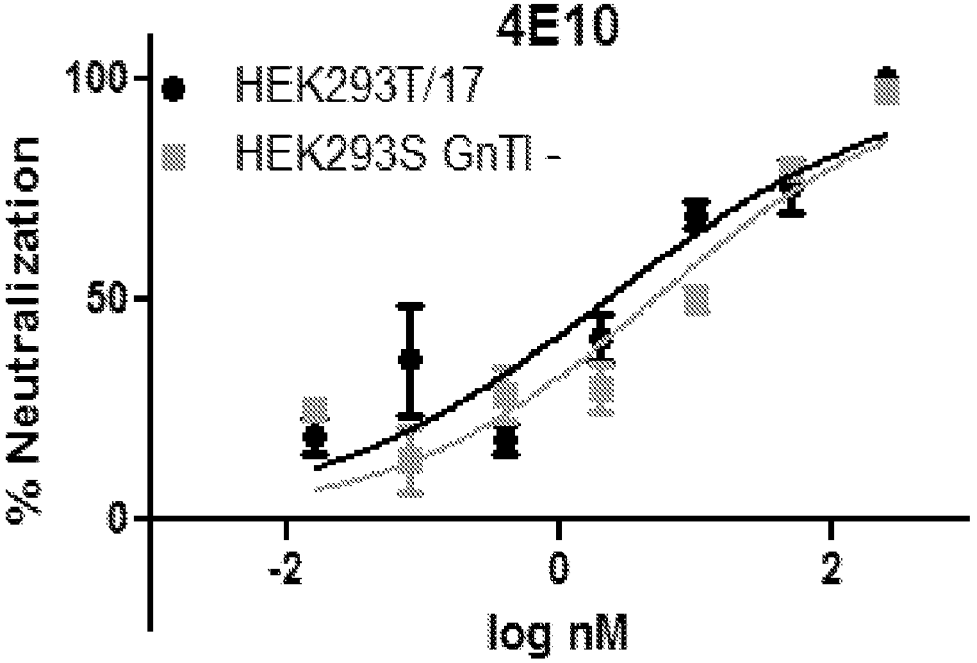
Figure 9A:
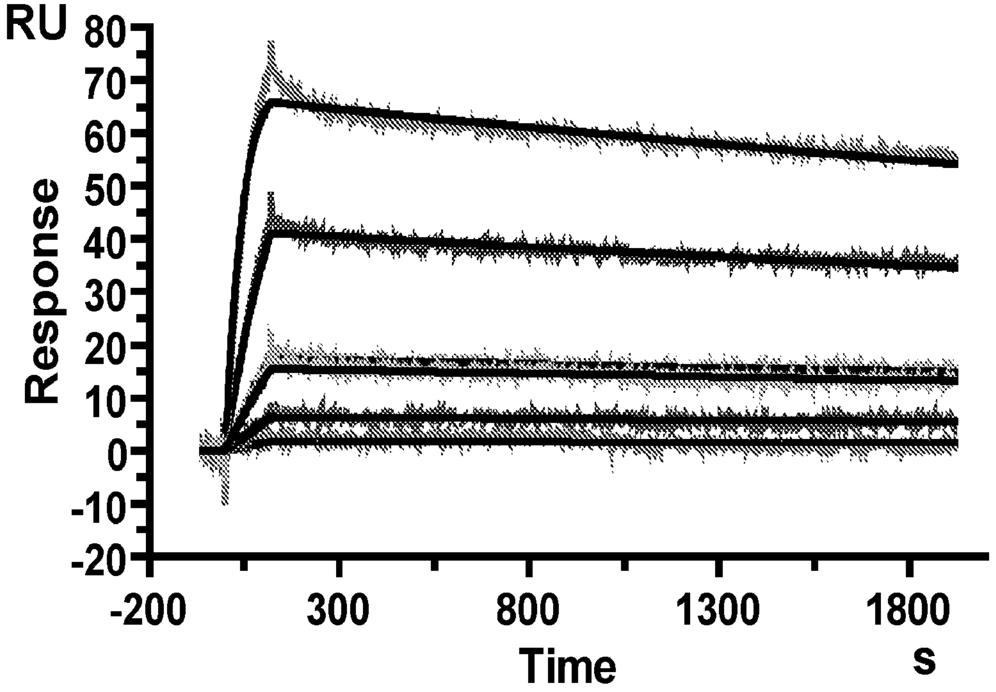
FIGS. 9A-9E include graphs showing an analysis of AvFc's Fc function, including.
Figure 9B:
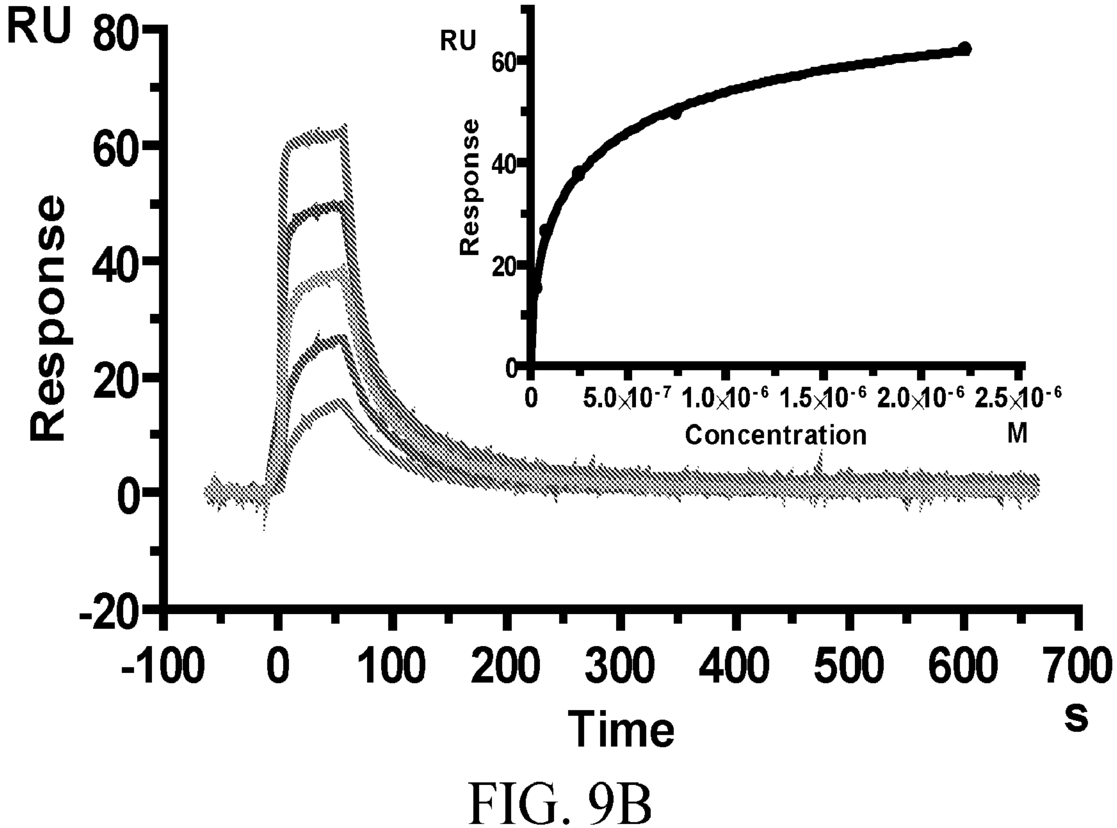
Figure 9C:
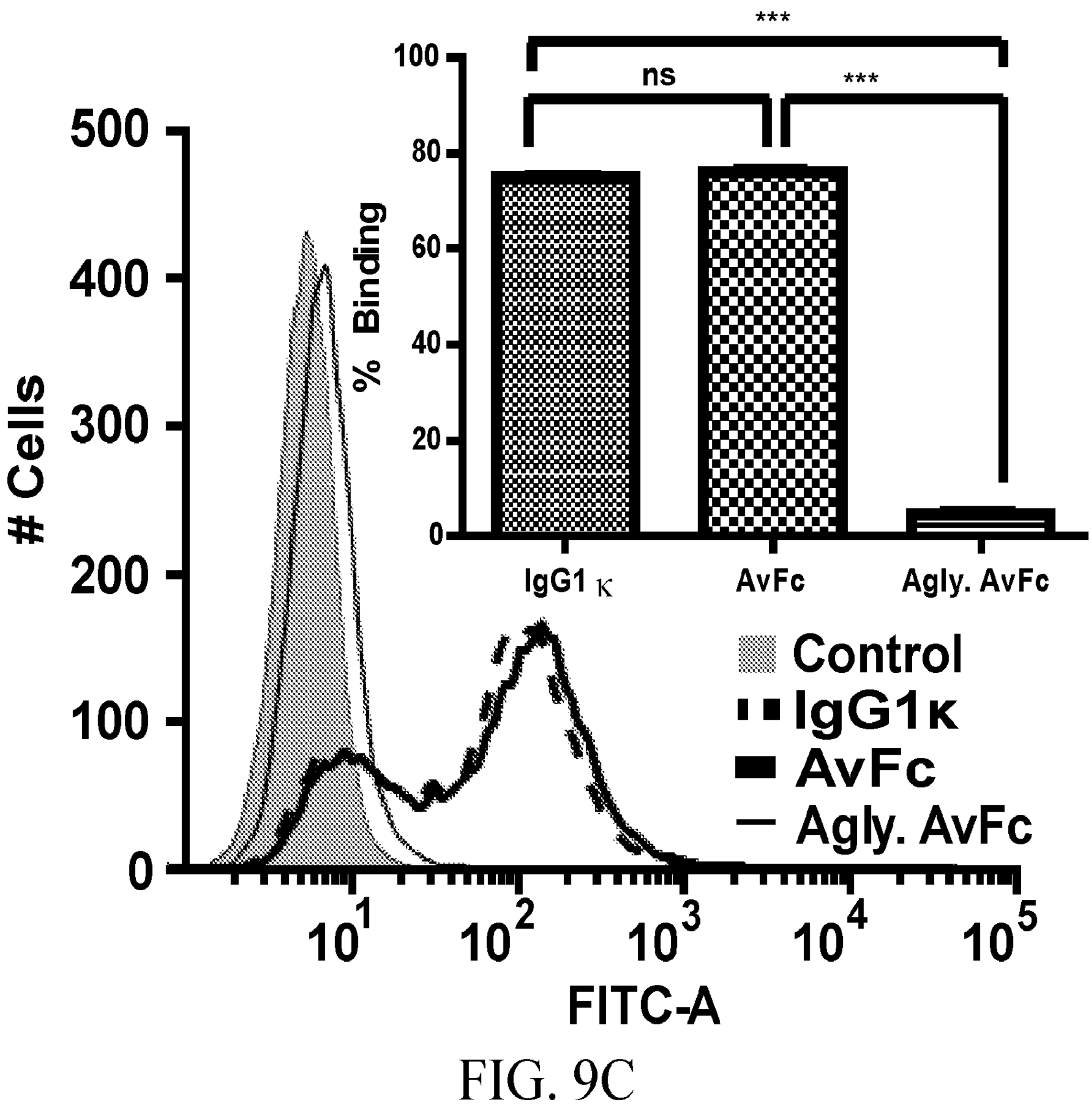
Figure 9D:
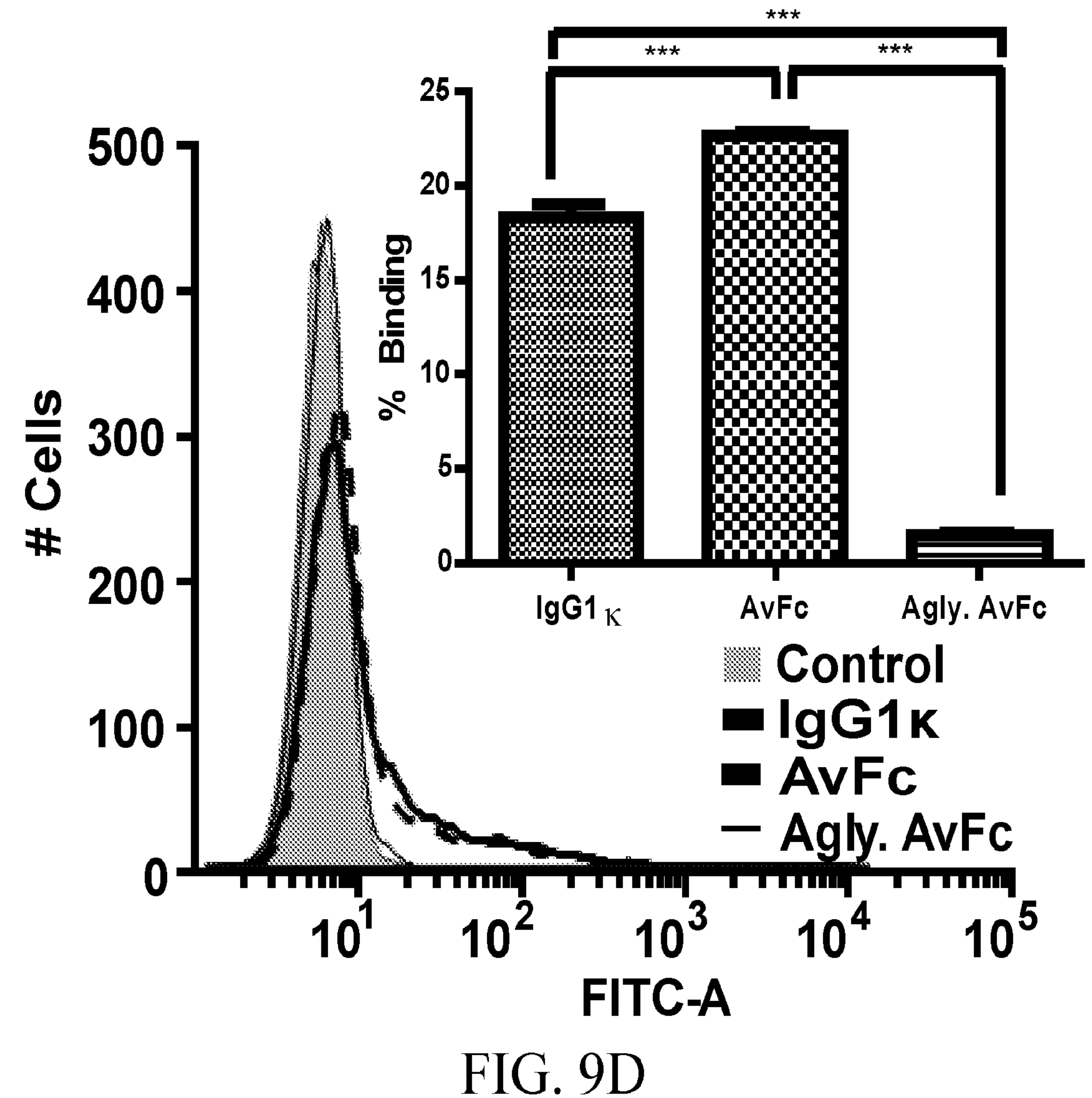

Surface plasmon resonance (SPR) analysis revealed that the lectibody had increased affinity to recombinant HIV gp120 proteins by approximately 10-fold compared to AH (FIG. 1F and FIG. 7). Additionally, AvFc had significantly better capacity to capture HIV virions than AH (FIGS. 8A-8C). HIV-1 envelope-pseudotyped virus neutralization assays showed that AvFc was significantly more potent than AH (FIG. 1G), with neutralization activity enhanced for viruses carrying increased amounts of $Man_{5-9}GlcNAc_2$ oligomannose glycans (FIGS. 8D-8E). In human peripheral blood mononuclear cell (PBMC) infection assays (FIG. 2A), AvFc showed significantly more potent antiviral activity than AH against twenty primary viruses of HIV-1 Groups M and O as well as HIV-2 strains (P=0.0003 Wilcoxon matched pairs test, FIG. 2A). The median 50% inhibitory concentrations ($IC_{50}$s) were 0.3 nM (0.02 μg/mL) for the lectibody, and 156.3 nM (2.00 μg/mL) for AH. Whether AvFc's anti-HIV activity could be in part mediated by the Fc moiety was also investigated. SPR showed that AvFc bound to human Fcγ receptor (FcγR)I and FcγRIIIa with $K_D$ values similar to those of a human IgG1κ isotype control (FIGS. 9A-9B). These findings were confirmed by flow cytometry analysis using FcγRI and FcγRIIIa-expressing cells (FIG. 9C-9D). By contrast, AvFc with Asn200→Gln mutation, which eliminates N-glycosylation in the Fc region corresponding to Asn297 of human $IgG_1$ and thereby significantly reduces affinity to these FcγRs, showed dramatically reduced binding to these receptors. Additionally, this mutation significantly reduced the antiviral activity of AvFc in a human PBMC infection assay (FIG. 2B). Meanwhile, AvFc showed a dose-dependent inhibitory effect in an antibody-dependent cell-mediated virus inhibition (ADCVI) assay using human primary natural killer (NK) cells and HIV-1-infected primary CD4 cells (FIG. 2C). Taken together, AvFc can elicit Fc-mediated antiviral activity in addition to virion neutralization, an unprecedented function for antiviral lectins.

Figure 2D:
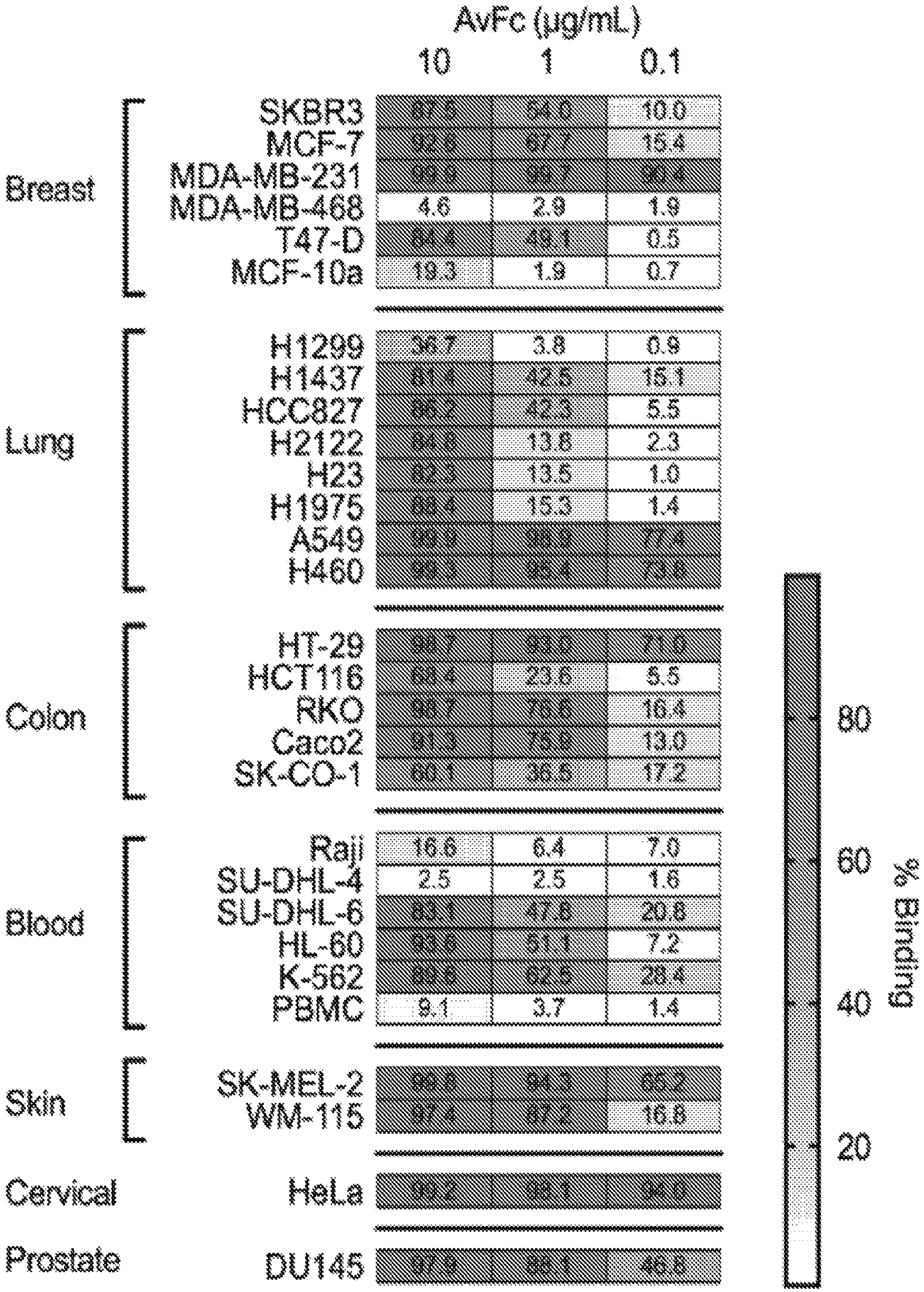
Figure 2E:
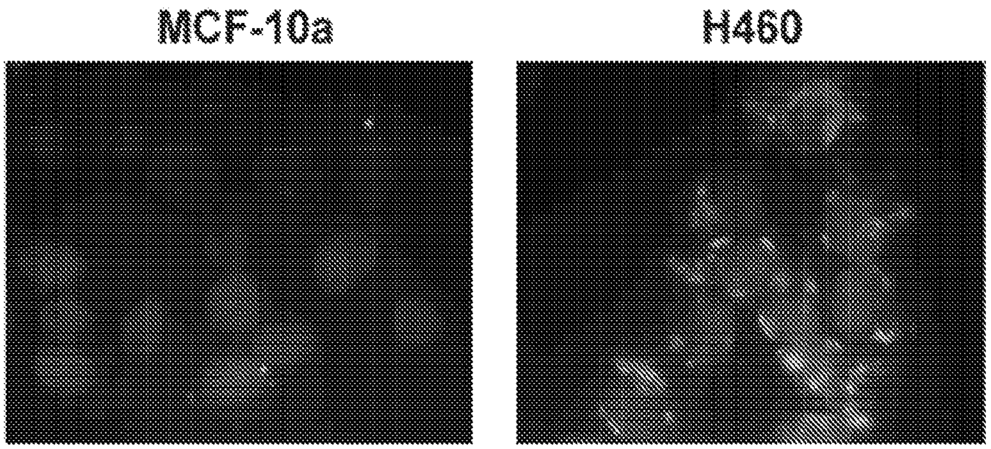
Figure 2F:
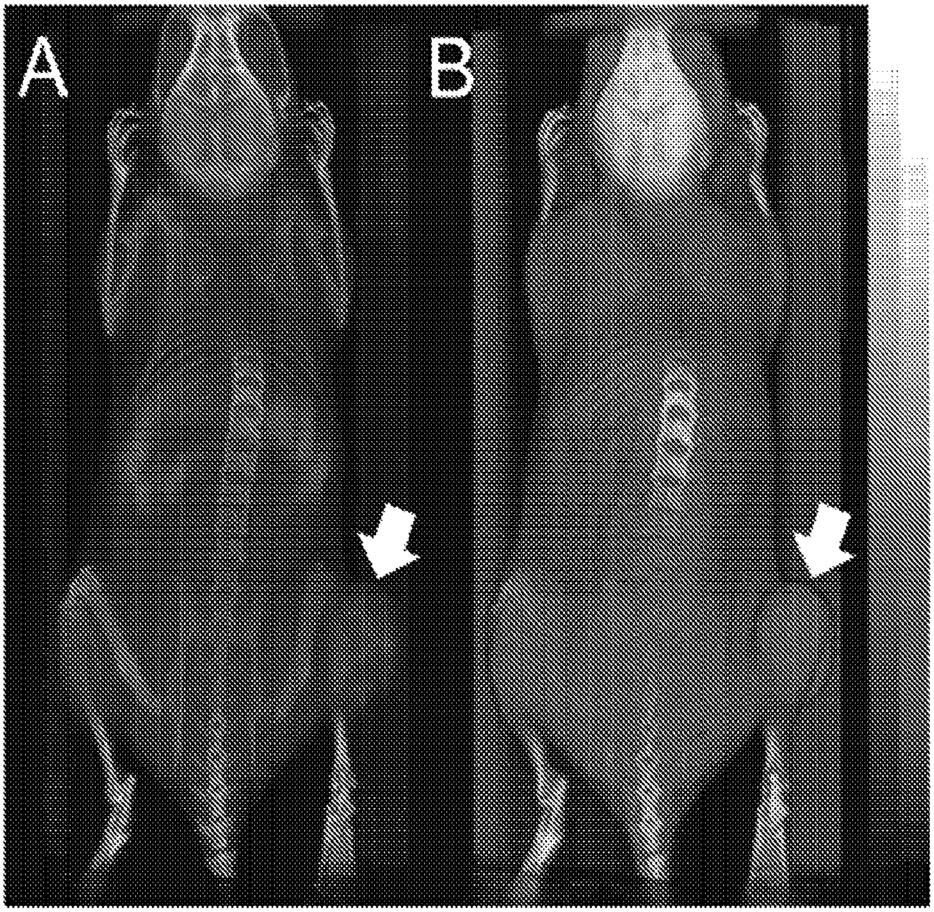
Figure 2G:
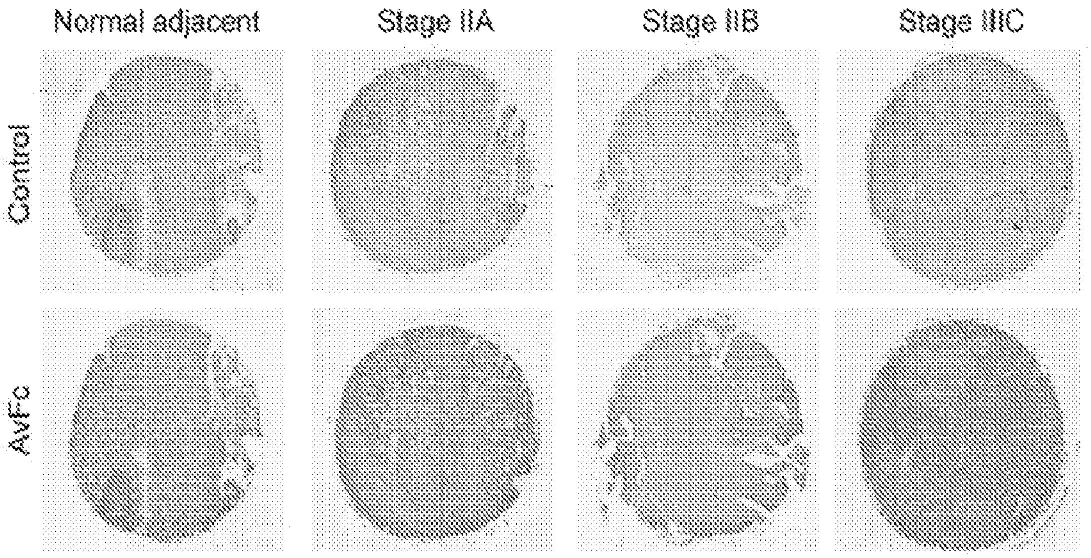
Figure 10A:
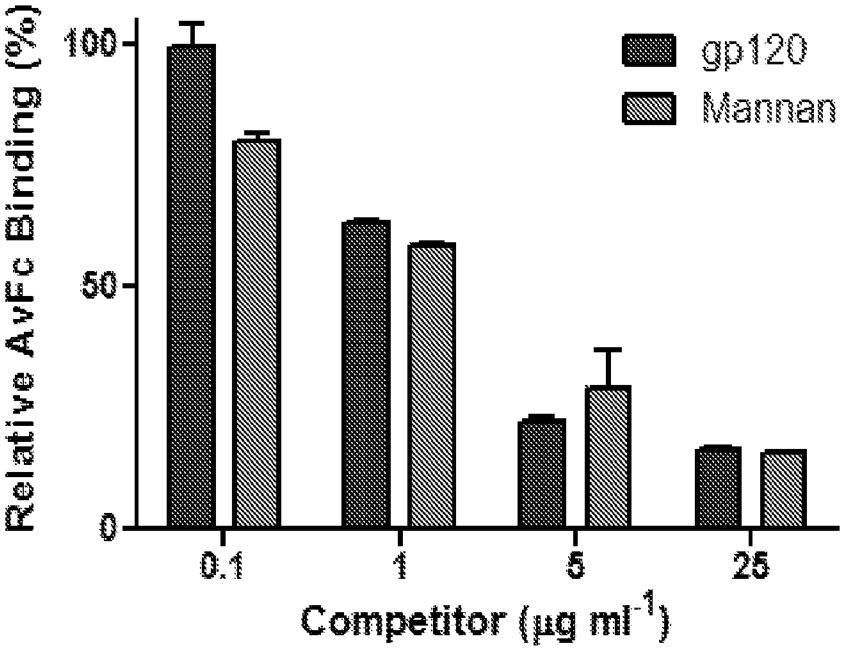
FIGS. 10A-10C are graphs showing inhibition of AvFc binding to cancer cells by HIV-1 gp120 and yeast mannan, including.
Figure 10B:
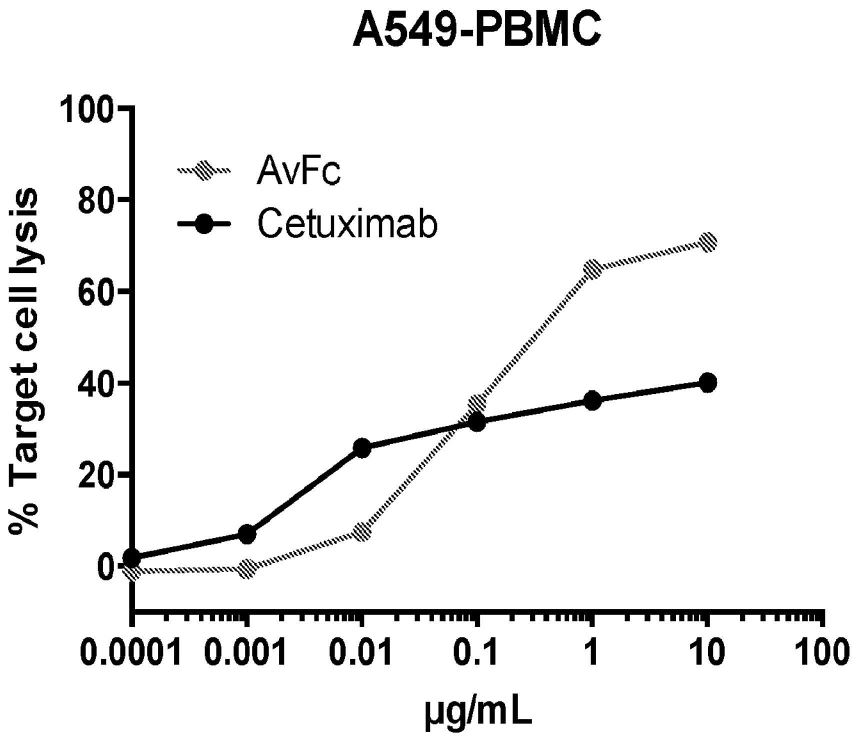
Figure 10C:
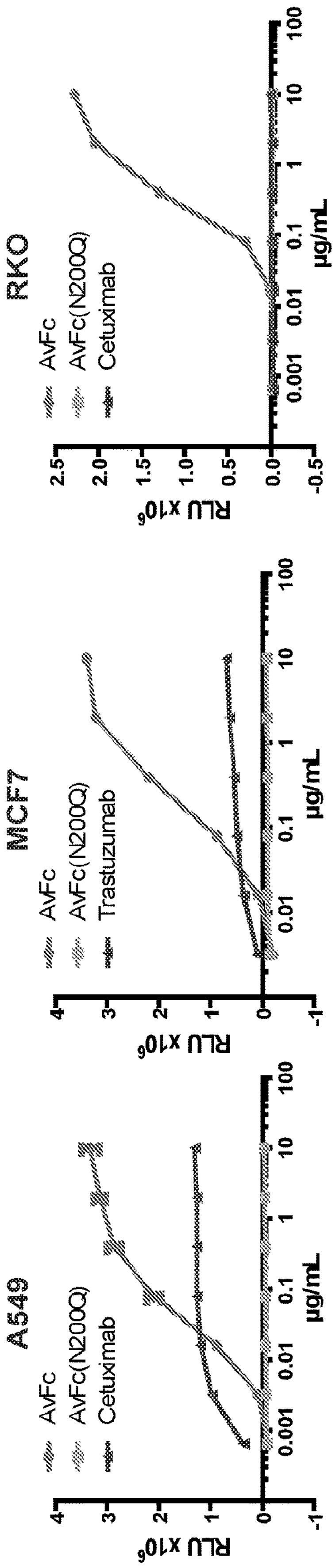

Growing evidence for elevated HMG levels on tumor cell membranes and in the sera of cancer patients then led to tests of AvFc's binding to human cancer cells. In flow cytometry analysis, the lectibody significantly bound to a wide range of cancer cells of breast, lung, colon, blood, cervical and prostate origins at nanomolar concentrations. By contrast, low to negligible binding was noted for a few cancer cell lines and non-tumorigenic cells including human PBMCs (FIGS. 2D-2E). The interaction of AvFc to cancer cells was HMG-specific, as gp120 and mannan effectively competed the binding (FIG. 10A). In a mouse B16F10 melanoma model, the flank tumors were clearly visualized by positron emission tomography-computed tomography (PET-CT) using radiolabeled AvFc as an imaging probe (FIG. 2F). Furthermore, immunohistochemistry using AvFc detected an advanced-stage human colon tumor (FIG. 2G). These results corroborate previous findings that high levels of HMGs are often displayed on neoplastic cells. To test the anti-cancer potential of AvFc, an in vitro ADCC assay was performed using the lung cancer cell line A549 and human primary effector cells. The lectibody induced a potent ADCC activity, which was comparable to that of cetuximab (FIG. 10B). Additionally, AvFc, but not the Asn200→Gln mutant, activated FcγRIIIa in a dose dependent manner upon binding to three different cancer cell lines including A549, MCF7 (breast cancer) and RKO (colon cancer), with 50% effective concentrations in the nanomolar range (FIG. 10C). Collectively, these data indicated the application of AvFc to a new paradigm of anti-cancer strategies targeting tumor-associated HMGs.

Figure 3A:
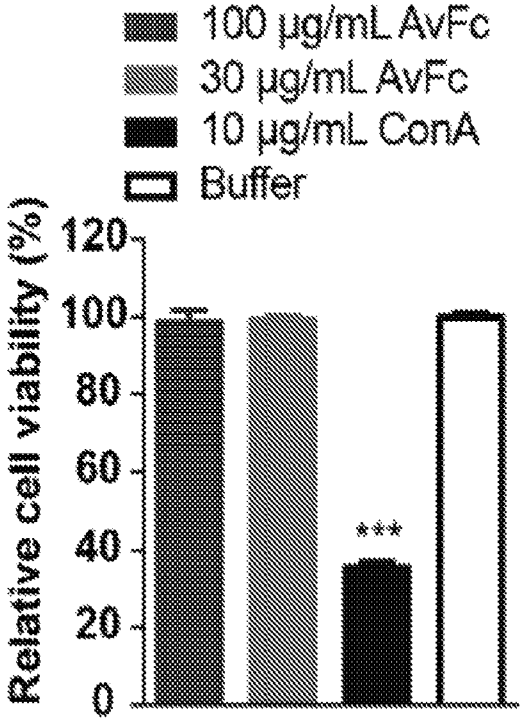
FIGS. 3A-3I includes graphs showing AvFc lacks major toxicity in in vitro and animal models, including.
Figure 3B:
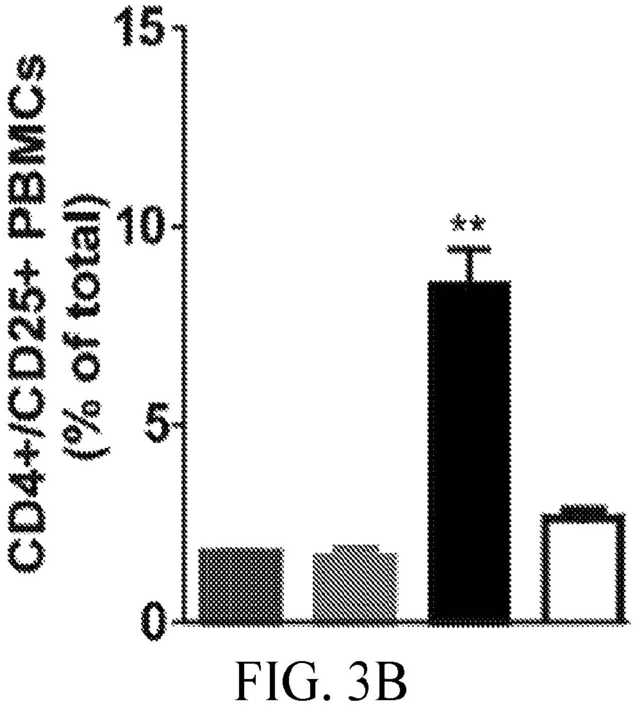
Figure 3C:
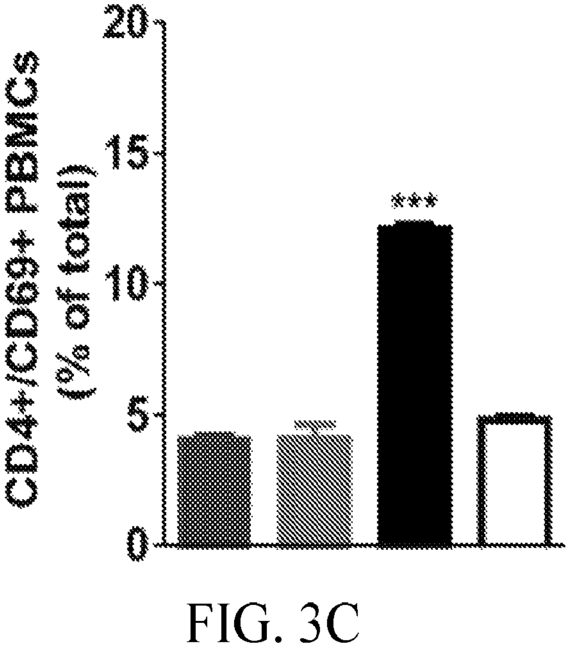
Figure 3D:
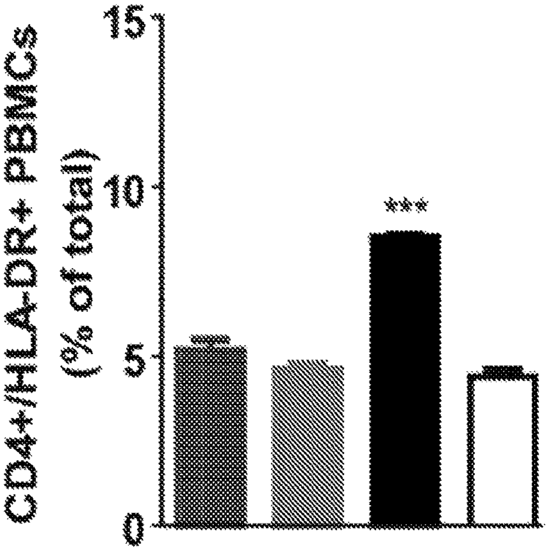
Figure 3E:
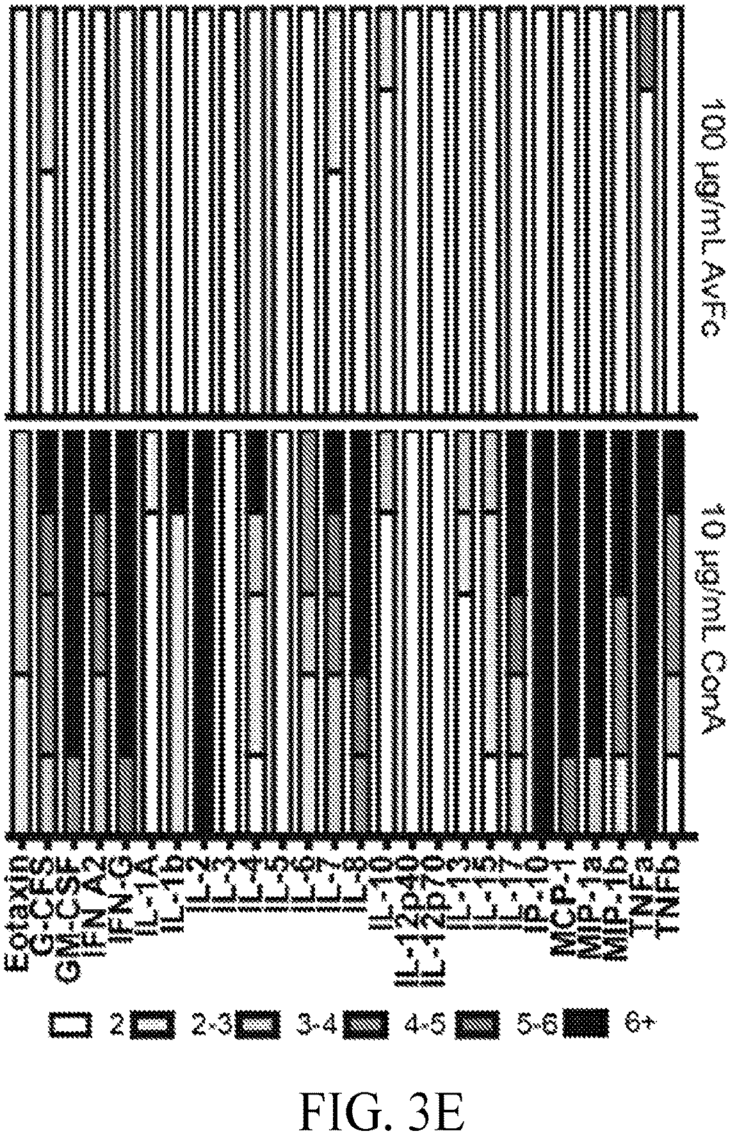
Figure 3F:
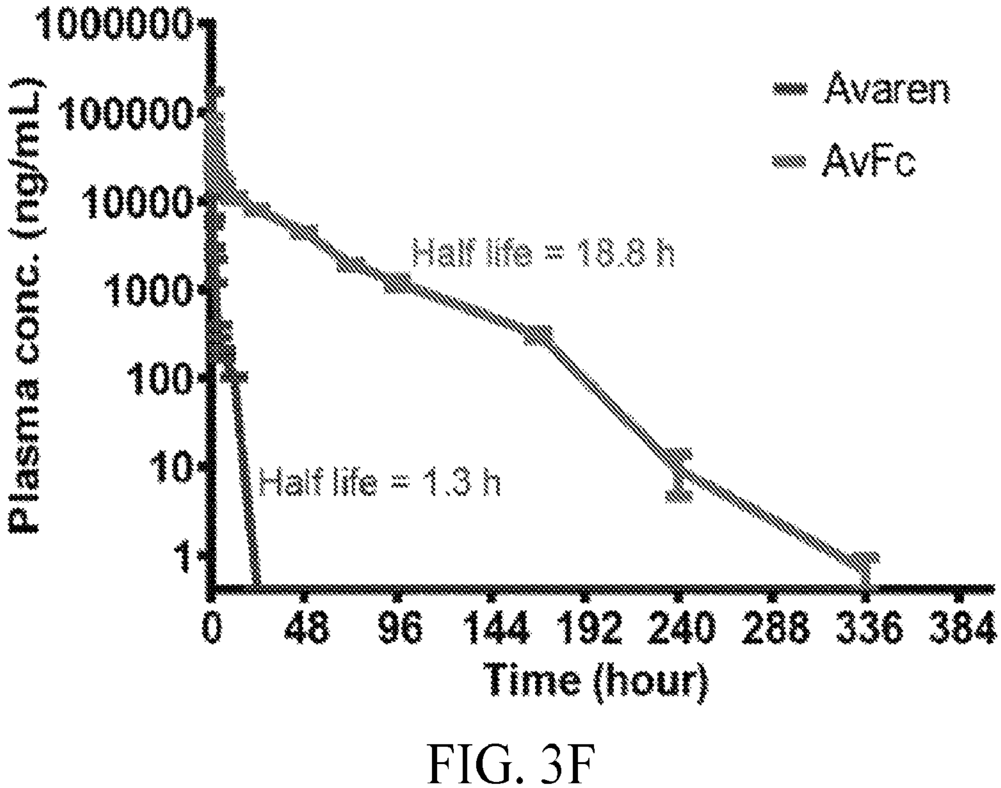
Figure 3G:
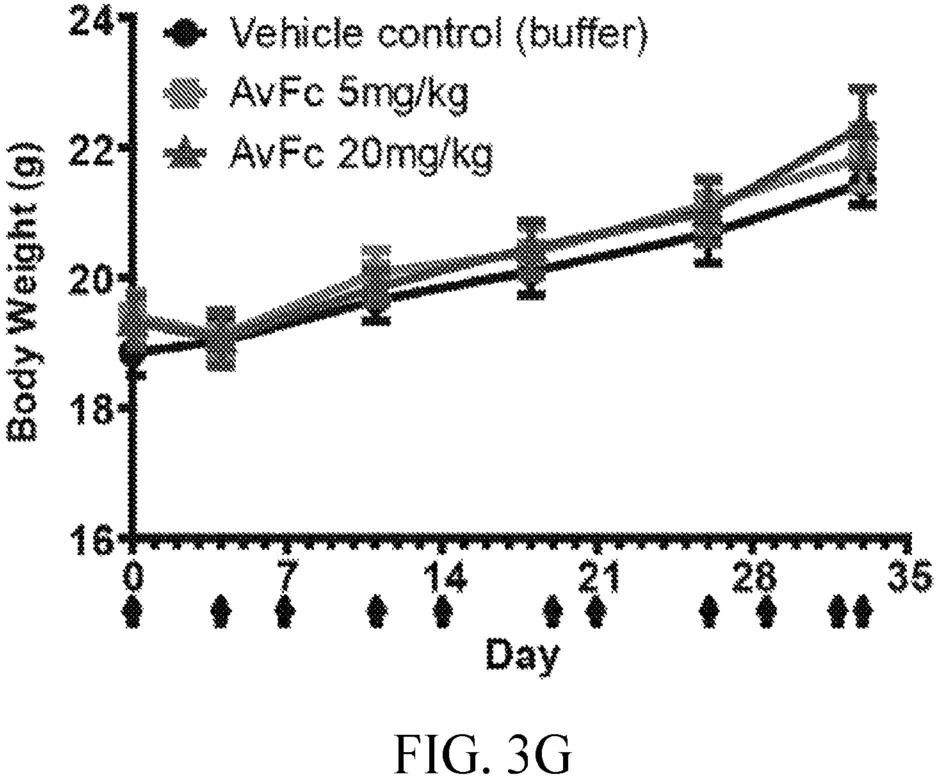
Figure 3H:
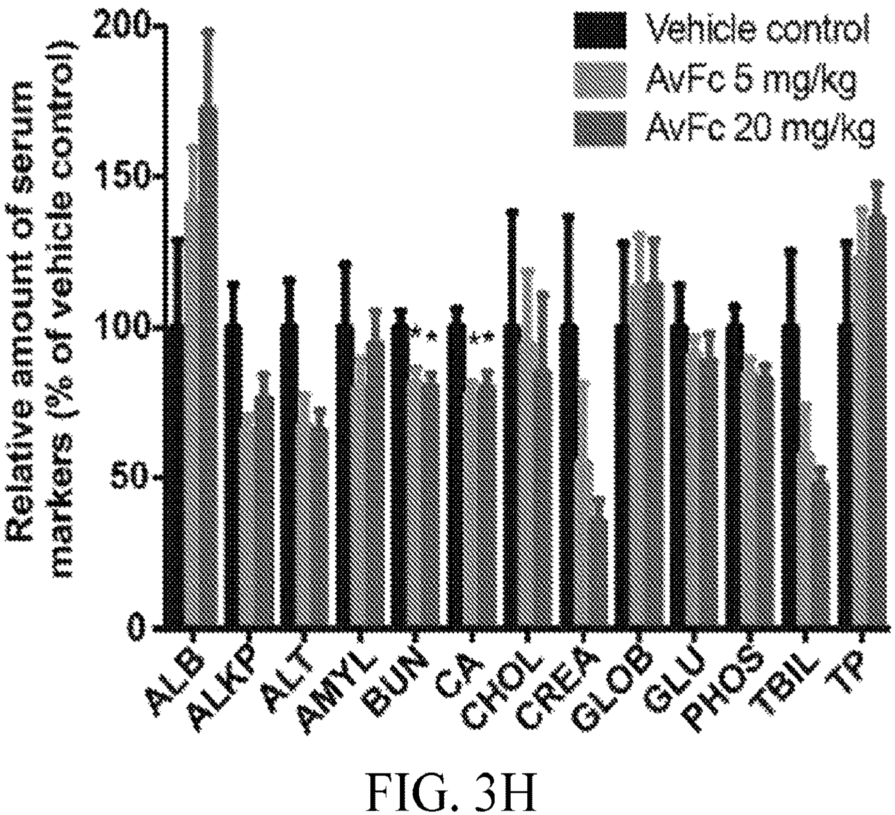
Figure 3I:
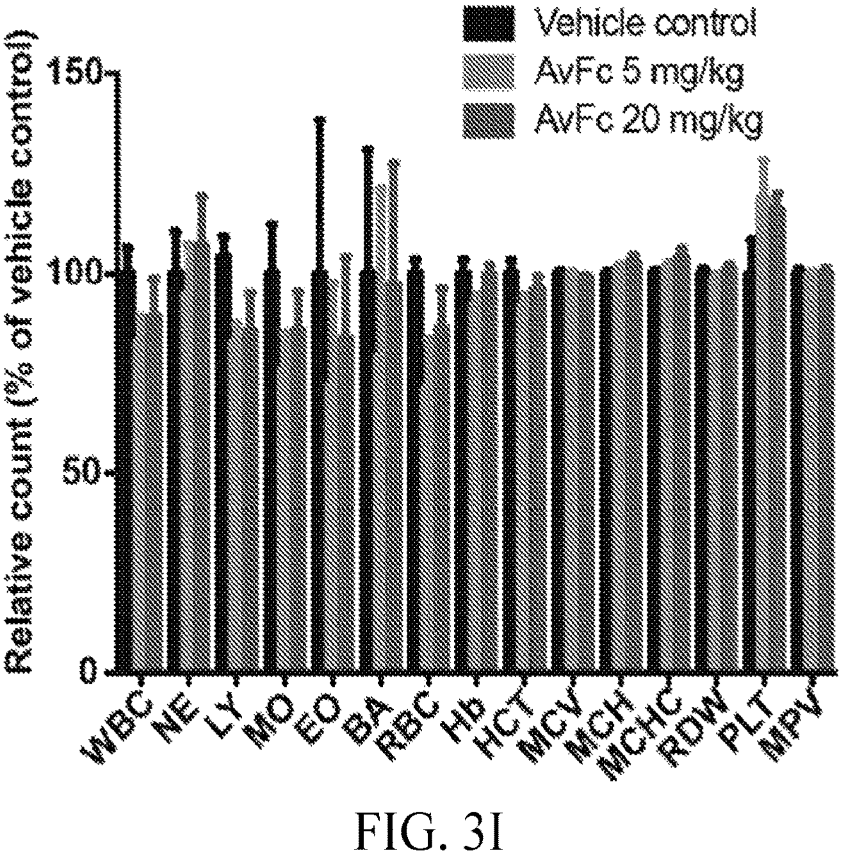
Figure 9E:
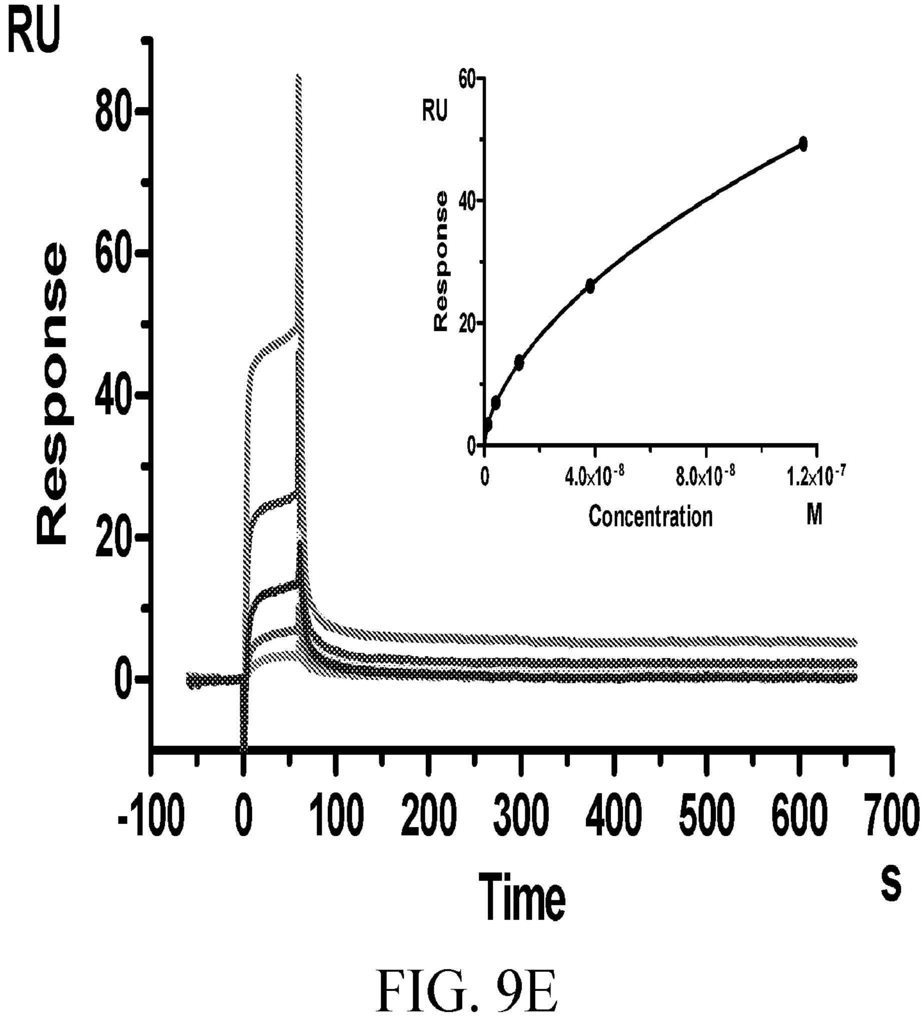
Figure 11E:
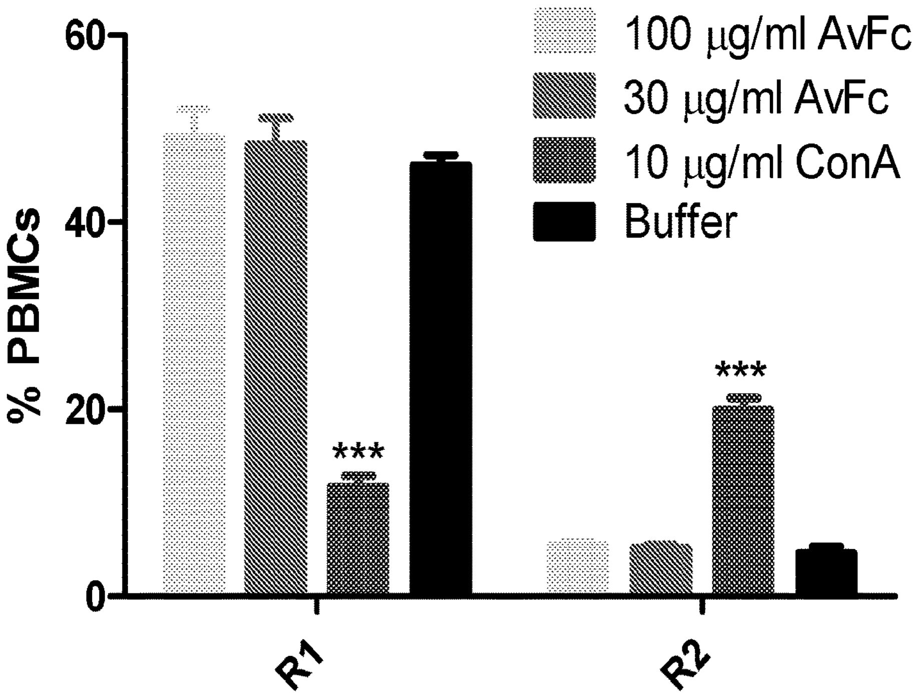
Figure 12A:
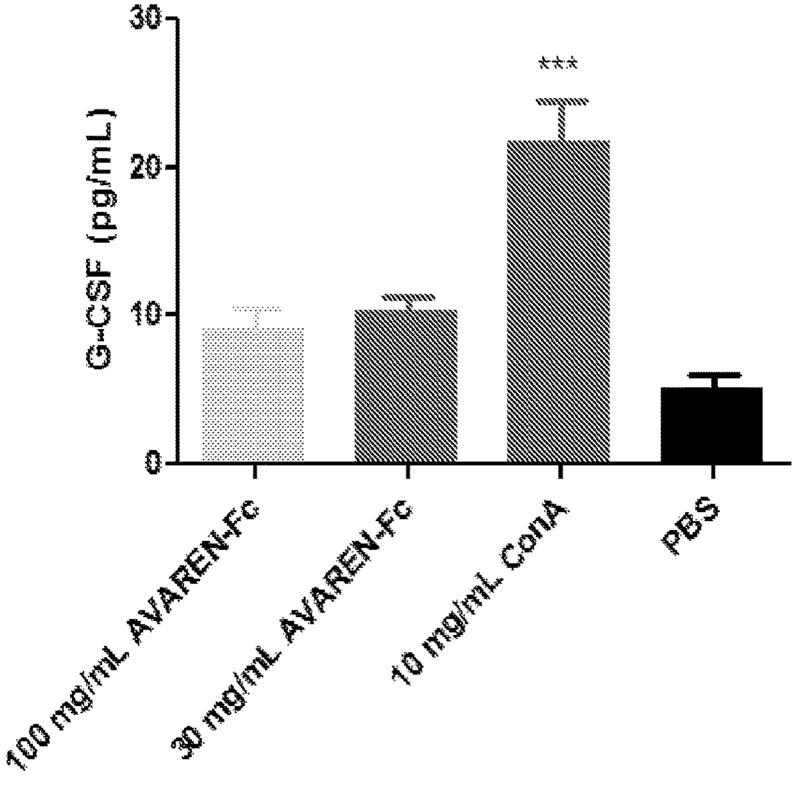
FIGS. 12A-12E are graphs showing the amounts of inflammatory mediators that appeared to be stimulated by AvFc in a multiplex bead array analysis, including graphs showing: G-CSF (FIG. 12A), TNF-α (FIG. 12B), IL-7 (FIG. 12C), and IL-10 (FIG. 12D) levels were increased in some PBMC specimens, when cells were treated with AvFc at 100 μg/ml, but no statistical significance was obtained for their absolute levels when PBMC samples from all donors were considered (*P<0.001; one-way ANOVA with Bonferroni's posttests)
Figure 12B:
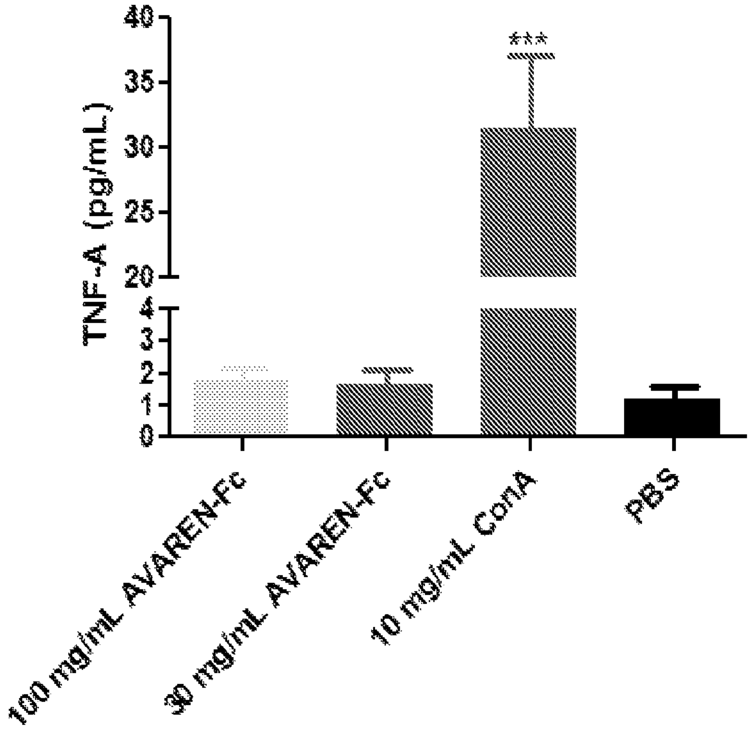
Figure 12C:
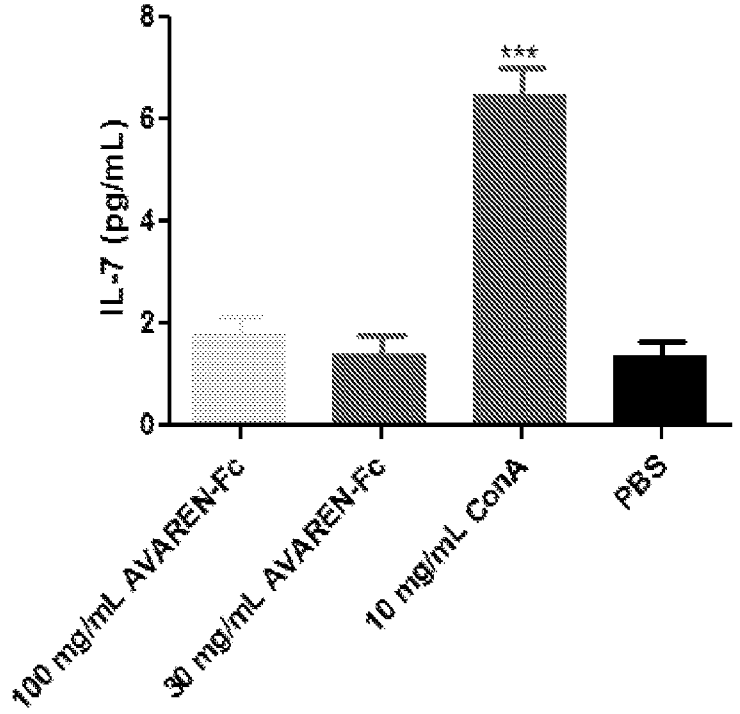
Figure 12D:
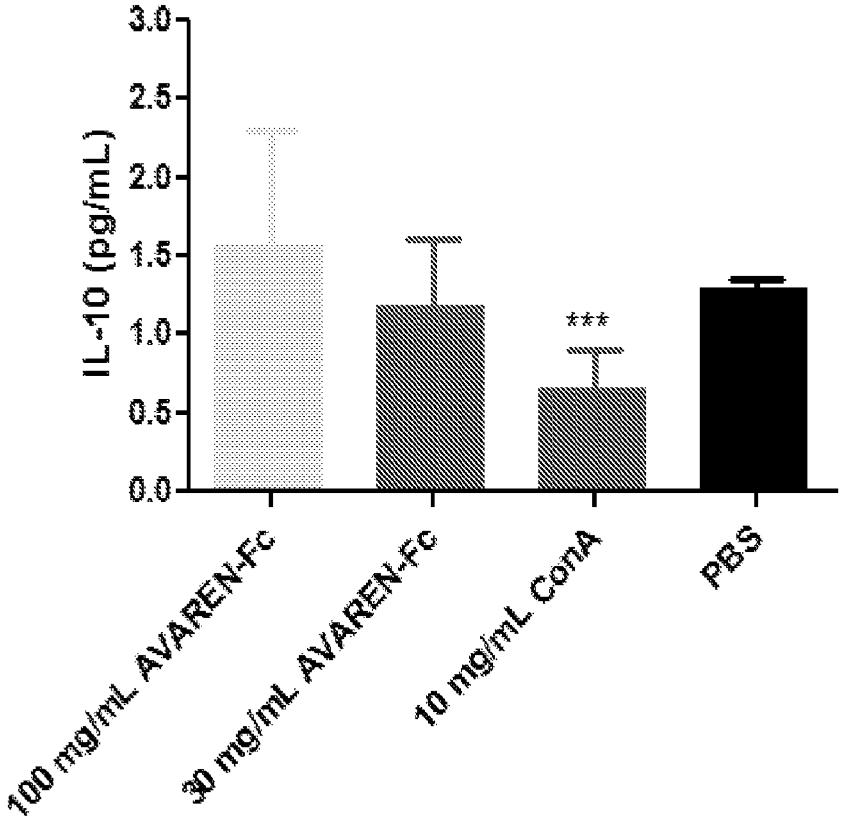
Figure 12E:
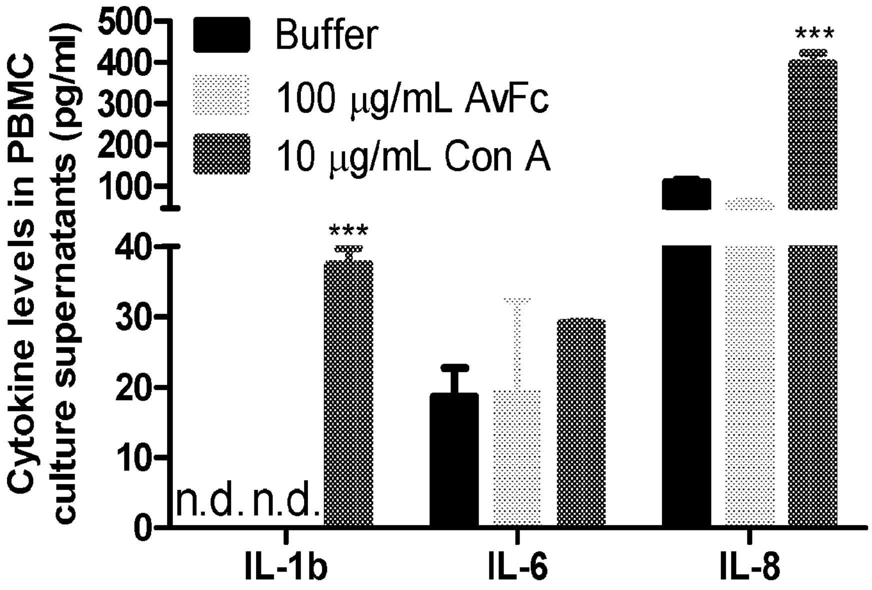
Figure 13A:
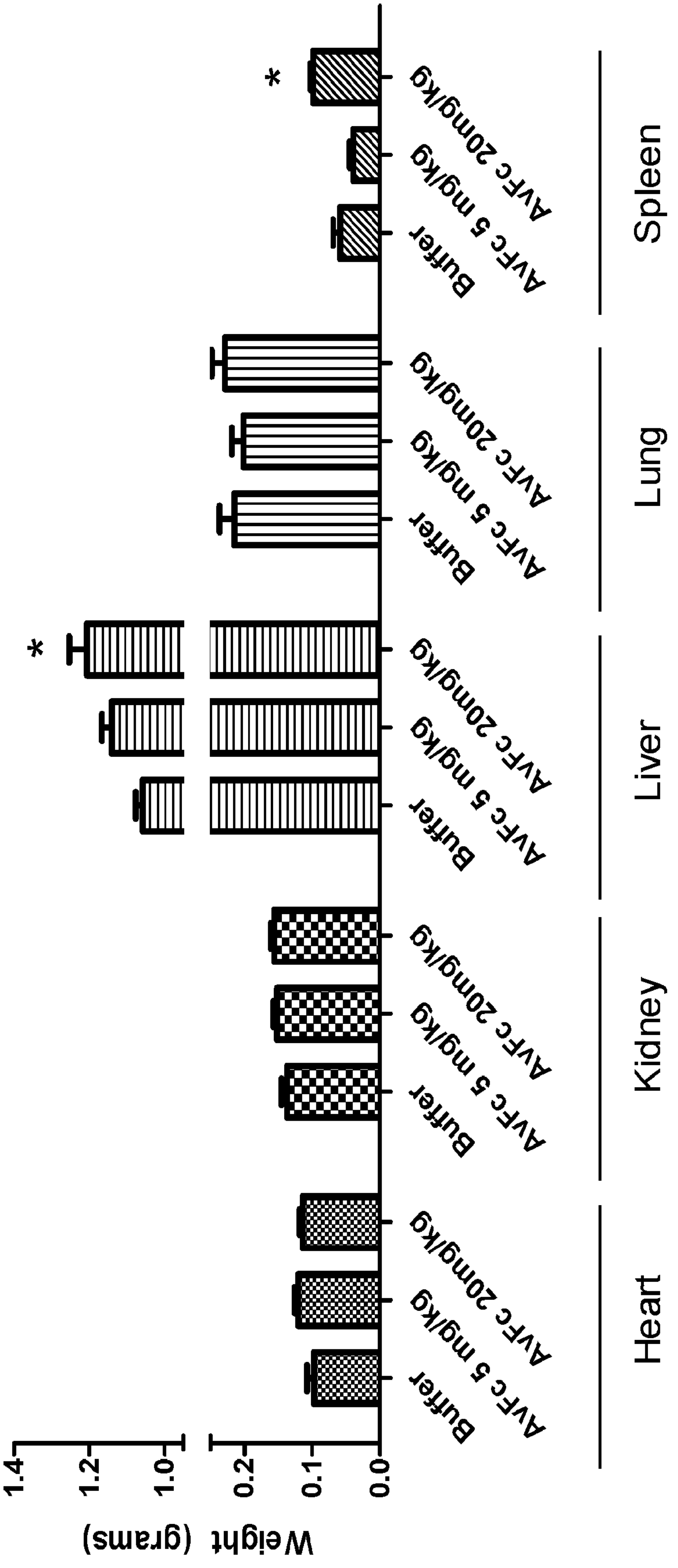
FIGS. 13A-13B are graphs and images showing the effect of AvFc treatment on mouse organ weights, complete blood count and serum chemistry, where, to evaluate effects of a single high dose of AvFc, mice were injected subcutaneously with buffer (n=10), 5 mg/kg AvFc (n=10) or 20 mg/kg AvFc (n=10) twice a week for 5 weeks, where animals were sacrificed on day 35 and blood was taken from the inferior vena cava of each animal for complete blood count and serum chemistry analysis, and where organs were excised, weighed, fixed in 10% buffered formalin for 16 h, and stored in 70% ethanol until paraffin embedding, sectioning, and routine hematoxylin and eosin staining.
Figure 13B:
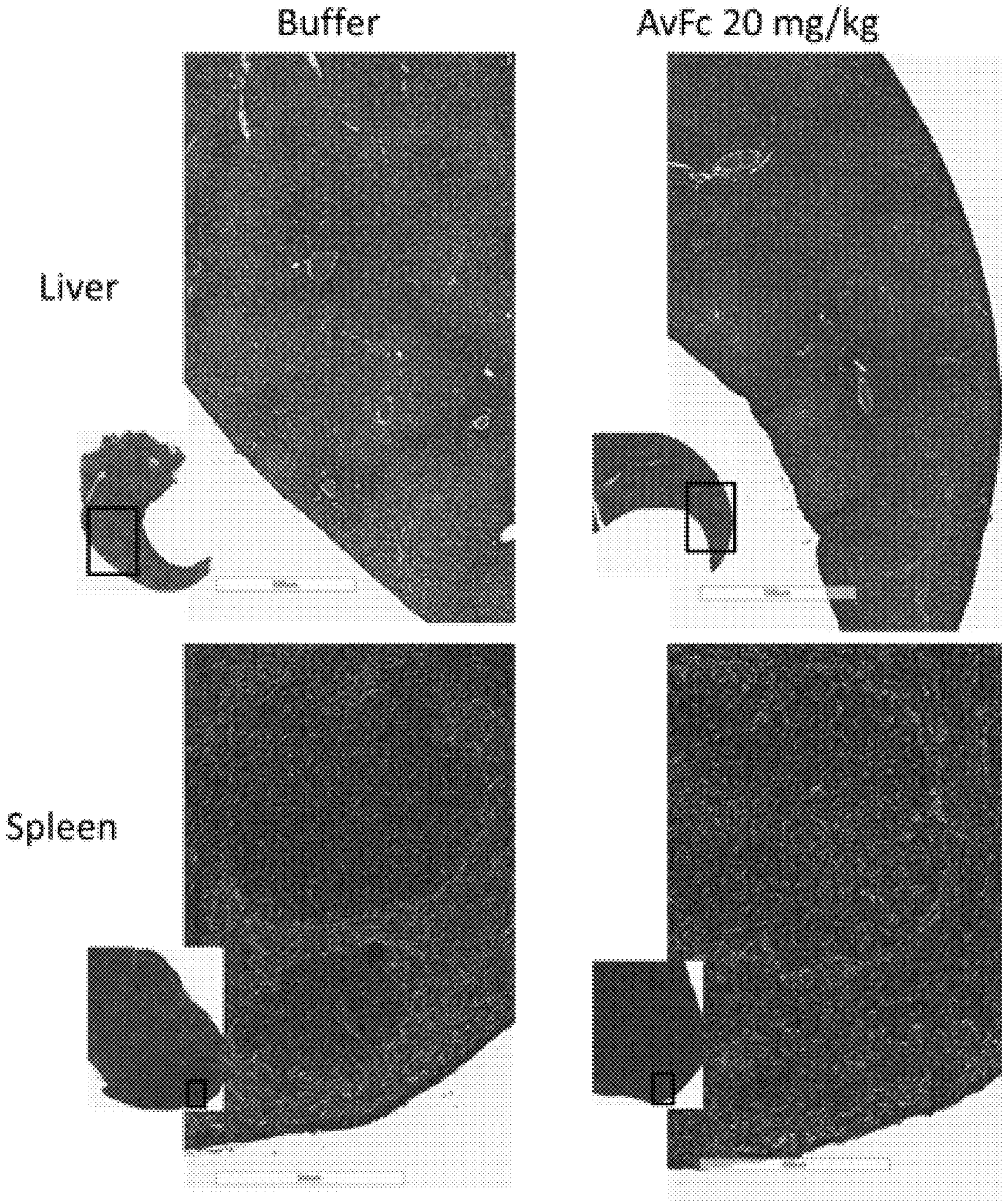

The safety of AvFc was next assessed in in vitro and preclinical animal models. The lectibody showed no cytotoxicity at up to 100 μg/mL in human PBMCs (FIG. 3A), corresponding to 50,000 times the median HIV-neutralization $IC_{50}$ (FIG. 3A). This was in sharp contrast to Concanavalin (Con)A, a well-known mannose-binding lectin, which induced significant cytotoxicity at 10 μg/mL. Similarly, in flow cytometry analysis AvFc showed no induction of the activation markers CD25, CD69 and HLA-DR in CD4 cells (FIGS. 3B-3D) or size and morphological changes in the entire PBMC population (FIG. 11) that were clearly observed with ConA. Cytokine/chemokine release profiles in PMBCs stimulated with AvFc, analyzed using a multiplex bead array, ELISA and quantitative PCR, showed marginal, if any, impacts (FIG. 3E, FIGS. 12A-12E, and Table 1). These results indicated that AvFc had little mitogenicity or immunostimulatory activity that could pose an increased risk in HIV treatment. Next, rats were intravenously administered 4 mg $kg^{-1}$ of AvFc or Avaren. AvFc was detectable in the blood circulation up to 10 days post administration, whereas Avaren was cleared within 24 h (FIG. 3F). The extended bioavailability of AvFc is likely attributed to neonatal Fc receptor affinity (FIG. 9E). Despite its persistence in vivo, AvFc did not appear to induce any adverse effect; to probe its potential toxicity further, the lectibody was administered at 5 or 20 mg kg-1 twice a week over 5 weeks (10 doses total) to mice. All animals survived, and no change was observed in behavior or body weight gain during the experiment (FIG. 3G). An increase of liver and spleen weights was observed for the high dose AvFc-treatment group (P=0.01 and 0.0001, respectively; FIG. 13A). This was likely due to an immune reaction to AvFc, as no distinct pathologies were observed in these tissues (FIG. 13B); both Avaren and human Fc components are xenogeneic to mice. Serum chemistry showed a decrease in blood urea nitrogen and calcium levels for both doses of AvFc (P=0.017 and 0.012, respectively; FIG. 3H and Table 2). Yet, the values were still within or close to the normal physiological ranges. There was no significant difference in any of the complete blood count parameters tested between AvFc-treated and vehicle control-treated mice (FIG. 3I and Table 3). Together, these results showed an overall lack of major toxicity upon AvFc systemic administration.

TABLE 2

Hematological profiles of mice following treatment with AvFc

| Cell Type | Parameter | Unit | Buffer | AvFc 5 mg/kg | AvFc 20 mg/kg |
|---|---|---|---|---|---|
| Leukocyte | WBC | k/μL | 8.6 ± 1.8 | 7.1 ± 1.7 | 7.6 ± 2.6 |
| | NE | k/μL | 2.2 ± 0.7 | 2.1 ± 0.9 | 2.4 ± 0.8 |
| | LY | k/μL | 5.0 ± 0.8 | 4.0 ± 0.7 | 4.1 ± 1.5 |
| | MO | k/μL | 0.9 ± 0.4 | 0.7 ± 0.3 | 0.8 ± 0.3 |
| | EO | k/μL | 0.3 ± 0.4 | 0.2 ± 0.2 | 0.3 ± 0.2 |
| | BA | k/μL | 0.1 ± 0.1 | 0.1 ± 0.1 | 0.1 ± 0.1 |
| Erythrocyte | RBC | M/μL | 11.7 ± 1.3 | 10.7 ± 1.0 | 11.6 ± 1.7 |
| | Hb | g/μL | 17.6 ± 2.0 | 16.3 ± 1.2 | 17.6 ± 1.5 |
| | HCT | % | 62.6 ± 6.8 | 57.3 ± 5.7 | 60.1 ± 6.4 |
| | MCV | fL | 53.7 ± 1.3 | 53.7 ± 1.1 | 53.2 ± 1.2 |
| | MCH | Pg | 15.1 ± 0.3 | 15.3 ± 0.5 | 15.6 ± 0.8 |
| | MCHC | g/dL | 28.1 ± 0.9 | 28.6 ± 1.4 | 29.4 ± 2.0 |
| | RDW | % | 17.1 ± 0.7 | 16.9 ± 0.6 | 17.3 ± 0.7 |
| Thrombocyte | PLT | k/μL | 862.8 ± 231.5 | 1025.0 ± 255.0 | 1001.0 ± 107.0 |
| | MPV | fL | 5.6 ± 0.2 | 5.6 ± 0.1 | 5.7 ± 0.2 |

Data represent mean±S.D. for white blood cells (WBC), neutrophils (NE), lymphocytes (LY), monocytes (MO), eosinophils (EO), basophils (BA), red blood cells (RBC), hemoglobin (Hb), hematocrit (HCT), mean corpuscular volume (MCV), mean cell hemoglobin (MCH), mean cell hemoglobin concentration (MCHC), red cell distribution width (RDW), platelets (PLT), and mean platelet volume (MPV).

TABLE 3

Serum Chemistry values for Mouse following AvFc treatments.

| Parameter | Unit | Buffer | AvFc 5 mg/kg | AvFc 20 mg/kg | Treatment P-value |
|---|---|---|---|---|---|
| ALB | g/dL | 1.3 ± 1.1 | 1.8 ± 0.8 | 2.3 ± 1.1 | 0.14 |
| ALKP | U/L | 230.7 ± 136.2 | 209.5 ± 51.8 | 243.5 ± 85.74 | 0.05 |
| ALT | U/L | 339.8 ± 315.7 | 160.9 ± 78.1 | 156.8 ± 51.1 | 0.06 |
| AMYL | U/L | 1604.0 ± 998.9 | 1271.0 ± 522.6 | 1517.0 ± 552.3 | 0.57 |
| BUN | mg/dL | 32.0 ± 5.3 | 26.0 ± 5.1* | 25.6 ± 4.6* | 0.02 |
| Ca | mg/dL | 18.0 ± 3.3 | 13.87 ± 2.5* | 14.3 ± 3.1* | 0.01 |
| CHOL | mg/dL | 51.3 ± 58.4 | 48.3 ± 39.6 | 43.7 ± 41.6 | 0.93 |
| CREA | mg/dL | 1.4 ± 1.5 | 0.8 ± 1.2 | 0.5 ± 0.3 | 0.21 |
| GLOB | g/dL | 2.2 ± 1.8 | 2.5 ± 1.2 | 2.5 ± 1.1 | 0.87 |
| GLU | mg/dL | 299.0 ± 123.3 | 270.6 ± 58.52 | 265.3 ± 88.0 | 0.70 |
| PHOS | mg/dL | 14.6 ± 3.1 | 12.3 ± 2.6 | 12.0 ± 2.4 | 0.09 |
| TBIL | mg/dL | 0.8 ± 0.6 | 0.5 ± 0.4 | 0.4 ± 0.1 | 0.09 |
| TP | g/Dl | 3.6 ± 3.0 | 4.4 ± 1.8 | 4.8 ± 1.3 | 0.42 |

Treatment p values were obtained by one-way ANOVA with bonferonni's posttests

Figure 14A:
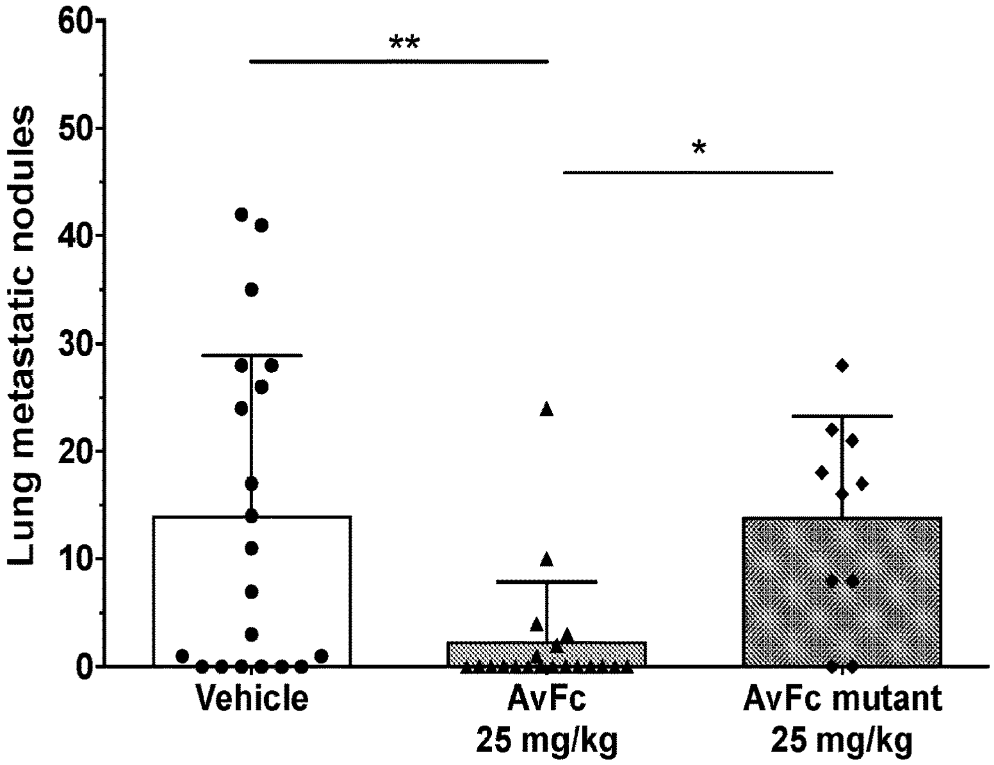
FIGS. 14A-14B are graphs and images showing AvFc's effects in a B16F10 melanoma lung metastasis model.
Figure 14B:
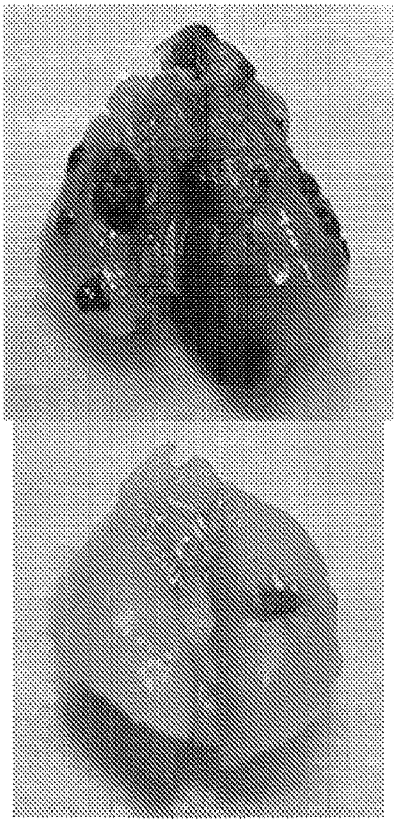

To determine if AvFc has any in vivo anti-cancer activity, C567bl/6 mice were intravenously injected with $2.5\times10^5$ B16F10 melanoma cells. Concurrently, mice were dosed with 200 μL of vehicle (30 mM histidine, 100 mM NaCl, 100 mM sucrose; n=20), 25 mg/kg AvFc (n=20) or 25 mg/kg AvFc mutant ([Y32A, Y70A, Y108A]-AvFc, which lacks sugar-binding activity; n=10) on days 0, 2, 4, 6, 8, and 10. On day 21 post cancer cell injection mice were euthanized, their lungs surgically removed, and the number of metastatic loci counted. The data shown in FIG. 14A are reported as mean tumor count per lung±standard deviation. Each dot represents the number of lung metastatic nodules of each mouse. Statistical difference between groups were analyzed by Kruskal-Wallis and Dunn's multiple comparisons tests (*, P<0.05, 0.01). Representative images of lung with many (top) and few (bottom) metastatic nodules are shown in FIG. 14**B.

In summary, the foregoing data demonstrated the ability of AvFc to target a carbohydrate biomarker of HIV and tumors. The studies further highlighted the utility of a plant viral expression system for the engineering of novel recombinant proteins. Further engineering to reduce immunogenicity, such as T cell epitope depletion, can accelerate AvFc's drug potential. As the plant expression system may enable economical large-scale protein production, high producibility in plants represents an additional advantage of AvFc. Hence, the plant-made lectibody provided a new tool for the investigation and treatment of HIV infection and cancer.

All publications, patents, and patent applications mentioned in this specification are herein incorporated by reference to the same extent as if each individual publication, patent, or patent application was specifically and individually indicated to be incorporated by reference, including the references set forth in the following list:

REFERENCES

1. Balzarini, J. Targeting the glycans of glycoproteins: a novel paradigm for antiviral therapy. Nat Rev Microbiol 5, 583-597 (2007).
2. Liu, X. et al. Cell surface-specific N-glycan profiling in breast cancer. PLoS One 8, e72704 (2013).
3. Newsom-Davis, T. E. et al. Enhanced immune recognition of cryptic glycan markers in human tumors. Cancer Res 69, 2018-2025 (2009).
4. de Leoz, M. L. et al. High-mannose glycans are elevated during breast cancer progression. Mol Cell Proteomics (2010).
5. Holst, S. et al. N-glycosylation Profiling of Colorectal Cancer Cell Lines Reveals Association of Fucosylation with Differentiation and Caudal Type Homebox 1 (CDX1)/Villin mRNA Expression. Mol Cell Proteomics 15, 124-140 (2016).
6. Everest-Dess, A. V. et al. N-Glycan MALDI Imaging Mass Spectrometry on Formalin-Fixed Paraffin-Embedded Tissue Enables the Delineation of Ovarian Cancer Tissues. Mol Cell Proteomics (2016).
7. Molinari, M. N-glycan structure dictates extension of protein folding or onset of disposal. Nature chemical biology 3, 313-320 (2007).
8. Sharon, N. Lectins: carbohydrate-specific reagents and biological recognition molecules. J Biol Chem 282, 2753-2764 (2007).

9. Hivrale, A. & Ingale, A. Plant as a plenteous reserve of lectin. Plant signaling & behavior 8 (2013).
10. Oliveira, C., Teixeira, J. A. & Domingues, L. Recombinant lectins: an array of tailor-made glycan-interaction biosynthetic tools. Critical reviews in biotechnology 33, 66-80 (2013).
11. Lam, S. $K_D$ & Ng, T. B. Lectins: production and practical applications. Applied microbiology and biotechnology 89, 45-55 (2011).
12. Tanaka, H. et al. Mechanism by which the lectin actinohivin blocks HIV infection of target cells. Proc Natl Acad Sci USA 106, 15633-15638 (2009).
13. Zhang, F. et al. The Characteristic Structure of Anti-HIV Actinohivin in Complex with Three HMTG D1 Chains of HIV-gp120. Chembiochem: a European journal of chemical biology (2014).
14. Matoba, N. et al. HIV-1 neutralization profile and plant-based recombinant expression of actinohivin, an Env glycan-specific lectin devoid of T-cell mitogenic activity. PLoS One 5, e11143 (2010).
15. Marillonnet, S. et al. In planta engineering of viral RNA replicons: efficient assembly by recombination of DNA modules delivered by *Agrobacterium*. Proc Natl Acad Sci USA 101, 6852-6857 (2004).
16. Arnold, K., Bordoli, L., Kopp, J. & Schwede, T. The SWISS-MODEL workspace: a web-based environment for protein structure homology modelling. Bioinformatics 22, 195-201 (2006).
17. Czajkowsky, D. M., Hu, J., Shao, Z. & Pleass, R. J. Fc-fusion proteins: new developments and future perspectives. EMBO molecular medicine 4, 1015-1028 (2012).
18. Forthal, D. N. et al. Rhesus macaque polyclonal and monoclonal antibodies inhibit simian immunodeficiency virus in the presence of human or autologous rhesus effector cells. Journal of virology 80, 9217-9225 (2006).
19. Li, W. W., Yu, J. Y., Xu, H. L. & Bao, J. K. Concanavalin A: a potential anti-neoplastic agent targeting apoptosis, autophagy and anti-angiogenesis for cancer therapeutics. Biochemical and biophysical research communications 414, 282-286 (2011).
20. Benoist, H. et al. Two structurally identical mannose-specific jacalin-related lectins display different effects on human T lymphocyte activation and cell death. Journal of leukocyte biology 86, 103-114 (2009).
21. Hamorsky, K. T. et al. Efficient single tobamoviral vector-based bioproduction of broadly neutralizing anti-HIV-1 monoclonal antibody VRC01 in *Nicotiana benthamiana* plants and utility of VRC01 in combination microbicides. Antimicrobial agents and chemotherapy 57, 2076-2086 (2013).
22. Gleba, Y., Klimyuk, V. & Marillonnet, S. Magnifection—α new platform for expressing recombinant vaccines in plants. Vaccine 23, 2042-2048 (2005).
23. Kouokam, J. C. et al. Investigation of griffithsin's interactions with human cells confirms its outstanding safety and efficacy profile as a microbicide candidate. PLoS One 6, e22635 (2011).

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A polypeptide, comprising an actinohivin variant polypeptide of SEQ ID NO:7, SEQ ID NO:10 or SEQ ID NO:11.

2. The polypeptide of claim 1, further comprising an antibody fragment operably connected to the actinohivin variant polypeptide.

3. The polypeptide of claim 2, wherein the antibody fragment comprises a fragment crystallizable (Fc) region of immunoglobulin (Ig) G.

4. A pharmaceutical composition, comprising the polypeptide of claim 1 and a pharmaceutically-acceptable vehicle, carrier, or excipient.

5. An isolated nucleic acid, comprising a nucleic acid sequence encoding the polypeptide of claim 1.

6. The isolated nucleic acid of claim 5, wherein the nucleic acid sequence further encodes an antibody fragment operably connected to the actinohivin variant polypeptide.

7. The isolated nucleic acid of claim 6, wherein the antibody fragment comprises a fragment crystallizable (Fc) region of immunoglobulin (Ig) G.

8. An expression vector, comprising a nucleic acid sequence encoding an actinohivin variant polypeptide of SEQ ID NO:7, SEQ ID NO:10 or SEQ ID NO:11, operably linked to an expression cassette.

9. A plant cell transfected with the vector of claim 8, or a progeny of the plant cell, wherein the cell or the progeny thereof expresses the polypeptide.

10. A method of treating a viral infection, comprising administering the actinohivin variant polypeptide of claim 1 to a subject in need thereof.

11. A method of treating a cancer, comprising administering a polypeptide to a subject in need thereof, wherein the polypeptide comprises a fragment crystallizable (Fc) region of immunoglobulin (Ig) G operably connected to an actinohivin variant polypeptide of SEQ ID NO: 9, and wherein the cancer is selected from lung cancer, breast cancer, colon cancer, and melanoma.

12. The method of claim 11, wherein the actinohivin variant polypeptide and the antibody fragment comprise the sequence of SEQ ID NO: 16.

13. The method of claim 11, wherein the cancer is characterized by one or more cancer cells having high-mannose-type glycans on a cell membrane of the one or more cancer cells.

14. The method of claim 11, wherein the cancer is lung cancer.

15. The method of claim 11, wherein the cancer is breast cancer.

16. The method of claim 11, wherein the cancer is colon cancer.

17. The method of claim 11, wherein the cancer is melanoma.

* * * * *

SEQUENCE LISTING

```
<160> NUMBER OF SEQ ID NOS: 16

<210> SEQ ID NO 1
<211> LENGTH: 114
<212> TYPE: PRT
<213> ORGANISM: actinomycete strain K97-0003

<400> SEQUENCE: 1

Ala Ser Val Thr Ile Arg Asn Ala Gln Thr Gly Arg Leu Leu Asp Ser
1               5                   10                  15

Asn Tyr Asn Gly Asn Val Tyr Thr Leu Pro Ala Asn Gly Gly Asn Tyr
            20                  25                  30

Gln Arg Trp Thr Gly Pro Gly Asp Gly Thr Val Arg Asn Ala Gln Thr
        35                  40                  45

Gly Arg Cys Leu Asp Ser Asn Tyr Asp Gly Ala Val Tyr Thr Leu Pro
    50                  55                  60

Cys Asn Gly Gly Ser Tyr Gln Lys Trp Leu Phe Tyr Ser Asn Gly Tyr
65                  70                  75                  80

Ile Gln Asn Val Glu Thr Gly Arg Val Leu Asp Ser Asn Tyr Asn Gly
                85                  90                  95

Asn Val Tyr Thr Leu Pro Ala Asn Gly Gly Asn Tyr Gln Lys Trp Tyr
            100                 105                 110

Thr Gly


<210> SEQ ID NO 2
<211> LENGTH: 113
<212> TYPE: PRT
<213> ORGANISM: Artificial Sequence
<220> FEATURE:
```

<223> OTHER INFORMATION: Actinohivin Variant Polypeptide

<400> SEQUENCE: 2

```
Ala Ser Gly Thr Ile Arg Asn Ala Glu Thr Gly Arg Leu Leu Asp Ser
1               5                   10                  15

Asn Tyr Asp Gly Ala Val Tyr Thr Leu Pro Ala Asn Gly Gly Ser Tyr
            20                  25                  30

Gln Arg Trp Thr Gly Pro Gly Asp Gly Thr Val Arg Asn Ala Glu Thr
        35                  40                  45

Gly Arg Leu Leu Asp Ser Asn Tyr Asp Gly Ala Val Tyr Thr Leu Pro
    50                  55                  60

Ala Asn Gly Gly Ser Tyr Gln Lys Trp Thr Gly Pro Gly Asp Gly Thr
65                  70                  75                  80

Ile Gln Asn Ala Glu Thr Gly Arg Leu Leu Asp Ser Asn Tyr Asp Gly
                85                  90                  95

Ala Val Tyr Thr Leu Pro Ala Asn Gly Gly Ser Tyr Gln Lys Trp Thr
            100                 105                 110

Gly
```

<210> SEQ ID NO 3
<211> LENGTH: 113
<212> TYPE: PRT
<213> ORGANISM: Artificial Sequence
<220> FEATURE:
<223> OTHER INFORMATION: Actinohivin Variant Polypeptide

<400> SEQUENCE: 3

```
Ala Ser Gly Thr Ile Arg Asn Ala Glu Thr Gly Arg Cys Leu Asp Ser
1               5                   10                  15

Asn Tyr Asp Gly Ala Val Tyr Thr Leu Pro Cys Asn Gly Gly Ser Tyr
            20                  25                  30

Gln Arg Trp Thr Gly Pro Gly Asp Gly Thr Val Arg Asn Ala Glu Thr
        35                  40                  45

Gly Arg Cys Leu Asp Ser Asn Tyr Asp Gly Ala Val Tyr Thr Leu Pro
    50                  55                  60

Cys Asn Gly Gly Ser Tyr Gln Lys Trp Thr Gly Pro Gly Asp Gly Thr
65                  70                  75                  80

Ile Gln Asn Ala Glu Thr Gly Arg Cys Leu Asp Ser Asn Tyr Asp Gly
                85                  90                  95

Ala Val Tyr Thr Leu Pro Cys Asn Gly Gly Ser Tyr Gln Lys Trp Thr
            100                 105                 110

Gly
```

<210> SEQ ID NO 4
<211> LENGTH: 114
<212> TYPE: PRT
<213> ORGANISM: Artificial Sequence
<220> FEATURE:
<223> OTHER INFORMATION: Actinohivin Variant Polypeptide

<400> SEQUENCE: 4

```
Ala Ser Val Thr Ile Arg Asn Ala Glu Thr Gly Arg Leu Leu Asp Ser
1               5                   10                  15

Asn Tyr Asn Gly Asn Val Tyr Thr Leu Pro Ala Asn Gly Gly Asn Tyr
            20                  25                  30

Gln Arg Trp Thr Gly Pro Gly Asp Gly Thr Val Arg Asn Ala Glu Thr
        35                  40                  45
```

-continued

```
Gly Arg Cys Leu Asp Ser Asn Tyr Asp Gly Ala Val Tyr Thr Leu Pro
    50                  55                  60

Cys Asn Gly Gly Ser Tyr Gln Lys Trp Leu Phe Tyr Ser Asn Gly Tyr
65                  70                  75                  80

Ile Gln Asn Val Glu Thr Gly Arg Val Leu Asp Ser Asn Tyr Asn Gly
                85                  90                  95

Asn Val Tyr Thr Leu Pro Ala Asn Gly Gly Asn Tyr Gln Lys Trp Tyr
            100                 105                 110

Thr Gly


<210> SEQ ID NO 5
<211> LENGTH: 114
<212> TYPE: PRT
<213> ORGANISM: Artificial Sequence
<220> FEATURE:
<223> OTHER INFORMATION: Actinohivin Variant Polypeptide

<400> SEQUENCE: 5

Ala Ser Val Thr Ile Arg Asn Ala Glu Thr Gly Arg Cys Leu Asp Ser
1               5                   10                  15

Asn Tyr Asn Gly Asn Val Tyr Thr Leu Pro Cys Asn Gly Gly Asn Tyr
            20                  25                  30

Gln Arg Trp Thr Gly Pro Gly Asp Gly Thr Val Arg Asn Ala Glu Thr
        35                  40                  45

Gly Arg Cys Leu Asp Ser Asn Tyr Asp Gly Ala Val Tyr Thr Leu Pro
    50                  55                  60

Cys Asn Gly Gly Ser Tyr Gln Lys Trp Leu Phe Tyr Ser Asn Gly Tyr
65                  70                  75                  80

Ile Gln Asn Val Glu Thr Gly Arg Cys Leu Asp Ser Asn Tyr Asn Gly
                85                  90                  95

Asn Val Tyr Thr Leu Pro Cys Asn Gly Gly Asn Tyr Gln Lys Trp Tyr
            100                 105                 110

Thr Gly


<210> SEQ ID NO 6
<211> LENGTH: 113
<212> TYPE: PRT
<213> ORGANISM: Artificial Sequence
<220> FEATURE:
<223> OTHER INFORMATION: Actinohivin Variant Polypeptide

<400> SEQUENCE: 6

Ala Ser Gly Thr Ile Arg Asn Ala Glu Thr Gly Arg Leu Leu Asp Ser
1               5                   10                  15

Asn Tyr Asn Gly Asn Val Tyr Thr Leu Pro Ala Asn Gly Gly Asn Tyr
            20                  25                  30

Gln Arg Trp Thr Gly Pro Gly Asp Gly Thr Val Arg Asn Ala Glu Thr
        35                  40                  45

Gly Arg Cys Leu Asp Ser Asn Tyr Asp Gly Ala Val Tyr Thr Leu Pro
    50                  55                  60

Cys Asn Gly Gly Ser Tyr Gln Lys Trp Thr Gly Pro Gly Asp Gly Thr
65                  70                  75                  80

Ile Gln Asn Ala Glu Thr Gly Arg Val Leu Asp Ser Asn Tyr Asn Gly
                85                  90                  95

Asn Val Tyr Thr Leu Pro Ala Asn Gly Gly Asn Tyr Gln Lys Trp Thr
            100                 105                 110

Gly
```

<210> SEQ ID NO 7
<211> LENGTH: 113
<212> TYPE: PRT
<213> ORGANISM: Artificial Sequence
<220> FEATURE:
<223> OTHER INFORMATION: Actinohivin Variant Polypeptide

<400> SEQUENCE: 7

Ala Ser Gly Thr Ile Arg Asn Ala Glu Thr Gly Arg Cys Leu Asp Ser
1 5 10 15

Asn Tyr Asp Gly Asn Val Tyr Thr Leu Pro Cys Asn Gly Gly Ser Tyr
20 25 30

Gln Arg Trp Thr Gly Pro Gly Asp Gly Thr Val Arg Asn Ala Glu Thr
35 40 45

Gly Arg Cys Leu Asp Ser Asn Tyr Asp Gly Asn Val Tyr Thr Leu Pro
50 55 60

Cys Asn Gly Gly Ser Tyr Gln Lys Trp Thr Gly Pro Gly Asp Gly Thr
65 70 75 80

Ile Gln Asn Ala Glu Thr Gly Arg Cys Leu Asp Ser Asn Tyr Asp Gly
85 90 95

Asn Val Tyr Thr Leu Pro Cys Asn Gly Gly Ser Tyr Gln Lys Trp Thr
100 105 110

Gly

<210> SEQ ID NO 8
<211> LENGTH: 113
<212> TYPE: PRT
<213> ORGANISM: Artificial Sequence
<220> FEATURE:
<223> OTHER INFORMATION: Actinohivin Variant Polypeptide

<400> SEQUENCE: 8

Ala Ser Gly Thr Ile Arg Asn Ala Gln Thr Gly Arg Cys Leu Asp Ser
1 5 10 15

Asn Tyr Asn Gly Asn Val Tyr Thr Leu Pro Cys Asn Gly Gly Asn Tyr
20 25 30

Gln Arg Trp Thr Gly Pro Gly Asp Gly Thr Val Arg Asn Ala Gln Thr
35 40 45

Gly Arg Cys Leu Asp Ser Asn Tyr Asp Gly Ala Val Tyr Thr Leu Pro
50 55 60

Cys Asn Gly Gly Ser Tyr Gln Lys Trp Thr Gly Pro Gly Asp Gly Thr
65 70 75 80

Ile Gln Asn Ala Glu Thr Gly Arg Cys Leu Asp Ser Asn Tyr Asn Gly
85 90 95

Asn Val Tyr Thr Leu Pro Cys Asn Gly Gly Asn Tyr Gln Lys Trp Thr
100 105 110

Gly

<210> SEQ ID NO 9
<211> LENGTH: 113
<212> TYPE: PRT
<213> ORGANISM: Artificial Sequence
<220> FEATURE:
<223> OTHER INFORMATION: Actinohivin Variant Polypeptide

<400> SEQUENCE: 9

Ala Ser Gly Thr Ile Arg Asn Ala Glu Thr Gly Arg Cys Leu Asp Ser
1 5 10 15

```
Asn Tyr Asn Gly Asn Val Tyr Thr Leu Pro Cys Asn Gly Gly Asn Tyr
            20                  25                  30

Gln Arg Trp Thr Gly Pro Gly Asp Gly Thr Val Arg Asn Ala Glu Thr
        35                  40                  45

Gly Arg Cys Leu Asp Ser Asn Tyr Asp Gly Ala Val Tyr Thr Leu Pro
    50                  55                  60

Cys Asn Gly Gly Ser Tyr Gln Lys Trp Thr Gly Pro Gly Asp Gly Thr
65                  70                  75                  80

Ile Gln Asn Ala Glu Thr Gly Arg Cys Leu Asp Ser Asn Tyr Asn Gly
                85                  90                  95

Asn Val Tyr Thr Leu Pro Cys Asn Gly Gly Asn Tyr Gln Lys Trp Thr
            100                 105                 110

Gly


<210> SEQ ID NO 10
<211> LENGTH: 113
<212> TYPE: PRT
<213> ORGANISM: Artificial Sequence
<220> FEATURE:
<223> OTHER INFORMATION: Actinohivin Variant Polypeptide

<400> SEQUENCE: 10

Ala Ser Gly Thr Ile Arg Asn Ala Gln Thr Gly Arg Cys Leu Asp Ser
1               5                   10                  15

Asn Tyr Asn Gly Asn Val Tyr Thr Leu Pro Cys Asn Gly Gly Asn Tyr
            20                  25                  30

Gln Arg Trp Thr Gly Pro Gly Asp Gly Thr Val Arg Asn Ala Glu Thr
        35                  40                  45

Gly Arg Cys Leu Asp Ser Asn Tyr Asp Gly Ala Val Tyr Thr Leu Pro
    50                  55                  60

Cys Asn Gly Gly Ser Tyr Gln Lys Trp Thr Gly Pro Gly Asp Gly Thr
65                  70                  75                  80

Ile Gln Asn Ala Glu Thr Gly Arg Cys Leu Asp Ser Asn Tyr Asn Gly
                85                  90                  95

Asn Val Tyr Thr Leu Pro Cys Asn Gly Gly Asn Tyr Gln Lys Trp Thr
            100                 105                 110

Gly


<210> SEQ ID NO 11
<211> LENGTH: 113
<212> TYPE: PRT
<213> ORGANISM: Artificial Sequence
<220> FEATURE:
<223> OTHER INFORMATION: Actinohivin Variant Polypeptide

<400> SEQUENCE: 11

Ala Ser Gly Thr Ile Arg Asn Ala Glu Thr Gly Arg Cys Leu Asp Ser
1               5                   10                  15

Asn Tyr Asn Gly Asn Val Tyr Thr Leu Pro Cys Asn Gly Gly Asn Tyr
            20                  25                  30

Gln Arg Trp Thr Gly Pro Gly Asp Gly Thr Val Arg Asn Ala Gln Thr
        35                  40                  45

Gly Arg Cys Leu Asp Ser Asn Tyr Asp Gly Ala Val Tyr Thr Leu Pro
    50                  55                  60

Cys Asn Gly Gly Ser Tyr Gln Lys Trp Thr Gly Pro Gly Asp Gly Thr
65                  70                  75                  80
```

```
Ile Gln Asn Ala Glu Thr Gly Arg Cys Leu Asp Ser Asn Tyr Asn Gly
                85                  90                  95

Asn Val Tyr Thr Leu Pro Cys Asn Gly Gly Asn Tyr Gln Lys Trp Thr
            100                 105                 110

Gly


<210> SEQ ID NO 12
<211> LENGTH: 113
<212> TYPE: PRT
<213> ORGANISM: Artificial Sequence
<220> FEATURE:
<223> OTHER INFORMATION: Actinohivin Variant Polypeptide

<400> SEQUENCE: 12

Ala Ser Gly Thr Ile Arg Asn Ala Gln Thr Gly Arg Leu Leu Asp Ser
1               5                   10                  15

Asn Tyr Asn Gly Asn Val Tyr Thr Leu Pro Ala Asn Gly Gly Asn Tyr
            20                  25                  30

Gln Arg Trp Thr Gly Pro Gly Asp Gly Thr Val Arg Asn Ala Gln Thr
        35                  40                  45

Gly Arg Leu Leu Asp Ser Asn Tyr Asn Gly Asn Val Tyr Thr Leu Pro
    50                  55                  60

Ala Asn Gly Gly Asn Tyr Gln Lys Trp Thr Gly Pro Gly Asp Gly Thr
65                  70                  75                  80

Ile Gln Asn Ala Gln Thr Gly Arg Val Leu Asp Ser Asn Tyr Asn Gly
                85                  90                  95

Asn Val Tyr Thr Leu Pro Ala Asn Gly Gly Asn Tyr Gln Lys Trp Thr
            100                 105                 110

Gly


<210> SEQ ID NO 13
<211> LENGTH: 113
<212> TYPE: PRT
<213> ORGANISM: Artificial Sequence
<220> FEATURE:
<223> OTHER INFORMATION: Actinohivin Variant Polypeptide

<400> SEQUENCE: 13

Ala Ser Gly Thr Ile Arg Asn Ala Glu Thr Gly Arg Leu Leu Asp Ser
1               5                   10                  15

Asn Tyr Asn Gly Asn Val Tyr Thr Leu Pro Ala Asn Gly Gly Asn Tyr
            20                  25                  30

Gln Arg Trp Thr Gly Pro Gly Asp Gly Thr Val Arg Asn Ala Glu Thr
        35                  40                  45

Gly Arg Leu Leu Asp Ser Asn Tyr Asn Gly Asn Val Tyr Thr Leu Pro
    50                  55                  60

Ala Asn Gly Gly Asn Tyr Gln Lys Trp Thr Gly Pro Gly Asp Gly Thr
65                  70                  75                  80

Ile Gln Asn Ala Glu Thr Gly Arg Val Leu Asp Ser Asn Tyr Asn Gly
                85                  90                  95

Asn Val Tyr Thr Leu Pro Ala Asn Gly Gly Asn Tyr Gln Lys Trp Thr
            100                 105                 110

Gly


<210> SEQ ID NO 14
<211> LENGTH: 113
<212> TYPE: PRT
<213> ORGANISM: Artificial Sequence
```

```
<220> FEATURE:
<223> OTHER INFORMATION: Actinohivin Variant Polypeptide

<400> SEQUENCE: 14

Ala Ser Gly Thr Ile Arg Asn Ala Glu Thr Gly Arg Cys Leu Asp Ser
1               5                   10                  15

Asn Tyr Asn Gly Asn Val Tyr Thr Leu Pro Cys Asn Gly Gly Asn Tyr
            20                  25                  30

Gln Arg Trp Thr Gly Pro Gly Asp Gly Thr Val Arg Asn Ala Glu Thr
        35                  40                  45

Gly Arg Cys Leu Asp Ser Asn Tyr Asn Gly Asn Val Tyr Thr Leu Pro
    50                  55                  60

Cys Asn Gly Gly Asn Tyr Gln Lys Trp Thr Gly Pro Gly Asp Gly Thr
65                  70                  75                  80

Ile Gln Asn Ala Glu Thr Gly Arg Cys Leu Asp Ser Asn Tyr Asn Gly
                85                  90                  95

Asn Val Tyr Thr Leu Pro Cys Asn Gly Gly Asn Tyr Gln Lys Trp Thr
            100                 105                 110

Gly


<210> SEQ ID NO 15
<211> LENGTH: 113
<212> TYPE: PRT
<213> ORGANISM: Artificial Sequence
<220> FEATURE:
<223> OTHER INFORMATION: Actinohivin Variant Polypeptide

<400> SEQUENCE: 15

Ala Ser Gly Thr Ile Arg Asn Ala Glu Thr Gly Arg Cys Leu Asp Ser
1               5                   10                  15

Asn Tyr Asp Gly Asn Val Tyr Thr Leu Pro Cys Asn Gly Gly Asn Tyr
            20                  25                  30

Gln Arg Trp Thr Gly Pro Gly Asp Gly Thr Val Arg Asn Ala Glu Thr
        35                  40                  45

Gly Arg Cys Leu Asp Ser Asn Tyr Asp Gly Asn Val Tyr Thr Leu Pro
    50                  55                  60

Cys Asn Gly Gly Asn Tyr Gln Lys Trp Thr Gly Pro Gly Asp Gly Thr
65                  70                  75                  80

Ile Gln Asn Ala Glu Thr Gly Arg Cys Leu Asp Ser Asn Tyr Asp Gly
                85                  90                  95

Asn Val Tyr Thr Leu Pro Cys Asn Gly Gly Asn Tyr Gln Lys Trp Thr
            100                 105                 110

Gly


<210> SEQ ID NO 16
<211> LENGTH: 350
<212> TYPE: PRT
<213> ORGANISM: Artificial Sequence
<220> FEATURE:
<223> OTHER INFORMATION: Actinohivin Variant Polypeptide 8 fused to Fc
      Region of IgG

<400> SEQUENCE: 16

Ala Ser Gly Thr Ile Arg Asn Ala Glu Thr Gly Arg Cys Leu Asp Ser
1               5                   10                  15

Asn Tyr Asn Gly Asn Val Tyr Thr Leu Pro Cys Asn Gly Gly Asn Tyr
            20                  25                  30

Gln Arg Trp Thr Gly Pro Gly Asp Gly Thr Val Arg Asn Ala Glu Thr
```

-continued

```
        35                  40                  45

Gly Arg Cys Leu Asp Ser Asn Tyr Asp Gly Ala Val Tyr Thr Leu Pro
    50                  55                  60

Cys Asn Gly Gly Ser Tyr Gln Lys Trp Thr Gly Pro Gly Asp Gly Thr
65                  70                  75                  80

Ile Gln Asn Ala Glu Thr Gly Arg Cys Leu Asp Ser Asn Tyr Asn Gly
                85                  90                  95

Asn Val Tyr Thr Leu Pro Cys Asn Gly Gly Asn Tyr Gln Lys Trp Thr
            100                 105                 110

Gly Gly Gly Gly Ser Val Glu Pro Lys Ser Cys Asp Lys Thr His Thr
        115                 120                 125

Cys Pro Pro Cys Pro Ala Pro Glu Leu Leu Gly Gly Pro Ser Val Phe
    130                 135                 140

Leu Phe Pro Pro Lys Pro Lys Asp Thr Leu Met Ile Ser Arg Thr Pro
145                 150                 155                 160

Glu Val Thr Cys Val Val Val Asp Val Ser His Glu Asp Pro Glu Val
                165                 170                 175

Lys Phe Asn Trp Tyr Val Asp Gly Val Glu Val His Asn Ala Lys Thr
            180                 185                 190

Lys Pro Arg Glu Glu Gln Tyr Asn Ser Thr Tyr Arg Val Val Ser Val
        195                 200                 205

Leu Thr Val Leu His Gln Asp Trp Leu Asn Gly Lys Glu Tyr Lys Cys
    210                 215                 220

Lys Val Ser Asn Lys Ala Leu Pro Ala Pro Ile Glu Lys Thr Ile Ser
225                 230                 235                 240

Lys Ala Lys Gly Gln Pro Arg Glu Pro Gln Val Tyr Thr Leu Pro Pro
                245                 250                 255

Ser Arg Glu Glu Met Thr Lys Asn Gln Val Ser Leu Thr Cys Leu Val
            260                 265                 270

Lys Gly Phe Tyr Pro Ser Asp Ile Ala Val Glu Trp Glu Ser Asn Gly
        275                 280                 285

Gln Pro Glu Asn Asn Tyr Lys Thr Thr Pro Pro Val Leu Asp Ser Asp
    290                 295                 300

Gly Ser Phe Phe Leu Tyr Ser Lys Leu Thr Val Asp Lys Ser Arg Trp
305                 310                 315                 320

Gln Gln Gly Asn Val Phe Ser Cys Ser Val Met His Glu Ala Leu His
                325                 330                 335

Asn His Tyr Thr Gln Lys Ser Leu Ser Leu Ser Pro Gly Lys
            340                 345                 350
```